United States Patent [19]
Johnson

[11] Patent Number: 5,356,818
[45] Date of Patent: Oct. 18, 1994

[54] SMOG MONITOR

[75] Inventor: Graham M. Johnson, Ryde, Australia

[73] Assignee: Commonwealth Scientific and Industrial Research Organisation, Campbell, Australia

[21] Appl. No.: 671,873

[22] PCT Filed: Aug. 30, 1989

[86] PCT No.: PCT/AU89/00367

§ 371 Date: Apr. 8, 1991

§ 102(e) Date: Apr. 8, 1991

[87] PCT Pub. No.: WO90/02329

PCT Pub. Date: Aug. 3, 1990

[30] Foreign Application Priority Data

Aug. 30, 1988 [AU] Australia ................... PJ0144
Sep. 19, 1988 [AU] Australia ................... PJ0488
Jun. 23, 1989 [AU] Australia ................... PJ4900

[51] Int. Cl.$^5$ ............................................. G01N 33/00
[52] U.S. Cl. ................................... 436/116; 436/135; 436/158; 436/145; 436/137; 422/83; 73/23.2; 73/31.01; 73/31.02; 73/31.05
[58] Field of Search ............... 436/135, 136, 116-118, 436/171; 422/83, 93, 91, 94; 73/23.2, 31.01, 31.02, 31.05; 423/385, 400, 405

[56] References Cited

U.S. PATENT DOCUMENTS

| | | | |
|---|---|---|---|
| 3,652,227 | 3/1972 | Harman, III et al. | 422/83 |
| 3,718,429 | 2/1973 | Williamson | 422/83 |
| 3,835,322 | 9/1974 | Kamatsu | 422/83 |
| 3,848,128 | 11/1974 | McMillan, Jr. | 422/83 |
| 3,877,875 | 4/1975 | Jones et al. | 422/80 |
| 3,924,442 | 12/1975 | Kerho et al. | 73/31.02 |
| 3,996,009 | 12/1976 | Fine et al. | 422/89 |
| 4,240,798 | 12/1980 | Wendelin et al. | 422/83 |
| 4,822,564 | 4/1989 | Howard | 422/52 |

OTHER PUBLICATIONS

"Sensitivity Analysis of a Math. Model for Photocehm. Air Pollution"; Tilden et al.; Atmospheric Env. v 16, N 6, pp. 1357-1364, 1982.

"The formation and inhibition of photochemical smog"; Heicklen J, Biosis No. 34059552, 1987, pp. 145-159.

"Effect of admixing fresh emissions on the photostationary state relationship in photochemical smog", Bilger, Atmospheric Env. v12, n5, 1978, pp. 1109-1118.

"A Method of Modeling Atmospheric Photochemical Reactions" Popov et al.; Gigiena I. Sanitariya (Journal Paper) No. 7, 1978, 45-49.

"Analysis of Ozone and Nitric oxide by Chemiluminescent Method in Lab. and Atmospheric Studies of Photochemical Smog"; Stedman et al,; Journal of the Air Pollution Control Assoc. v22 n4, 1972, 260-263.

A. Fried et al., Anal. Chem. 1988, 60, 394-403.

Primary Examiner—Robert J. Warden
Assistant Examiner—Hien Tran
Attorney, Agent, or Firm—Fitch, Even, Tabin & Flannery

[57] ABSTRACT

The amount of smog formed in air and the smog concentration in air is determined by measuring the consumption of nitric oxide.

2 Claims, 12 Drawing Sheets

SMOG MONITOR

TECHNICAL FIELD

This invention relates to methods and systems for analysing the formation of smog in air, and more particularly for determining:
(a) rate coefficient of smog formation in air;
(b) rate of smog formation in air under selected temperature and illumination conditions;
(c) time required for maximum smog formation in air under selected temperature and illumination conditions;
(d) time period during which smog formation in air has occurred;
(e) location of a source of Reactive Organic Compounds (ROC) present in air;
(f) time required for production of a given amount of smog in air;
(g) concentration of smog in air;
(h) amount of prior smog formation in air;
(i) maximum potential smog formation in air;
(j) current extent of smog formation in air;
(k) ozone concentration in air;
(l) nitric oxide, NO and/or ozone concentrations in air;
(m) Reactive Organic Compounds (ROC) concentration of air; and/or
(n) total concentration of ROC previously introduced into air. The following parameters can also be determined from the methods and systems of the invention: total concentration of nitric oxide previously introduced into air, total concentrations of $NO_x$ and $NO_y$ previously introduced into air, $ROC/NO_x$ concentration ratio of the total ROC and $NO_x$ previously introduced into air and average time of prior introductions of ROC into air.

BACKGROUND ART

Photochemical smog, which is commonly characterized by ozone concentrations in the order of 0.1 ppm or greater in air, is an air quality problem in many urban areas, particularly those with high levels of sunlight.

Photochemical smog formation passes through three sequential phases: (1) oxidation of NO to $NO_2$, (2) production of $O_3$, and (3) a final phase when $O_3$ is maintained at, or near, its maximum amount. Chemical processes occurring during each phase are intimately related and interactions between various competing and consecutive chemical reactions make analysis of smog formation difficult. Also because the atmosphere in a state of dynamic flux since, as well as changing dispersion variables, there are changing emissions and changing meteorological conditions, e.g. sunlight, rain and temperature. In the atmosphere smog formation does not always reach completion because reactants are often dispersed before the final phase.

As a consequence of the above difficulties there is presently, despite considerable prior research efforts, a need for systems and methods which can provide reliable measures of smog formation in the atmosphere.

The commonly employed measure of smog concentration, ozone concentration, gives only a partial indication of the amount of smog formation. This problem arises because many chemical species, in addition to ozone, are products of the smog forming reactions and also because ozone is not a stable compound and is readily consumed, especially by reaction with nitric oxide. Thus at any given time the observed concentration of ozone in air is dependent upon the amount of prior emissions of nitric oxide into the air.

Considerable efforts by the inventor have thus been directed towards developing a robust method for determining the amount of photochemical smog formation in air and a laboratory size smog chamber which provides reproducible and accurate estimates of the photochemical reactivty potential of air being tested therein. However, it has been found that prior art smog chambers are prone to give irreproducible and inaccurate results which are thought to be due to different contributions from many variables, e.g. nature of the chamber walls and surface reactions therewith, shaded zones in the chamber, mixing rates, outgassing, chamber pretreatment, chamber deposits, impurities in reactants, non-uniform temperatures, etc. and smog reaction rates that are dependent on the extent of reaction.

There is also a need for a method for predicting smog formation from Reactive Organic Compounds (ROC)/air mixtures. Such a method could be used for screening solvents and fuels and assessing the photoreactivities of hydrocarbon wastes.

Photochemical smog formation from reactive organic compounds (ROC)/nitric oxide/air mixtures occurs as follows:

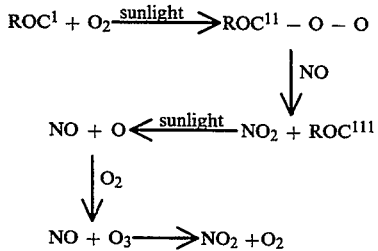

Present methods for measuring the essential reactant, ROC, which is essential for smog formation in the atmosphere are inadequate since they are either not sufficiently sensitive, are very cumbersome and labour-intensive or do not take account of the widely differing smog forming reactivities of the individual organic species which taken together comprise ROC. Frequently, the atmospheric concentrations of the individual ROC species, while sufficient to produce significant quantities of photochemical smog, are too small to be detected by the currently available sensors. Air can be analysed for ROC by high resolution gas chromatography using flame ionisation or photoionization detectors but these techniques require cumbersome sample preconcentration procedures, are labour-intensive and give data on only a subset of the photochemically active species present.

Furthermore, knowledge of the concentrations of the components of the ROC mixture does not allow the photochemical reactivity of the air to be quantitatively estimated because the role of many of the individual ROC species, and their reaction products, in the chemistry of smog formation, is uncertain. An approach sometimes adopted for ROC analysis is to measure the total non-methanic hydrocarbon concentration of the air as a single peak, backflushed from a chromatographic column after methane has been eluted, or alternatively as the difference in signal from air and air scrubbed of ROC species but without methane removal.

For some purposes this arrangement provides adequate sensitivity but the method is subject to errors in the measured concentrations because no account can be taken of the differing sensitivities of the detector to the various individual ROC species.

In other words, these techniques typically do not provide a measure of the reactivity of the total ROC in air since they do not provide the ROC compositions and this is important since in the atmosphere 250 or more ROC species have been identified of which there can be 60 major species or more and the rate of smog formation can be greatly affected by the nature and the relative proportions of the ROC species which are present.

Photochemical smog formation is a complex process wherein a multitude of reactant species are simultaneously consumed to give a wide variety of chemical product species. It is possible to measure the concentrations of many of these reactants and products and in the past such measurements have been utilized in various ways as indicators of the extent of photochemical smog production. For example, some measures that have been used to evaluate extent of reaction are: ozone concentration, peroxyacetyl nitrate concentration; nitrogen dioxide concentration; time to reach a maximum ozone concentration; time taken for the concentrations of NO and $NO_2$ to be equal, ozone concentration attained after illumination for a fixed period and intensity; time for NO concentration to reach one half of its initial value. Such data, however, gives only a limited indication of the progress of reaction and are complex and difficult to interpret in terms of the overall rate and extent of the smog-forming reactions. Additionally the rates at which these individual reactants and products are consumed and produced vary as smog formation progresses.

OBJECTS OF INVENTION

Objects of this invention are to provide methods and systems for analysing the formation of smog in air, and more particularly for determining:

(a) rate coefficient of smog formation in air;
(b) rate of smog formation in air under selected temperature and illumination conditions;
(c) time required for maximum smog formation in air under selected temperature and illumination conditions;
(d) time period during which smog formation in air has occurred;
(e) location of a source of Reactive Organic Compounds (ROC) present in air;
(f) time required for production of a given amount of smog in air;
(g) concentration of smog in air;
(h) amount of prior smog formation in air;
(i) maximum potential smog formation in air;
(j) current extent of smog formation in air;
(k) ozone concentration in air;
(l) nitric oxide, $NO_y$ and/or ozone concentrations in air;
(m) ROC concentration of air; and/or
(n) total concentration of prior ROC emissions into air.

| | DEFINITIONS |
|---|---|
| Air | Atmospheric air, including pristine air and pristine air into which smog-forming substances (including ROC and $NO_x$ have been introduced at some times (including up to some days) previously. Air may have undergone various transport and dispersion processes including mixing with air of other compositions and dilution by pristine air; |
| $a^t_{ROC}$ | Activity coefficient for smog formation by ROC at time t; (units: moles smog/mole ROC/unit illumination/unit f(T) or moles smog/mole ROC carbon/ unit illumination/unit f(T)) |
| $a_{ROC(i)}$ | Activity coefficient for smog formation from species ROC(i); |
| $V^t$ | Volume at time t; |
| $G^t$ | A parameter determined according to equation (58); |
| H | Coefficient of expression (70) and formulae derived from (70); |
| L | Coefficient of expression (70) and formulae derived from (70); |
| $E^t_{smog}$ | the extent of smog formation in air at time t, extent being the proportion of amount of smog produced by time t compared to the maximum potential amount of smog formation; |
| $NO_x$ | $NO + NO_2$; |
| $NO_y$ | "Total gaseous oxidized nitrogen" is the sum of $NO, NO_2$, peroxynitric acid, $(HO_2NO_2)$; nitric acid $(HNO_3)$; peroxyacetyl nitrate, (PAN); nitrous acid $(HNO_2)$, dinitrogen pentoxide $(N_2O_5)$, nitrate radical $(NO_3 \cdot)$ and other gaseous organic nitrates. Other nitrogen species at lower oxidation states, e.g. $N_2O$, $N_2$, $NH_3$, HCN, $CH_3CN$ are not components of $NO_y$; |
| Smog Concentration | The sum of the concentrations of ozone and $NO_y$ less the concentration of NO; |
| Amount of Smog Formation | The gross amount of nitric oxide oxidized in the air by smog chemistry, i.e. the moles of NO consumed by the reaction: $RO_2 \cdot + NO \rightarrow$ Products; |
| $RO_2 \cdot$ | Hydroxyl, alkoxy and peroxy free radical species; |
| ROC | Reactive organic compounds including carbonyl, alkane, alkene, aromatic, carbon monoxide and other types of gasphase carbonaceous species which when present in illuminated air undergo reaction wherein oxygen molecules are consumed and nitric oxide is oxidized; |
| ROC' ROC'' ROC''' | |
| ROC(i) | A specified individual ROC compound or a specified mixture of ROC compounds. |
| $^{T,I}Q^t_{smog}$ | Rate of smog formation in air at time (t) with temperature (T) and illumination intensity (I); |
| $X^t_{smog}$ | The mole fraction of smog in air at time t; |
| $^Ix_i$ | The mole fraction of species i in the mixture after |

| | -continued |
|---|---|
| | the first selected period; |
| $II_{x_i}$ | The mole fraction of species i in the mixture after |
| | the second selected period; |
| $III_{x_i}$ | The mole fraction of species i in the mixture after |
| | the third selected period; |
| $X_i^t$ | The mole fraction of species i in air at time t (mole fraction); |
| $n_i^t$ | Number of Moles, n, of species i in air of volume $V^t$ at time t (moles); |
| $m_V^t$ | The volume of a defined parcel of air (m) at time t; |
| $f_{n_{smog}}^t$ | Amount of previous smog formation in air of volume $V^t$ at time t (moles); |
| $^o n_i$ | Denotes emissions of number of moles, n, of species i into air; |
| $^o n_i^t$ | Cumulative emissions of species i into air of volume $V^t$ during time period t = O to t = t, in moles; |
| $n_{NO_x}^t$ | $n_{NO}^t + n_{NO_2}^t$; |
| $^o F_{NO}$ | The fraction of NO in $NO_x$ emissions $(^o n_{NO}/^o n_{NO_x})$; |
| $f_{X_{smog}}^t$ | The notional concentration of smog formed in air in the absence of $NO_y$ removal processes (mole fraction); |
| $o_{X_i} t$ | The cumulative emissions of species i into air expressed as a fraction of the moles of species i emitted to the moles of air (mole fraction); |
| $^{extra}X_{smog}^t$ | Concentration of smog to be produced at some future time (mole fraction); |
| $added_{n_i}$ | Number of moles, n, of species i added to the air in the course of analysis (moles); |
| $^I n_{NO}$ | Number of moles, n, of NO present after first selected period (moles); |
| $k_j^t$ | Rate coefficient of reaction j at time t; |
| $R_j^t$ | Rate of reaction j at time t; |
| $P_{j,k}$ | Ratio of rate of reaction j to rate of reaction k $P_{j,k} = R_j/R_k$; |
| $^{fmax}n_{smog}$ | Maximum potential moles of smog formation in air; |
| $^{Tmax}n_{smog}$ | Maximum potential moles of smog that can be present in air, being total of contributions from both smog formation processes and emissions of $NO_2$; |
| $^{select}X_{smog}$ | A selected concentration of smog in air (mole fraction); |
| $^{fmax}X_{smog}^t$ | Maximum potential concentration of smog formed in air (mole fraction); |
| $^{Tmax}X_{smog}^t$ | Maximum potential concentration of smog that can be present in air, being total of contributions from both smog formation processes and emissions of $NO_2$ into air (mole fraction); |
| $R_{smog}^t$ | Rate coefficient for smog formation at time t; |
| R | Gas constant; |
| $p^t$ | Pressure at time t; |
| $T^t$ | Temperature at time t; |
| $X_i^r$ | Concentration of species i in reference air; |
| $v_n$ | Volume injected by device n in a specified time; |
| f | Flowrate; |
| $I^t$ | Illumination intensity (in units of rate coefficient for $NO_2$ photolysis, $min^{-1}$). |
| $\gamma$ | Coefficient of equation (39); |
| $\beta$ | A coefficient of smog formation. |
| "reference temperature and illumination conditions" | Can be simply known temperature and illumination conditions or can be conditions determined with reference to a reference gas under the same or known temperature and illumination conditions. |

DISCLOSURE OF INVENTION

The present inventor has found that the amount of smog formed in air and the smog concentration in air can be determined by the consumption of a single species, namely nitric oxide, and more particularly the oxidation of NO. A key step leading to smog formation is the dissociation of oxygen molecules by various smog forming reactions. The present inventor has found that for each oxygen molecule thus dissociated it can be taken that an approximately equivalent amount of nitric oxide is caused to be consumed.

Measurement of the total amount of nitric oxide consumed thus provides a quantitative measure of the amount of smog produced. The rate of smog formation can be determined by the amount of smog produced, as indicated by nitric oxide consumption (and thus oxygen dissociation) in the presence of excess nitric oxide, during a selected period under selected conditions of illumination and temperature. Alternatively, for the measurement of smog formation rate the total amount of nitric oxide consumed during the selected reaction period can be determined by addition of excess ozone to the air prior to the selected period in which circumstances the gross consumption of nitric oxide is measured as increase in ozone concentration, there being an equivalence between the nitric oxide consumed and the ozone produced under the selected conditions. Brief summaries of the techniques used to determine various parameters are given below:

1A. Determination of the Amount of Smog Formed in Air

This can be achieved by firstly sampling the air, secondly adding NO so that it is present in excess and, thirdly, measuring the difference between the total amount of nitric oxide which has been present in the air (i.e. the NO emissions into the air prior to sampling plus that added during analysis) and the concentration of residual NO present after the added NO has been allowed to react with and be consumed by any ozone that may have been present in the air.

1B. Determination of Smog Concentration in Air

Concentration of smog in air is determined by addition of excess nitric oxide to the air and after reaction with substantially all ozone present determining the concentration of smog as the difference between the total concentration of the oxidised nitrogen species (i.e. NO, $NO_2$, peroxyacetyl nitrate, gaseous nitric acid etc) in the mixture and the nitric oxide concentration of the mixture.

A second function of the nitric oxide addition is that by removing ozone it stabilises the air in the dark, minimising the production of nitric acid within the apparatus. This is beneficial because nitric acid is readily absorbed on surfaces and can thus be lost from the gas phase within the apparatus and before being measured at the detector.

2A. Determination of Rate Coefficient for Smog Formation

Rate coefficient for smog formation is determined by subjecting air containing excess NO to photochemical reaction under controlled conditions of temperature and illumination and by measuring the rate at which excess nitric oxide is consumed. A second function of the addition of excess nitric oxide to the air is that when excess nitric oxide is present the rate of nitric oxide consumption is, to a good approximation, independent of the extent of smog formation. Addition of excess nitric oxide makes the measured rate of smog formation independent of the original nitric oxide concentration of the air.

A further function of the excess nitric oxide is that it minimises the concentration of ozone in the system, thus minimising the ozone induced side reactions such as formation of nitric acid and nitrous acids in the unilluminated parts of the system. Ozone can also undergo unwanted reactions in the dark with alkenes.

2B. Determination of Rate Coefficient for Smog Formation in Air

Rate coefficient for smog formation in air is determined by subjecting air containing excess ozone to photochemical reaction under controlled conditions of temperature and illumination and by measuring the rate at which further amounts of ozone are produced. In the presence of excess ozone, nitric oxide is consumed by the smog-forming reactions to produce nitrogen dioxide. Nitrogen dioxide undergoes photochemical reaction to produce ozone and regenerate nitric oxide. A small, steady state, nitric oxide concentration is thus maintained. The net amount of ozone produced under these conditions is a measure of the amount of nitric oxide consumed by smog formation and is thus a measure of the amount of oxygen molecules consumed by smog formation.

3. Prediction of Extent of Maximum Potential Smog Formation in Air

Prediction of the extent of maximum potential smog formation in be ascertained by determination of rate coefficient of smog formation, smog concentration and the total oxidised nitrogen concentration of the air ($NO_y$) and the application of computational formulae as described herein.

4. Prediction of Rate and Extent of Smog Formation in Air Under Selected Conditions Prediction of the rate and extent of smog formation that would apply to sampled air when subjected to a wide range of selected atmospheric conditions can be ascertained from the above determined properties of the air and application of the computational formulae described herein.

5. Determination of Time Required for Formation of Selected Amounts of Smog in Air Under Selected Conditions Determination of the time required for formation of selected amounts of smog in air under a wide range of selected conditions can be ascertained from the above determined properties of the air and application of the computational formulae described herein.

6. Determination

ROC concentration is determined by subjecting air containing excess NO to photochemical reaction under controlled conditions of temperature and illumination for a selected period and by measuring the concentration excess nitric oxide consumed. The nitric oxide consumption is proportional to the ROC concentration of the air and is thus a measure of the ROC concentration of the air. A second function of the addition of excess nitric oxide to the air is that when excess nitric oxide is present nitric oxide consumption is, to a good approximation, independent of the extent of previous photochemical reaction involving the ROC. Addition of excess nitric oxide makes smog formation independent of the original nitric oxide concentration of the air.

A further function of the excess nitric oxide is that it minimises the concentration of ozone in the system, thus minimising ozone induced side reactions such as formation of nitric acid in the unilluminated parts of the system. Ozone can also undergo unwanted reactions in the dark with alkenes.

| TABLE SUMMARISING EMBODIMENTS | |
|---|---|
| Number of Embodiment | Brief Description of Embodiments |
| 1 | Method for determining rate coefficient of smog formation in air; (via NO excess); |
| 2 | Method for determining rate coefficient of smog formation in air; (via $O_3$ excess); |
| 3 | Method for determining concentration of smog in air; |
| 4 | Method for determining amount of prior smog formation in air; |
| 5 | Method for determining maximum potential and optionally the current extent of smog formation in air; |
| 6 | Method for determining rate of smog formation in air under selected temperature and illumination (via excess NO); |
| 7 | Method for determining rate of smog formation in air under selected temperature and illumination (via excess $O_3$); |
| 8 | Method for determining time required for maximum smog formation in air under selected conditions of illumination and temperature; |
| 9 | Method for determining time period during which smog formation in air has occurred; |
| 10 | Method for determining time required for production of a given amount of smog in air under selected temperature and illumination conditions; |
| 11 | Method of determining ozone concentration in air (via determined NO and smog concentrations); |
| 12 | Method for determining nitric oxide and $NO_y$ or ozone or both concentrations in air (via determined sunlight, temperature, $NO_y$ and smog concentrations); |
| 13 | System for determining rate coefficient of smog formation in air (corresponding to method 1, via NO); |
| 14 | System for determining rate coefficient of smog formation in air (corresponding to method 2, via $O_3$); |
| 15 | System for determining concentration of smog in air (corresponding to method 3); |
| 16 | System for determining amount of prior smog formation in air (corresponding to method 4); |
| 17 | System for determining maximum potential and optionally the current extent of smog formation in air (Corresponding to method 5); |
| 18 | System for determining rate of smog formation |

-continued

TABLE SUMMARISING EMBODIMENTS

| Number of Embodiment | Brief Description of Embodiments |
|---|---|
| | in air under selected temperature and illumination conditions (corresponding to method 6, NO excess); |
| 19 | System for determining rate of smog formation in air under selected temperature and illumination conditions (corresponding to method 7, $O_3$ excess); |
| 20 | System for determining time required for maximum smog formation in air under selected conditions of illumination and temperature (corresponding to method 8); |
| 21 | System for determining time period during which smog formation in air has occurred (corresponding to method 9); |
| 22 | System for determining time required for production of a selected amount of smog in air under selected temperature and illumination conditions (corresponding to method 10); |
| 23 | System for determining ozone concentration of air (corresponding to method 11, via determined NO and smog concentrations); |
| 24 | System for determining nitric oxide and $NO_y$ or ozone or both concentrations in air (corresponding to method 12); |
| 25 | Method for determining ROC concentration of air and/or total concentration of prior ROC emissions into air; and |
| 26 | System for determining ROC concentration of air and/or total concentration of prior ROC emissions into air (corresponding to method 25). |

According to a first embodiment of this invention there is provided a method for determining rate coefficient of smog formation in air, the method comprising:
(a) adding excess nitric oxide to the air to provide an excess nitric oxide/air mixture;
(b) permitting the mixture to react for a first selected period wherein excess nitric oxide in the mixture reacts with substantially all ozone in the mixture;
(c) determining a first nitric oxide concentration of the mixture after the first selected period;
(d) illuminating the mixture of (a) or the mixture after the first selected period for a second selected period under reference temperature and illumination conditions;
(e) permitting the mixture, after illumination, to react for a third selected period wherein excess nitric oxide in the mixture reacts with any ozone present in the mixture;
(f) determining a second nitric oxide concentration of the mixture after the third selected period; and
(g) determining the rate coefficient of smog formation from the first and second nitric oxide concentrations, the reference temperature and illumination conditions and the duration of the second selected period.

According to a second embodiment of this invention there is provided a method for determining rate coefficient of smog formation in air, the method comprising:
(a) adding excess ozone to the air to provide an excess ozone/air mixture;
(b) permitting the mixture to react for a first selected period wherein excess ozone in the mixture reacts with substantially all nitric oxide in the mixture;
(c) determining a first ozone concentration of the mixture after the first selected period;
(d) illuminating the mixture of (a) or the mixture after the first selected period for a second selected period under reference temperature and illumination conditions;
(e) permitting the mixture, after illumination, to react for a third selected period wherein excess ozone in the mixture reacts with any nitric oxide present in the mixture;
(f) determining a second ozone concentration of the mixture after the third selected period; and
(g) determining the rate coefficient from the first and second ozone concentrations, the reference temperature and illumination conditions and the duration of the second selected period.

Optionally the method of the second embodiment further includes the step of (a)(i) adding a quantity of nitrogen oxides to the mixture prior to step (b). This optional step is recommended for those occasions when the nitrogen oxides concentration of the air is small and limiting on the rate of reaction during step (d).

According to a third embodiment of this invention there is provided a method for determining concentration of smog in air, which method comprises:
(a) adding excess nitric oxide to the air to provide an excess nitric oxide/air mixture;
(b) reacting the mixture for a selected period wherein the excess nitric oxide reacts with substantially all ozone in the mixture;
(c) determining the nitric oxide concentration of the mixture after the selected period;
(d) determining the total oxidized nitrogen ($NO_y$) concentration of the mixture after the selected period; and
(e) determining the concentration of smog in the air from the nitric oxide concentration of (c) and the $NO_y$ concentration of (d).

Optionally the method of the third embodiment further includes the step of (c)(i) converting $NO_y$ in the mixture to nitric oxide prior to step (d). When step(c)(i) is included the $NO_y$ concentration in step d) can be determined by simply determining the nitric oxide concentration of the mixture.

According to a fourth embodiment of this invention there is provided a method for determining the amount of prior smog formation in air, which method comprises:
(A) determining $NO_y$ concentration of air;
(B) determining the concentration of smog in air by the method of the third embodiment;
(C) determining the concentration of total nitrogen oxides previously emitted into the air from the $NO_y$ concentration in the air and the concentration of smog in the air; and
(D) determining the amount of prior smog formation in air from the concentration of total nitrogen oxides previously emitted into the air as determined in step (C) and the concentration of smog in the air as determined in (B).

Optionally the method of the fourth embodiment further includes the steps of (A)(i), converting $NO_y$ in the air to nitric oxide prior to step (A). When step (A)(i) is included the concentration in step (A) can be determined by simply determining the nitric oxide concentration of the air.

According to a fifth embodiment of this invention there is provided a method for determining maximum potential smog formation in air, which method comprises:
- (α) determining the amount of prior smog formation in air by the method of the fourth embodiment;
- (β) determining the concentration of total nitrogen oxides previously emitted into the air from the $NO_y$ concentration in the air and the concentration of smog in the air; and
- (γ) determining the maximum potential smog formation in the air from the concentration of total nitrogen oxides previously emitted into the air.

According to a sixth embodiment of this invention there is provided a method for determining rate of smog formation in air under selected temperature and illumination conditions, which method comprises:
- (a) adding excess nitric oxide to the air to provide an excess nitric oxide/air mixture;
- (b) permitting the mixture to react for a first selected period wherein excess nitric oxide in the mixture reacts with substantially all ozone in the mixture;
- (c) determining a first nitric oxide concentration of the mixture after the first selected period;
- (d) illuminating the mixture of (a) or the mixture after the first selected period for a second selected period under selected temperature and illumination conditions;
- (e) permitting the mixture, after illumination, to react for a third selected period wherein excess nitric oxide in the mixture reacts with any ozone present in the mixture;
- (f) determining a second nitric oxide concentration of the mixture after the third selected period; and
- (g) determining the rate from the First and second nitric oxide concentrations and the duration of the second selected period.

According to a seventh embodiment of this invention there is provided a method for determining rate of smog formation in air under selected temperature and illumination conditions, which method comprises:
- (a) adding excess ozone to the air to provide an excess ozone/air mixture;
- (b) permitting the mixture to react for a first selected period wherein excess ozone in the mixture reacts with substantially all nitric oxide in the mixture;
- (c) determining a first ozone concentration of the mixture after the first selected period;
- (d) illuminating the mixture of (a) or the mixture after the first selected period for a second selected period under selected temperature and illumination conditions;
- (e) permitting the mixture, after illumination, to react for a third selected period wherein excess ozone in the mixture reacts with any nitric oxide present in the mixture;
- (f) determining a second ozone concentration of the mixture after the third selected period; and
- (g) determining the rate from the first and second ozone concentrations and the duration of the second selected period.

Optionally the method of the seventh embodiment further includes the step of (a)(i) adding a quantity of nitrogen oxides to the mixture prior to step (b). This optional step is recommended for those occasions when the nitrogen oxides concentration of the air is small and limiting on the rate of reaction during step (d).

According to an eighth embodiment of this invention there is provided a method for determining time required for maximum smog formation in air under selected conditions of illumination and temperature, the method comprising:
- (A) determining rate coefficient of smog formation in the air according to the method of the first or second embodiments or;
- (A)(i) determining rate of smog formation in the air under the selected conditions according to the method of the sixth or seventh embodiments;
- (B) determining maximum potential smog formation in the air according to the method of the fifth embodiment; and
- (C) determining the time for maximum smog formation, under selected temperature and illumination conditions, From the maximum potential smog formation and the rate coefficient; or
- (C)(i) determining the time for maximum smog formation, under selected temperature and illumination conditions, from the maximum potential smog formation and the rate.

According to a ninth embodiment of this invention there is provided a method for determining time period during which smog formation in air has occurred, the time period being substantially the same as or within predetermined period for which the illumination and temperature conditions are known, wherein the end of the predetermined period coincides with the end of the time period, the method comprising:
- (A) determining temperatures of the air for the predetermined period;
- (B) determining sunlight intensities for the predetermined period;
- (C) determining the rate coefficient of smog formation according to the method of the first or second embodiments; or
- (C)(i) determining rates of smog formation in the air according to the methods of the sixth or seventh embodiments under temperatures and light intensities corresponding to the determined temperatures and sunlight intensities;
- (D) determining the amount of prior smog formation in the air at the end of the time period according to the method of the fourth embodiment; and
- (E) determining the time period during which the smog formation in the air has occurred from the amount of prior smog formation, the rate coefficient, the determined temperatures and sunlight intensities, or
- (E)(i) determining the time period during which the smog formation in the air has occurred from the amount of prior smog formation and the rates of smog formation.

Optionally the location of the source of ROC present in air may be determined on the basis of the time period of smog formation and separately determined speed of movement and trajectory of the air during the time period.

According to a tenth embodiment of this invention there is provided a method for determining time required for production of a selected amount of smog in air under selected temperature and illumination conditions and with selected initial amount of smog in the air, the method comprising:

(A) determining rate coefficient of smog formation in air according to the method of the first or second embodiments; or (A)(i) determining rates of smog formation in the air under the selected temperature and illumination conditions according to the method of the sixth or seventh embodiments;

(B) determining $NO_y$ concentration of the (C) determining the amount of $NO_y$ previously emitted into the air from the $NO_y$ concentration of (B) and the selected initial amount of smog in the air; and (D) determining the time required for production of selected amount of smog in the air for the selected conditions of temperature and illumination from the rate coefficient and the amount of $NO_y$; or (D)(i) determining the time required for production of the selected amount of smog in the air for the selected conditions of temperature and illumination from the rate and the amount of $NO_y$ previously emitted into the air.

Optionally the method of the tenth embodiment further includes the steps of(A)(i), converting $NO_y$ in the air to nitric oxide prior to step (B). When step (A)(ii) is included the concentration in step (B) can be determined by simply determining the nitric oxide concentration of the air.

According to an eleventh embodiment of this invention there provided a method for determining ozone concentration in air, which method comprises:

(A) determining nitric oxide concentration of the air;

(B) determining $NO_y$ concentration of the air;

(C) determining concentration of smog in the air according to the method of the third embodiment; and (D) calculating the ozone concentration of the air from the measured nitric oxide concentration, $NO_y$ concentration and the concentration of smog in the According to a twelfth embodiment of this invention there is provided a method for determining nitric oxide and/or ozone concentrations in air, which method comprises:

(A) determining the sunlight intensity of the air;

(B) determining the temperature of the air;

(C) determining the $NO_y$ concentration of the air;

(D) determining the smog concentration of the air according to the method of the third embodiment; and (E) determining the concentrations of nitric oxide and/or ozone in air from the $NO_y$ and smog concentrations, the sunlight intensity and the temperature.

Optionally the method of the twelfth embodiment further includes step(B)(i); converting $NO_y$ in the air to nitric oxide prior to step (C). When step (B)(i) is included the concentration in step (C) can be determined by simply determining the nitric oxide concentration of the air According to a thirteenth embodiment of this invention there is provided a system for determining rate coefficient of smog formation in air, which system comprises:

(a) a combiner for combining excess nitric oxide with the air to provide an excess nitric oxide/air mixture;

(b) a first reactor operatively associated with the combiner wherein the mixture can react in the first reactor for a first selected period wherein excess nitric oxide in the mixture reacts with substantially all ozone in the mixture;

(c) a photoreactor operatively associated with the combiner and optionally the first reactor;

(d) an illumination source operatively disposed about the photoreactor to illuminate the mixture of (a) in the photoreactor, or the mixture after the first selected period, in the photoreactor for a second selected period under known temperature and illumination conditions;

(e) a second reactor operatively associated with the photoreactor wherein the mixture can react in the second reactor for a third selected period wherein excess nitric oxide in the mixture reacts with substantially all ozone in the mixture;

(f) a nitric oxide analyser operatively associated with the first reactor, to determine a first nitric oxide concentration of the mixture after the first selected period and operatively associated with the second reactor to determine a second nitric oxide concentration of the mixture after the third selected period;

(g) a temperature sensor operatively associated with the photoreactor to determine the temperature of the mixture;

(h) an illumination sensor operatively associated with the illumination source to determine the amount of illumination of the illuminated mixture; and (i) calculating means operatively associated with the temperature and illumination sensors and the nitric oxide analyser to calculate the rate coefficient from the first and second nitric oxide concentrations, the known temperature and illumination conditions and the duration of the second selected period.

According to a fourteenth embodiment of this invention there is provided a system for determining rate coefficient of smog formation in air, which system comprises:

(a) a first combiner for combining excess ozone with the air to provide an excess ozone/air mixture;

(b) a first reactor operatively associated with the combiner wherein the mixture can react in the first reactor for a first selected period wherein excess ozone in the mixture reacts with substantially all nitric oxide in the mixture;

(c) a photoreactor operatively associated with the combiner and optionally the first reactor;

(d) an illumination source operatively disposed about the photoreactor to illuminate the mixture of (a) in the photoreactor, or the mixture after the first selected period, in the photoreactor for a second selected period under known temperature and illumination conditions;

(e) a second reactor operatively associated with the photoreactor wherein the mixture can react in the second reactor for a third selected period wherein excess ozone in the mixture reacts with substantially all nitric oxide in the mixture;

(f) an ozone analyser operatively associated with the first reactor to determine a first ozone concentration of the mixture after the first selected period and operatively associated with the second reactor to determine a second ozone concentration of the mixture after the third selected period;

(g) a temperature sensor operatively associated with the photoreactor to determine the temperature of the mixture;

(h) an illumination sensor operatively associated with the illumination source to determine the amount of illumination of the illuminated mixture; and (i) calculating means operatively associated with the temperature and illumination sensors and the ozone analyser to calculate the rate coefficient from the first and second ozone concentrations, the known temperature and illumination conditions and the duration of the second selected period.

Optionally the system of the fourteenth embodiment further includes a second combiner operatively associated with the first combiner for combining a quantity of nitrogen oxides with the air.

According to a fifteenth embodiment of this invention there is provided a system for determining concentration of smog in air, which system comprises:

(a) a combiner for combining excess nitric oxide with the air to provide an excess nitric oxide/air mixture;

(b) a reactor operatively associated with the combiner wherein the mixture can react in the reactor for a selected period wherein excess nitric oxide in the mixture reacts with substantially all ozone in the mixture;

(c) a nitric oxide analyser operatively associated with the reactor to determine the nitric oxide concentration of the mixture after the selected period;

(d) a $NO_y$ analyser operatively associated with the reactor to determine the $NO_y$ concentration of the mixture; and (e) calculating means operatively associated with the nitric oxide analyser and the $NO_y$ analyser to calculate the concentration of smog from the $NO_y$ and nitric oxide concentrations.

Preferably the $NO_y$ analyser of (d) includes a $NO_y$ converter to convert all $NO_y$ in the mixture to nitric oxide, the converter being operatively associated with the nitric oxide analyser of (c). In this preferred arrangement the $NO_y$ analyser consists of the $NO_y$ converter and the nitric oxide analyser of (c).

According to a sixteenth embodiment of this invention there is provided a system for determining amount of prior smog formation in air, which system comprises:

(a) a first $NO_y$ analyser to determine the $NO_y$ concentration of the air;

(b) a combiner for combining excess nitric oxide with the air to provide an excess nitric oxide/air mixture;

(c) a reactor operatively associated with the combiner wherein the mixture can react in the reactor for a selected period wherein excess nitric oxide in the mixture reacts with substantially all ozone in the mixture;

(d) a nitric oxide analyser operatively associated with the reactor to determine the nitric oxide concentration of the mixture after the selected period;

(e) a second $NO_y$ analyser operatively associated with the reactor to determine the $NO_y$ concentration of the mixture; and (f) calculating means operatively associated with the nitric oxide analyser and the first and second $NO_y$ analysers to calculate the amount of prior smog formation in air from the $NO_y$ concentration of the air and the NO and $NO_y$ concentrations of the excess nitric oxide/air mixture.

Preferably the $NO_y$ analyser of (a) is the same $NO_y$ analyser employed in (e) operatively associated to the combiner of (b) so as to determine the $NO_y$ concentration of air before excess nitric oxide is combined with air.

Also preferably the $NO_y$ analyser of (a) and (d) includes a $NO_y$ converter to convert all $NO_y$ in the mixture to nitric oxide, the converter being operatively associated with the nitric oxide analyser of (d). In this preferred arrangement the $NO_y$ analyser consists of the $NO_y$ converter and the nitric oxide analyser of (d).

According to a seventeenth embodiment of this invention there is provided a system for determining maximum potential and optionally the current extent of smog formation in air, which system comprises:

(a) a first $NO_y$ analyser for determining the $NO_y$ concentration of the air;

(b) a combiner for combining excess nitric oxide with the air to provide an excess nitric oxide/air mixture;

(c) a reactor operatively associated with the combiner wherein the mixture can react in the reactor for a selected period wherein excess nitric oxide in the mixture reacts with substantially all ozone in the mixture:

(d) a nitric oxide analyser operatively associated with the reactor to determine the nitric oxide concentration of the mixture after the selected period:

(e) a second $NO_y$ analyser operatively associated with the reactor to determine the $NO_y$ concentration of the mixture; and (f) calculating means operatively associated and coupled with the nitric oxide analyser and the first and second $NO_y$ analysers to calculate the maximum potential and optionally the current extent of smog formation in air from the $NO_y$ concentration of the air and the $NO_y$ and $NO_Y$ concentrations of the excess nitric oxide/air mixture.

Preferably the $NO_y$ analyser of (a) is the same $NO_y$ analyser employed in (e) coupled to and operatively associated to the combiner of (b) so as to determine the $NO_y$ concentration of air before excess nitric oxide is combined with air.

Also preferably the $NO_y$ analyser of (a) and (e) includes a $NO_y$ converter to convert all $NO_y$ in the mixture to nitric oxide, the converter being operatively associated with the nitric oxide analyser of (d). In this preferred arrangement the $NO_y$ analyser consists of the $NO_y$ converter and the nitric oxide analyser of (d).

According to an eighteenth embodiment of this invention there is provided a system for determining rate of smog formation in air under selected temperature and illumination conditions, which system comprises:

(a) a combiner for combining excess nitric oxide with the air to provide an excess nitric oxide/air mixture;

(b) a first reactor operatively associated with the combiner wherein the mixture can react in the first reactor for a first selected period wherein excess nitric oxide in the mixture reacts with substantially all ozone in the mixture;

(c) a photoreactor operatively associated with the combiner and optionally the first reactor;

(d) an illumination source operatively disposed about the photoreactor to illuminate the mixture of (a), in the photoreactor, or the mixture after the first selected period, in the photoreactor for a second selected period under selected temperature and illumination conditions;

(e) a second reactor operatively associated with the photoreactor wherein the mixture can in the second reactor react for a third selected period wherein excess nitric oxide in the mixture reacts with substantially all ozone in the mixture;

(f) a nitric oxide analyser operatively associated with the first reactor to determine a first nitric oxide concentration of the mixture after the first selected period and operatively associated with the second reactor to determine a second nitric oxide concentration of the mixture after the third selected period; and (g) calculating means operatively associated with the nitric oxide analyser to calculate the rate from the first and second nitric oxide concentrations and the duration of the second selected period.

According to a nineteenth embodiment of this invention there is provided a system for determining rate of smog formation in air under selected temperature and illumination conditions, which system comprises:

(a) a first combiner for combining excess ozone is combined with the air to provide an excess ozone/air mixture;

(b) a first reactor operatively associated with the combiner wherein the mixture can react in the reactor for a first selected period wherein excess ozone in the mixture reacts with substantially all nitric oxide in the mixture;

(c) a photoreactor operatively associated with the combiner and optionally the first reactor;

(d) an illumination source operatively disposed about the photoreactor to illuminate the mixture of (a), in the photoreactor, or the mixture after the first selected period, in the photoreactor for a second selected period under selected temperature and illumination conditions;

(e) a second reactor operatively associated with the photoreactor wherein the mixture can react in the second reactor for a third selected period wherein excess ozone in the mixture reacts with substantially all nitric oxide in the mixture;

(f) an ozone analyser operatively associated with the first reactor to determine a first ozone concentration of the mixture after the first selected period and operatively associated with the second reactor to determine a second ozone concentration of the mixture after the third selected period; and (g) calculating means operatively associated with the ozone analyser to calculate the rate from the first and second ozone concentrations and the duration of the second selected period.

In preferred embodiments of the thirteenth, fourteenth, eighteenth and nineteenth embodiments the first and second reactors and the photoreactor are the same reactor. In other preferred embodiments the first reactor and the photoreactor are the same reactor and in yet other embodiments the second reactor and the photoreactor are the same reactor.

In still other preferred embodiments the first reactor and photoreactor are two separate vessels through which the mixture can continuously flow in separate streams and the second reactor is a separate vessel through which the mixture from the photoreactor can continuously flow.

In such embodiments, the first reactor provides a first residence time for the mixture when continuously flowing therethrough and the photoreactor and the second reactor in combination provide a second residence time for the mixture when continuously flowing therethrough, the first and second residence times being substantially the same.

Optionally the system of the nineteenth embodiment further includes a second combiner operatively associated with the combiner of ozone in which second combiner a quantity of $NO_x$ is added to air. This is recommended when the nitric oxide concentration of air is small and limiting on the rate of reaction in the photolytic reactor.

According to a twentieth embodiment of this invention there is provided a system for determining time required for maximum smog formation in air under selected conditions of illumination and temperature wherein the system includes:

(A) a $NO_y$ analyser to determine the $NO_y$ concentration of the air;

(B) the system of the thirteenth or fourteenth embodiments to determine the rate coefficient of smog formation in the air; or (B)(i) the system of the eighteenth or nineteenth embodiments to determine the rates of the smog formation in air under the selected conditions;

(C) the system of the seventeenth embodiment to determine the maximum potential smog formation in the air; and (D) calculating means operatively associated with the analyser of (A) and the systems of (B) and (C) to calculate the maximum time for smog formation, under the selected temperature and illumination conditions from the $NO_y$ concentration, the extent of smog formation and the rate coefficient; or (D)(i) calculating means operatively associated with the analyser of (A) and the systems of (B)(i) and (C) to calculate the maximum time for smog formation, under the selected temperature and illumination conditions from the $NO_y$ concentration, the extent of smog formation and the rates.

Preferably the $NO_y$ analyser of (A) includes a $NO_y$ converter to convert all the $NO_y$ in the air to nitric oxide and a nitric oxide analyser to determine the total nitric oxide in this preferred arrangement the $NO_y$ analyser consists of the $NO_y$ converter and the nitric oxide analyser and the NO analysers of the systems of (A), (B) or (B)(i) and (C) are the same analyser, According to a twenty-first embodiment of this invention there is provided a system for determining time period during which smog formation in air has occurred, the time period being substantially the same as or within a selected period for which the illumination and temperature conditions are known, wherein the end of the selected period coincides with the end of the time period the system includes:

(A) the system of the thirteenth or fourteenth embodiments for determining the rate coefficient of smog formation in the air; or (A)(i) the system of the eighteenth or nineteenth embodiments for determining the rates of smog formation in the air;
(B) the system of the fifteenth embodiment for determining concentration of smog in the air;
(C) an $NO_y$ analyser for determining the $NO_y$ concentration of air;
(D) a temperature sensor to determine the temperature of the air for the duration of the selected period;
(E) a light sensor to determine the sunlight illumination during the selected period; and
(F) calculating means operatively associated with the temperature sensor, the light sensor, the $NO_y$ analyser and the systems for determining the rate coefficient of smog formation and smog concentration, to calculate the time period during which smog formation in air has occurred under the measured sunlight and temperature conditions; or
(F)(i) calculating means operatively associated with the temperature sensor, the light sensor, the $NO_y$ analyser and the systems of a(i) and (b) to calculate the time period during which smog formation has occurred under the measured sunlight and temperature conditions.

Preferably the $NO_y$ analyser of (C) includes a $NO_y$ converter to convert all $NO_y$ in the mixture to nitric oxide, the converter being operatively associated with a nitric oxide analyser. In this preferred arrangement the $NO_y$ analyser consists of the $NO_y$ converter and the nitric oxide analyser and the $NO_y$ analysers of the systems of (A) and (B) and the NO analyser of (C) are the same analyser.

Optionally the system of the twenty-first embodiment further includes means of determining the speed and trajectory of the air during the selected period and calculating means to determine the location of the emission sources of ROC present in air on the basis of the time period of smog formation, the air speed and trajectory.

According to a twenty-second embodiment of this invention there is provided a system for determining time required for production of a selected amount of smog in air under selected temperature and illumination conditions the system comprising
(A) the system of the thirteenth or fourteenth embodiments for determining rate coefficient of smog formation in the air; or
(A)(i) the system of the eighteenth or nineteenth embodiments for determining the rates of smog formation in the air;
(B) the system of the fifteenth embodiment for determining concentration of smog in the air;
(C) an $NO_y$ analyser for determining the $NO_y$ concentration of the air; and
(D) calculating means operatively associated with the systems for determining: the rate coefficient, smog concentration and the $NO_y$ analyser, to calculate the time required for the production of a selected amount of smog in the air under selected temperature and illumination conditions; or
(D)(i) calculating means operatively associated with the systems of (A)(i) and (B) and the $NO_y$ analyser, to calculate the time required for the production of a selected amount of smog in air under selected temperature and illumination conditions.

Preferably the $NO_y$ analyser of (C) includes a $NO_y$ converter to convert substantially all $NO_y$ in the mixture to nitric oxide, the converter being operatively associated with the nitric oxide analyser of (B). In this preferred arrangement the $NO_y$ analyser consists of the $NO_y$ converter and the nitric oxide analyser of (B).

According to a twenty-third embodiment of this invention there is provided a system for determining ozone concentration in air which system comprises:
(A) a nitric oxide analyser to determine the nitric oxide concentration of the air;
(B) a $NO_y$ analyser to determine the $NO_y$ concentration of the air;
(C) the system of the fifteenth embodiment for determining the concentration of smog in the air; and
(D) calculating means operatively associated with the nitric oxide analyser of (A) the $NO_y$ analyser of (B) and the system of (C) to calculate the ozone concentration from the nitric oxide concentration, $NO_y$ concentration and smog concentration of the air.

Preferably the nitric oxide analyser of (A) and the $NO_y$ analyser of (B) are the same nitric oxide and $NO_y$ analysers of the system of (C).

According to a twenty-fourth embodiment of this invention there is provided a system for determining nitric oxide and $NO_y$ or ozone or both concentrations in air which system comprises:
(A) a light sensor to determine the sunlight intensity of the air;
(B) a temperature sensor to determine the temperature of the air;
(C) an $NO_y$ analyser to determine the $NO_y$ concentration of the air;
(D) the system of the fifteenth embodiment to determine the smog concentration of the air; and
(E) calculating means operatively associated with the light and temperature sensors and the $NO_y$ analyser and smog concentration measurement systems the calculating means to calculate the nitric oxide and ozone concentrations of the air from the sunlight intensity, air temperature and the $NO_y$ and smog concentrations.

Preferably the $NO_y$ analyser of (C) is the same $NO_y$ analyser of the system (D).

According to a twenty-fifth embodiment of this invention there is provided a method for determining ROC concentration of air and/or a method for determining total concentration of prior ROC emissions into air, which method comprises:
(a) adding excess nitric oxide to the air to provide an excess nitric oxide/air mixture;
(b) permitting the mixture to react for a first selected period wherein excess nitric oxide in the mixture reacts with substantially all ozone in the mixture;
(c) determining a first nitric oxide concentration of the mixture after the first selected period;
(d) illuminating the mixture of (a) or the mixture after the first selected period for a second selected period under known temperature and illumination conditions;
(e) permitting the mixture, after illumination, to react for a third selected period wherein excess nitric oxide in the mixture reacts with any ozone present in the mixture;

(f) determining a second nitric oxide concentration of the mixture after the third selected period; and (g) determining the ROC concentration of air, and/or determining the total concentration of prior ROC emissions into the air, from the first and second nitric oxide concentrations According to a twenty-sixth embodiment of this invention there is provided a system for determining ROC concentration of air and/or total concentration of prior ROC emissions into air, which system comprises:

(a) a combiner for combining excess nitric oxide with the air to provide an excess nitric oxide/air mixture;

(b) a first reactor operatively associated with the combiner wherein the mixture can react in the first reactor for a first selected period wherein excess nitric oxide in the mixture reacts with substantially all ozone in the mixture;

(c) a photoreactor operatively associated with the combiner and optionally the first reactor;

(d) an illumination source operatively disposed about the photoreactor to illuminate the mixture of (a), in the photoreactor, or the mixture after the first selected period, in the photoreactor for a second selected period under selected temperature and illumination conditions;

(e) a second reactor operatively associated with the photoreactor wherein the mixture can in the second reactor react for a third selected period wherein excess nitric oxide in the mixture reacts with substantially all ozone in the mixture;

(f) a nitric oxide analyser operatively associated with the first reactor to determine a first nitric oxide concentration of the mixture after the first selected period and operatively associated with the second reactor to determine a second nitric oxide concentration of the mixture after the third selected period; and (g) calculating means operatively associated with the nitric oxide analyser to calculate the ROC concentration of air, and/or total concentration of prior ROC emissions into air, from the first and second nitric oxide concentrations.

According to a further embodiment of this invention there is provided a method of locating a source of Reactive Organic Compounds (ROC) present in air, the method comprising:

(α) determining a time period during which smog formation in the air has occurred, the time period being substantially the same as or within a predetermined period for which the illumination and temperature conditions are known, wherein the end of the predetermined period coincides with the end of the time period by:

(A) determining temperatures of the air for the predetermined period;

(B) determining sunlight intensities for the predetermined period;

(C) determining the rate coefficient of smog formation in the air by the method described herein;

(D) determining the amount of prior smog formation in the air at the end of the time period by:

(I) determining $NO_y$ concentration in the air;

(II) determining the concentration of smog in the air by:

(II)(i) adding excess nitric oxide to the air to provide an excess nitric oxide/air mixture;

(II)(ii) reacting the mixture for a selected period wherein the excess nitric oxide reacts with substantially all ozone in the mixture;

(II)(iii) determining the nitric oxide concentration of the mixture after the selected period;

(II)(iv) determining the total oxidized nitrogen ($NO_y$) concentration of the mixture after the selected period; and (II)(v) determining the concentration of smog formation from the nitric oxide concentration of (II)(iii) and the $NO_y$ concentration of (II)(iv).

(III) determining the concentration of total nitrogen oxides previously emitted into the air from the $NO_y$ concentration in the air and the concentration of smog in the air; and (IV) determining the amount of prior smog formation in the air from the concentration of total nitrogen oxides previously emitted into the air as determined in step (III) and the concentration of smog in the air as determined in (II); and (E) determining the time period during which the smog formation in the air has occurred from the amount of prior smog formation, the rate coefficient, and the determined temperatures and sunlight intensities; and (β) determining speed of movement and trajectory in the air during the time period; and (γ) locating said source of ROC from said time period and said speed and trajectory in the air over said time period.

According to a still further embodiment of this invention there is provided a method for determining the current extent of smog formation in air, which method comprises the steps of:

(I) determining maximum potential smog formation in air by the method of the fifth embodiment; and (II) calculating the extent of smog formation in air as the ratio of the concentration of smog in air to the maximum potential concentration of smog in air.

The temperature of the mixture can be kept constant during illumination, can be allowed to vary and optionally monitored or the temperature of the mixture can be varied according to a preselected or selected temperature profile. Thus, it is preferred that a temperature controller/programmer is operatively associated with the photoreactors of the thirteenth, fourteenth, eighteenth, nineteenth and twenty-sixth embodiments.

The illumination can be kept constant or can be varied according to a preselected or selected illumination profile. It is therefore preferred that an illuminator controller/programmer is operatively associated with and coupled with the illumination sources of the thirteen, fourteenth, eighteenth, nineteenth and twenty-sixth embodiments.

Preferred illumination sources provide an actinic flux of similar intensity and spectral distribution to sunlight at about noon on a clear day. It may be adequate for the purpose, however, to approximate the solar spectrum by only the "UVA" part of the total wavelength band.

Illumination may be provided by a single type of lamp or various lamp type and filter combinations. For example, actinic UV fluorescent tubes are suitable as is a high pressure xenon arc and pyrex glass filter combination. The preferred illumination intensity is that which yields a rate coefficient for the photodissociation of nitrogen dioxide ($NO_2 + h\nu \rightarrow NO + O$) of $\sim 0.4$ min$^{-1}$. However intensities which depart markedly from this value are viable. Times preferred for the first and third reaction periods are of tile order of a few minutes, which is sufficient for the reaction of nitric oxide with ozone to be substantially complete. The preferred time for the second selected period is about 10 minutes or so long as is required to produce measurable consumption of nitric oxide in air containing significant quantity of ROC.

The systems of the thirteenth, fourteenth, fifteenth, sixteenth, seventeenth, eighteenth, nineteenth and twenty-sixth embodiments optionally include first metered delivery means to deliver metered doses of air to the combiner and includes second metered delivery means to deliver metered doses of nitric oxide to the combiner.

The fourteenth and nineteenth embodiments optionally include third metered delivery means to deliver metered doses of ozone to the combiner and ozone filter to filter ozone prior to injection into the combiner.

Optionally the systems of the thirteenth, fourteenth, fifteenth, sixteenth, seventeenth, eighteenth, nineteenth and twenty-sixth embodiments include an air filter to filter air prior to injection into the combiner and a nitric oxide filter to filter nitric oxide prior to injection into the combiner.

It is preferred that the photoreactor is constructed from material that is transparent to illumination and is chemically unreactive. FEP teflon film is an example of material which is suitable for this purpose.

FEP teflon film has the advantages that it is chemically unreactive and is transparent to ultraviolet light and is available in thin but robust film form.

The concentration of nitric oxide excess in the nitric oxide/air mixture or ozone excess in the ozone/air mixture is typically in the range about 0.05 to about 1 ppm (mole fraction) but the upper range limit should not be of a concentration which induces reactions to occur in the mixture which result in a significant change in the nature of the chemistry of the mixture. For example, a large excess of nitric oxide can cause a reduction in the hydroxyl radical concentration of the photoreactor, resulting in a reduction in the rate of nitric oxide consumption in the photoreactor. The lower range limit should be sufficient to provide for complete reaction of the ozone or nitric oxide of the air with the excess nitric oxide or ozone respectively. More typically the range is about 0.05 to about 0.3 ppm and even more typically about 0.05 to about 0.15 ppm. Preferably the concentration is about 0.1 ppm.

GENERAL DESCRIPTION OF THE METHOD OF CALCULATION

Whilst photochemical smog formation is the result of some several hundred or more elementary reaction steps in the light of the present inventor's finding that the amount of smog formed in air and the smog concentration in air can be determined by the oxidation of NO, the overall reactions of smog formation can be described by the following representative expressions:

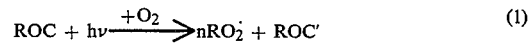

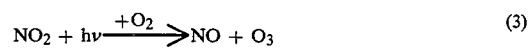

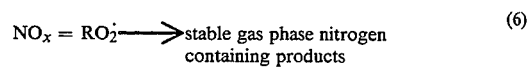

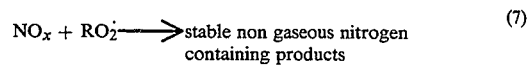

where $RO_2^\cdot$ denotes hydroxyl, alkoxy and peroxy free radical species, ROC and ROC' are "reactive organic compounds" including carbonyl, alkane, alkene, aromatic, carbon monoxide and other types of gas phase carbonaceous species which when present and illuminated in air undergo reactions whereby oxygen is consumed and NO is oxidized, $NO_x$ denotes NO and $NO_2$ and n is a proportionality coefficient.

Providing there is sufficient illumination, reactions (2), (3) and (4) continue until the NO concentration is reduced to such a level that there is insufficient NO available to freely maintain reaction (2) and smog formation is curtailed. In addition to $RO_2^\cdot$ reaction with NO, free radicals produced by reaction (1) may also undergo radical-radical recombination via reaction (5). During smog formation ROC molecules may cycle through reaction (1) several times. Although the constituent species of ROC are changed by participation in the reactions, to a good approximation for air of ROC composition as usually found in urban regions, the rate coefficient for reaction (1) remains surprisingly constant, independently of the extent of reaction and at least for illumination intensities and durations equivalent to the sunlight of an unclouded summer's day.

Nitric oxide undergoes reaction with free radical species via reactions (2), (6) and (7). However in general the rate of NO reaction via (2) is much greater than the rate of NO reaction via (6) and (7). For many purposes NO reaction by (6) and (7) can be neglected.

Reaction of NO in accordance with reactions (2), (6) and (7) is a measure of smog formation. The rate of NO consumption by these reactions is a measure of the rate of smog formation while the concentration of NO so consumed is a measure of the smog concentration.

In illuminated air NO consumed by reaction (2) can be regenerated by reaction (3), producing moles of $O_3$ equivalent to the NO regenerated. By the addition of excess NO to air, $O_3$ is reacted according to reaction (4) with the consumption of equivalent NO.

The moles of smog formed in air up to time t, ($^f n_{smog}{}^t$), that is the number of moles of NO consumed by reaction (2), is determined as being equal to the total number of moles of NO emitted into the air ($^o n_{NO}{}^t$) up to time t plus moles of excess nitric oxide added during analysis ($^{added}n_{NO}$) less the moles of nitric oxide remaining after completion of reaction (4) in the analysis system ($^{I}n_{NO}$):

$$f_{n_{smog}}{}^{t} = {}^{o}n_{NO}{}^{t} + {}^{added}n_{NO} - {}^{I}n_{NO} \qquad (8)$$

While there are many nitrogenous species known to be present in air and constituting $NO_y$ it is usual for $NO_y$ to be emitted into the air in only two forms, namely NO and $NO_2$ and these emissions together are commonly denoted as $NO_x$:

$$NO_x = NO + NO_2. \qquad (9)$$

Furthermore, the bulk of all anthropogenic $NO_x$ emissions are in the form of NO. The fraction of NO in $NO_x$ emissions ($^{o}F_{NO}$) can vary with the specific type of $NO_x$ emission source (e.g. the burnt gases from furnaces, motor vehicles, domestic heating) but commonly falls within the range 0.6 to 1.0. For urban atmospheres the value of $^{o}F_{NO}$ is frequently in the range of 0.7 to 0.95. However, $^{o}F_{NO}$ can be determined explicitly by measurement of the NO/$NO_x$ composition of the $NO_x$ emissions at their source.

Thus the NO emitted into the air can be determined as a function of the emission of $NO_y$ into the air, since for emissions:

$$^{o}n_{NO}{}^{t}{}_{y} = {}^{o}n_{NO}{}^{t}{}_{x} \qquad (10)$$

hence $$^{o}n_{NO}{}^{t} = {}^{o}F_{NO}{}^{o}n_{NO_y}{}^{t} \qquad (11)$$

and to a fair approximation $^{o}F_{NO}$ has the value of 0.9.

NOTE: For some purposes it is sufficiently accurate to employ the value 1 for $^{o}F_{NO}$, in which case:

$$^{o}n_{NO}{}^{t} \approx {}^{o}n_{NO_y}{}^{t} \qquad (12)$$

During smog formation some $NO_y$ is lost from the air by reaction (7), some $NO_y$ being incorporated into non-gaseous nitrogenous species, thus the $NO_y$ content of the air at time t, ($n_{NO_y}{}^{t}$) after significant t smog forming reaction has taken place, may be less than the amount of $NO_y$ emitted into the air ($^{o}n_{NO_y}{}^{t}$). The rate of $NO_y$ loss from the air is slow compared to the rate of smog formation and so for many purposes the $NO_y$ loss is relatively small and can be neglected, i.e.:

$$^{o}n_{NO_y}{}^{t} \approx n_{NO_y}{}^{t} \qquad (13)$$

In daylight and for air with compositions as commonly found in urban regions, reaction (7) proceeds at a rate ($R_7$) and which is a function of the rate of reaction (2), ($R_2$):

$$R_7 = f(R_2) \qquad (14)$$

To a good approximation the form of the function $f(R_2)$ is one of direct proportion:

$$R_7 = P_{7,2} R_2 \qquad (15)$$

where $P_{7,2}$ is the proportionality coefficient. A typical value for $P_{7,2}$ is determined by the inventor to be 0.125. Thus optionally (15) and the measured value of $n_{NO_y}{}^{t}$ may be used to obtain a more accurate estimate of $^{o}n_{NO_y}{}^{t}$ in place of (13).

The concentration of smog in air is a function of: the rate of smog formation, the pre-existing smog concentration, the dispersion and dilution of the air by meteorological processes and the loss of smog from the air by the deposition of ozone and $NO_y$ species, incorporation of $NO_y$ into particulate materials and other loss processes.

Defining smog concentration to be the sum of the concentrations of the gaseous oxidized nitrogen species, plus the ozone concentration, less the concentration of nitric oxide, the smog concentration of air at time t, $\chi_{smog}{}^{t}$ is determined by the method of the third embodiment and by means of the system of the fifteenth embodiment, namely from the NO concentration of the mixture after the selected period of the third embodiment, step (c) ($^{I}\chi_{NO}$) and the total oxidized nitrogen concentration of the mixture at step (d), ($^{I}\chi_{NO_y}$), by the equation:

$$\chi_{smog}{}^{t} = {}^{I}\chi_{NO_y} - {}^{I}\chi_{NO} \qquad (16)$$

Defining the amount of smog formation in volume $V^{t}$ of air at time t, ($f_{n_{smog}}{}^{t}$), to be the number of moles of NO previously consumed by reaction (2), (6) and (7) $f_{n_{smog}}{}^{t}$, is given by equation (17):

$$f_{n_{smog}}{}^{t} = {}^{o}n_{NO}{}^{t} + n_{O_3}{}^{t} - n_{NO}{}^{t} \qquad (17)$$

and from (10) and (11):

$$^{o}n_{NO}{}^{t} = {}^{o}F_{NO}{}^{o}n_{NO_y}{}^{t} \qquad (18)$$

and from (15), correcting the $NO_y$ content of air for loss of $NO_y$ from the air by reaction (7):

$$^{o}n_{NO_y}{}^{t} = n_{NO_y}{}^{t} + P_{7,2} f_{n_{smog}}{}^{t} \qquad (19)$$

Substituting (19) for $^{o}n_{NO_y}{}^{t}$ in (18)

$$^{o}n_{NO}{}^{t} = {}^{o}F_{NO}(n_{NO_y}{}^{t} + P_{7,2} f_{n_{smog}}{}^{t}) \qquad (20)$$

Substituting (20) in (17) and rearranging $$f_{n_{smog}}{}^{t} = ({}^{o}F_{NO} n_{NO_y}{}^{t} + n_{O_3}{}^{t} - n_{NO}{}^{t})/(1 - {}^{o}F_{NO} P_{7,2}) \qquad (21)$$

Now in the presence of excess added NO($^{added}n_{NO}$) and after reaction in darkness for a selected period such that reaction (4) is complete $$^{o}F_{NO} n_{NO_y}{}^{t} + n_{O_3}{}^{t} - n_{NO}{}^{t} = {}^{o}F_{NO} n_{NO_y}{}^{t} + {}^{added}n_{NO} - {}^{I}n_{NO}{}^{t} \qquad (22)$$

now the amount of $NO_y$ present after the selected period ($^{I}n_{NO_y}$) and addition of excess NO is given by:

$$^{I}n_{NO_y} = n_{NO_y}{}^{t} + {}^{added}n_{NO} \qquad (23)$$

hence $$^oF_{NO}n_{NO_y}{}^t + {}^{added}n_{NO} = {}^In_{NO_y} - (1 - {}^oF_{NO})n_{NO_y}{}^t \quad (24)$$

substituting (24) into (22):

$$^oF_{NO}n_{NO_y}{}^t + n_{O_3}{}^t - n_{NO}{}^t = {}^In_{NO_y} - (1 - {}^oF_{NO})n_{NO_y}{}^t - {}^In_{NO} \quad (25)$$

and substituting (25) into (21):

$$^fn_{smog}{}^t = [{}^In_{NO_y} - {}^In_{NO} - (1 - {}^oF_{NO})n_{NO_y}{}^t]/[1 - {}^oF_{NO}P_{7,2}] \quad (26)$$

Now Dalton's Law states for ideal gases, concentration (mole fraction) of species i at time t ($\chi_i{}^t$) is given by:

$$\chi_i{}^t = n_i{}^t R T^t / P^t V^t \quad (27)$$

where R is the gas constant and $T^t$, $P^t$ and $V^t$ are the temperature pressure and volume of the gas respectively at time t. Multiplying throughout (26) by $RT^t/P^tV^t$ and substituting (27):

$$^f\chi_{smog}{}^t = [{}^I\chi_{NO_y} - {}^I\chi_{NO} - (1 - {}^oF_{NO})\chi_{NO_y}{}^t]/[1 - {}^oF_{NO}P_{7,2}] \quad (25)$$

for:

$$^f\chi_{smog}{}^t < {}^{fmax}\chi_{smog}$$

where $^f\chi_{smog}{}^t$ denotes the concentration of smog that would be present in the absence of $NO_y$ loss from the air by reaction (7).

Equation (28) is valid for values of $^f\chi_{smog}{}^t$ less than the maximum potential smog formation ($^{fmax}\chi_{smog}{}^t$) but after the smog maximum has been reached $NO_y$ loss processes continue and new smog is not formed. In this circumstance $P_{7,2}$ can no longer be approximated by a value of 0.125. Now:

$$\chi_{smog}{}^t = {}^I\chi_{NO_y} - {}^I\chi_{NO} \quad (16)$$

Substituting (16) into (28):

$$^f\chi_{smog}{}^t[\chi_{smog}{}^t - (1 - {}^oF_{NO})\chi_{NO_y}{}^t]/[1 - {}^oF_{NO}P_{7,2}] \quad (29)$$

for:

$$^f\chi_{smog}{}^t < {}^{fmax}\chi_{smog}{}^t$$

Optionally, the approximations:

$$^oF_{NO} \approx 1$$

and $$P_{7,2} \approx 0$$

can be made, then (29) yields:

$$\chi_{smog}{}^t \approx {}^f\chi_{smog}{}^t \quad (30)$$

Summarizing, the smog concentration in air ($\chi_{smog}{}^t$) is determined by the system of the fifteenth embodiment and the method of the third embodiment and calculated from equation (16), i.e.

$$\chi_{smog}{}^t = {}^I\chi_{NO_y} - {}^I\chi_{NO} \quad (16)$$

The $NO_y$ concentration of the air may also be measured as per the fourth and sixteenth embodiments and the smog formation expressed as the notional concentration of smog formed in air in the absence of smog removal processes ($^f\chi_{smog}{}^t$) as calculated by equation (29):

$$^f\chi_{smog}{}^t = [\chi_{smog}{}^t - (1 - {}^oF_{NO})\chi_{NO_y}{}^t]/(1 - {}^oF_{NO}P_{7,2}) \quad (29)$$

for:

$$^f\chi_{smog}{}^t < {}^{fmax}\chi_{smog}{}^t$$

where for most circumstances $$^oF_{NO} = 0.9$$

and $$P_{7,2} = 0.125$$

and $$P_{7,2} = 0.125$$

The maximum potential smog formation in air is controlled by the rate of reaction (2) relative to the combined rates of reactions (6) and (7). When reactions (6) and (7) have consumed $NO_2$ such that reaction (3) cannot regenerate NO in sufficient concentration to maintain reaction (2) smog formation is curtailed and new smog production eventually ceases. Thus to a fair approximation the maximum potential smog formation in air ($^{fmax}\chi_{smog}{}^t$ and $^{fmax}n_{smog}{}^t$) is given by:

$$^{fmax}\chi_{smog}{}^t = \beta^o\chi_{NO_y}{}^t \quad (31)$$

$$^{fmax}n_{smog}{}^t = \beta^o n_{NO_y}{}^t \quad (32)$$

where the function B is dependent on the rate of reaction (2) relative to the combined rates of reactions (6) and (7) and for air of compositions commonly found in urban areas can be approximated by the value B: 4.

Substituting expressions (19) and (27) into equation (31) and rearranging yields expression for maximum potential concentration of smog formed in air in terms of the observables $\chi_{NO_y}{}^t$ and $^f\chi_{smog}{}^t$ where $^f\chi_{smog}{}^t$ is given by equation (29):

$$^{fmax}\chi_{smog}{}^t = \beta(\chi_{NO_y}{}^t + P_{7,2}{}^f\chi_{smog}{}^t) \quad (33)$$

when $$(^f\chi_{smog}{}^t < {}^{fmax}\chi_{smog}{}^t)$$

The total maximum potential concentration of smog ($^{Tmax}\chi_{smog}{}^t$) in air is defined as the sum of the concentrations of smog formed in air by smog formation processes plus the concentration of smog emitted into air as $NO_2$:

$$^{Tmax}\chi_{smog}{}^t = {}^{fmax}\chi_{smog}{}^t + {}^o\chi_{NO_2}{}^t \quad (115)$$

where $^o\chi_{NO_2}{}^t$ is the concentration of $NO_2$ emissions into air.

Now from equations (9), (10), (11) and (27)

$$^o\chi_{NO2}{}^t = (1 - {}^oF_{NO}){}^o\chi_{NOy}{}^t \quad (116)$$

substituting (116) into (115)

$$T_{max}\chi_{smog}{}^t = f_{max}\chi_{smog}{}^t + (1 - {}^oF_{NO}){}^o\chi_{NOy}{}^t \quad (117)$$

and substituting (31) into (117) gives $$T_{max}\chi_{smog}{}^t = {}^o\chi_{NOy}{}^t(\beta + 1 - {}^oF_{NO}) \quad (118)$$

By equations (19) and (27) equation (118) can be expressed as $$T_{max}\chi_{smog}{}^t = (\beta + 1 - {}^oF_{NO})(\chi_{NOy}{}^t + P_{7,2}{}^f\chi_{smog}{}^t) \quad (119)$$

when $$(^f\chi_{smog}{}^t < {}^{fmax}\chi_{smog}{}^t)$$

where $^f\chi_{smog}{}^t$ is given by equation (29).

The extent of smog formation at time t, ($E_{smog}{}^t$), is given by:

$$E_{smog}{}^t \leq (^fn_{smog}{}^t/{}^{fmax}n_{smog}{}^t) \quad (34)$$

and $$E_{smog}{}^t = (^f\chi_{smog}{}^t/{}^{fmax}\chi_{smog}{}^t) \quad (35)$$

Rate of smog formation at selected temperature (T) and illumination intensity (I) ($^{T,I}Q_{smog}{}^t$) in the presence of excess NO is given by:

$$^{T,I}Q_{smog}{}^t = (^I\chi_{NO} - {}^{III}\chi_{NO})/{}^{II}t \quad (36)$$

where $^{III}\chi_{NO}$ and $^I\chi_{NO}$ are the concentrations of NO after the third and first selected periods and $^{II}t$ is the duration of the second selected period of embodiments six and eighteen. The rate $^{T,I}Q_{smog}{}^t$ corresponds to the rate of NO consumption by reactions (2), (6) and (7).

The $NO_2$ produced by reaction (2) can react further via reaction (3) and smog formation is then exhibited as ozone production. When excess ozone is present the steady state NO concentration maintained by reactions (3) and (4) is small and then to a good approximation the increase in ozone concentration resulting from smog formation is quantitatively equal to the NO consumed by reaction (2) less the $NO_x$ consumed by reactions (6) and (7). In this circumstance the rate of smog formation is given by:

$$^{T,I}A_{smog}{}^t = (^I\chi_{O3} - {}^{III}\chi_{O3})/(^{II}t\{1 - 1/\beta\}) \quad (37)$$

where $^{III}\chi_{O3}$ and $^I\chi_{O3}$ are the concentrations of ozone after the third and first selected period and $^{II}t$ is the duration of the second period of embodiments seven and nineteen and G is a term to account for the $NO_x$ consumed by reactions (6) and (7). Typically a suitable value for $\beta$ is $\beta = 4$.

Rate coefficient for smog formation $R_{smog}{}^t$ is given by:

$$R_{smog}{}^t = {}^{T,I}Q_{smog}{}^t / I^t f(T^t) \quad (38)$$

where $I^t$ and $T^t$ are the illumination intensity and temperature during the second selected period of embodiments one or two or thirteen or fourteen. $f(T^t)$ is a function of temperature and $^{T,I}Q_{smog}{}^t$ is obtained by the method of the first or second embodiments and the system of the thirteenth or fourteenth embodiments and equations (36) or (37) respectively, and the function $f(T^t)$ can be adequately approximated by the expression:

$$f(T^t) = e^{-1000\gamma(1/T^t - 1/316)} \quad (39)$$

where y has the value of 4.7 and T is temperature in degrees Kelvin.

Alternatively, $f(T^t)$ may be evaluated by measurement of $^{T,I}Q_{smog}{}^t$ over a range of temperatures. The value of $R_{smog}{}^t$ is dependent on the concentration and properties of the ROC content of air and:

$$R_{smog}^t = \sum_{i=1}^{n} a_{ROC(i)} \chi_{ROC(i)}^t \quad (40)$$

and $$R_{smog}^t = (RT^t/P^tV^t) \sum_{i=1}^{n} a_{ROC(i)} \, {}^on_{ROC(i)}^t \quad (41)$$

where $a_{ROC(i)}$ is an activity coefficient for smog formation by ROC(i) and wherein ROC(i) can be an individual ROC or a mixture of various ROC's. Smog formation is described by the equations:

$$f_{n_{smog}}^t = (P^tV^t/RT^t) \int_0^t {}^{T,I}Q_{smog}^t \cdot dt \quad (42)$$

where $$^{T,I}Q_{smog}{}^t = R_{smog}{}^t I^t f(T^t) \quad (43)$$

where $$(^f\chi_{smog}{}^t < \beta^o\chi_{NOy}{}^t)$$

or $$^{T,I}Q_{smog}{}^t = 0 (^f\chi_{smog}{}^t \nless \beta^o\chi_{NOy}{}^t)$$

Time required for selected amount of smog formation, for example: time for maximum smog formation, embodiments 8 and 20; time period during which smog formation has occurred, embodiments 9 and 21; or time required for production of a given amount of smog in air, embodiments 10 and 22, may be calculated for selected or measured $I^t$ and $T^t$ via equations (39), (42) and (43).

The ozone concentration of air is given by:

$$\chi_{O_e}{}^t = \chi_{smog}{}^t + \chi_{NO}{}^t - \chi_{NOy}{}^t \quad (44)$$

where smog concentration $\chi_{smog}{}^t$ and nitric oxide concentration $\chi_{NO}{}^t$ and the $NO_y$ concentration $\chi_{NOy}{}^t$ are determined by the method of the eleventh embodiment and the system of the twenty third embodiment.

When air is illuminated the concentrations of ozone and nitric oxide in the air are interrelated and dependent on the intensity of light. According to reactions (3) and (4):

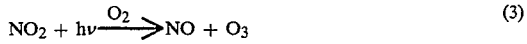

$$NO_2 + h\nu \xrightarrow{O_2} NO + O_3 \quad (3)$$

and

$$NO + O_3 \rightarrow NO_2 \quad (4)$$

when air is illuminated there is rapid exchange of oxygen atoms between $NO_2$ and $O_3$. In sunlight the rates of reactions (3) and (4) are much faster than the rates of reactions (2) (6) and (7). Thus the rates of reactions (3) and (4) are approximately equal, i.e.:

$$k_e^t \chi_{NO_2}^t = k_4^t \chi_{NO}^t \chi_{O_3}^t \quad (64)$$

where $K_3^t$ and $K_4^t$ are the rate coefficients at t%me t for t reactions (3) and (4) respectively and $k_3^t$ incorporates the illumination intensity. For ambient air, the sunlight intensity is usually sufficiently steady for equation (64) to be valid.

From equation (64) and by definition of $NO_x$ (equation (9))

$$\chi_{O_3}^t = (\chi_{NO_x}^t - \chi_{NO}^t) k_3^t / k_r^t \chi_{NO}^t \quad (124)$$

Substituting (124) into equation (44) and rearranging gives $$(\chi_{NO}^t)^2 - (\chi_{NO_y}^t - \chi_{smog}^t - k_e^t / k_r^t) \chi_{NO}^t - k_3^t \chi_{NO_x}^t / k_4^t = 0 \quad (125)$$

By an analogous argument an expression for $\chi_{O_3}^t$ can also be derived:

$$k_r^t (\chi_{O_3}^t)^2 + (k_3^t - k_4^t \chi_{smog}^t + k_4^t \chi_{NO_y}^t) \chi_{O_3}^t + k_3 (\chi_{NO_y}^t - \chi_{smog}^t - \chi_{NO_x}^t) = 0 \quad (126)$$

Experimental observation of smog formation under natural sunlight conditions and concentrations simulating ambient air shows that when $f\chi_{smog}^t$ falls outside the range:

$$(^0\chi_{NO}^t - H^0 \chi_{NO_y}^t) < f\chi_{smog}^t < (^0\chi_{NO}^t + L^0 \chi_{NO_y}^t) \quad (70)$$

where appropriate values for coefficients H and L are $H = L = \frac{1}{2}$ then the terms involving $k_3$ of equations (125) and (126) have only a small influence on the values of $\chi_{NO}^t$ and $\chi_{O_3}^t$, as is also the case in darkness (i.e. $k_3^t = 0$). In these cases equation 25 simplifies to $$\chi_{NO}^t = \chi_{NO_y}^t - \chi_{smog}^t (\chi_{smog}^t < \chi_{NO_y}^t)$$

or $$\chi_{NO}^t = 0 (\chi_{smog}^t \geq \chi_{NO_y}^t) \quad (68)$$

and equation 126 simplifies to $$\chi_{O_3}^t = 0 (\chi_{smog}^t \leq \chi_{NO_y}^t)$$

or $$\chi_{O_3}^t = \chi_{smog}^t - \chi_{NO_y}^t (\chi_{smog}^t < \chi_{NO_y}^t) \quad (69)$$

When $f\chi_{smog}^t$ falls within the domain given by (70) and $k_3^t \neq 0$ then experimental study of smog formation under conditions pertinent to ambient air demonstrates that $$\chi_{NO_y}^t \approx \chi_{NO_x}^t \quad (71)$$

(when $f\chi_{smog}^t$ is in the (domain given by expression (70)).

Then substitution of $\chi_{NO_y}^t$ for $\chi_{NO_x}^t$ in equations (125) and (126) is appropriate and, taking the value of $k_4$ from the literature, enables the values of $\chi_{NO}^t$ and $\chi_{O_3}^t$ to be evaluated.

Thus from measurements according to the method of embodiment twelve and the system of embodiment twenty-four and equations (68), (69), (71), (125) and (126) the ozone and nitric oxide concentrations of the air are determined.

BRIEF DESCRIPTION OF DRAWINGS

Preferred embodiments of the systems and methods of this invention are described below with reference to the following drawings in which.

BEST MODE AND OTHER MODES FOR CARRYING OUT THE INVENTION

Figure 1:
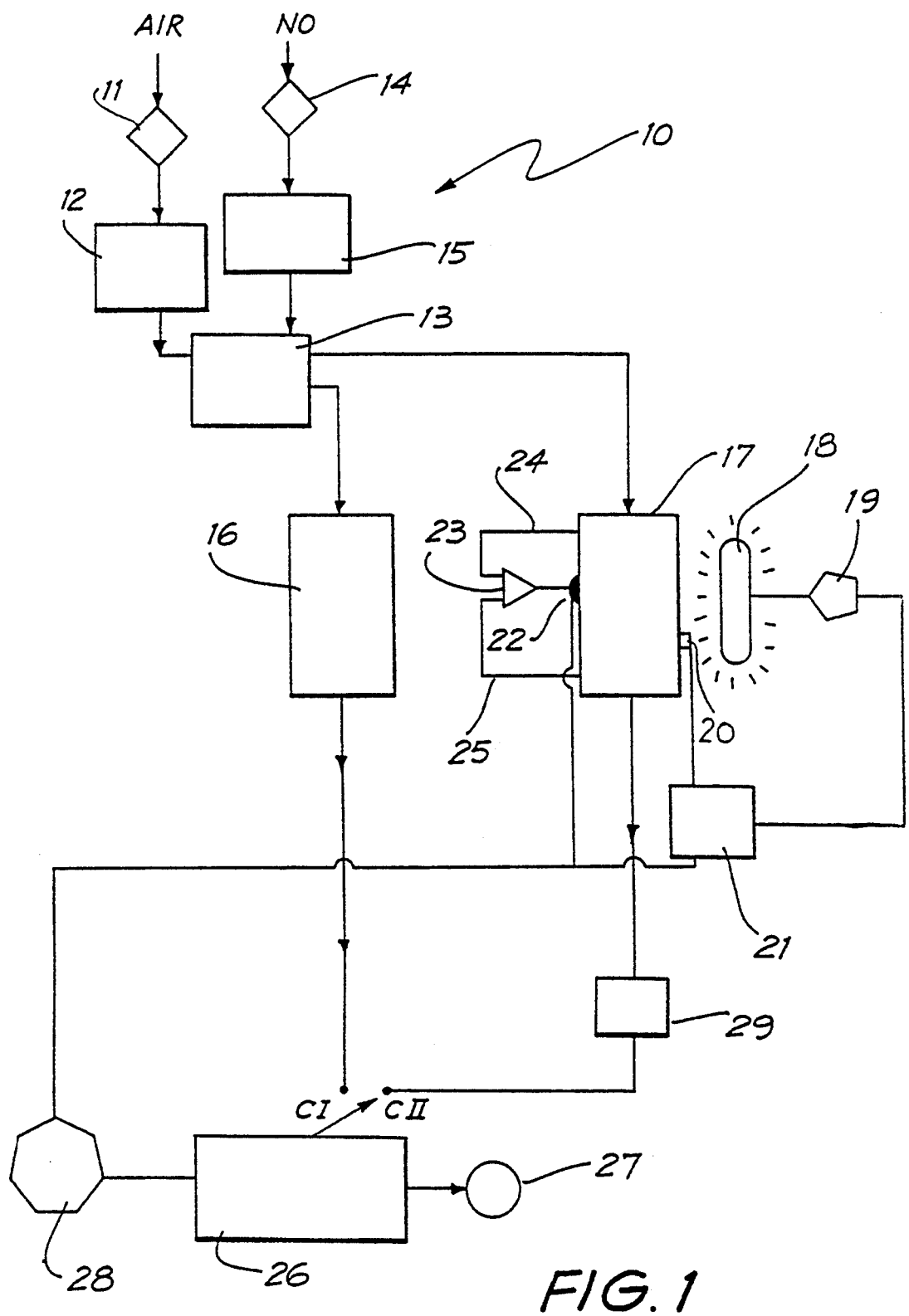
FIG. 1 is a block diagram of a system for determining rate coefficient of smog formation in FIG. 2 is a block diagram of a system for determining concentration of smog in air.

Referring to FIG. 1 a system 10 for determining rate coefficient of smog formation in air includes an air filter II which filters incoming air and a metered delivery injector 12 which delivers a metered dose of the filtered air to combiner 13. A metered dosage of excess nitric oxide is combined with the filtered air in combiner 13 after passing through nitric oxide filter 14 and being injected therein by metered delivery injector 15. As a result an excess nitric oxide/air mixture is formed in combiner 13 and dispensed via two separate streams. The concentration of nitric oxide at injector 15 is typically a high concentration so that the volume of mixture produced by combiner 13 is close to the volume of air from which it is generated, i.e. so that the volume of nitric oxide required to produce the excess nitric oxide/air mixture is small compared to the volume of air to which it is added and thus the volume of nitric oxide added can be neglected for computational purposes.

Reactor 16 in which the mixture can react for a first selected period wherein excess nitric oxide in the mixture reacts with substantially all ozone in the mixture is operatively coupled to combiner 13.

Photoreactor 17 is also operatively coupled to combiner 13. Illumination source 18 is operatively disposed, about photoreactor 17 to illuminate the mixture in photoreactor 17 for a second selected period under known temperature and illumination conditions. Illumination from source 18 can be kept constant or can be varied according to a preselected or selected illumination profile. Illumination controller/programmer 19 is operatively coupled to source 18 and an illumination sensor consisting of photodiode 20 and photometer 21 for this latter purpose.

Temperature sensor 22 is operatively coupled to photoreactor 17 and temperature controller/programmer 23 to determine the temperature of the mixture in photoreactor 17. The temperature of the mixture in photoreactor 17 can be kept constant during illumination or can be allowed to vary and monitored or can be varied according to a preselected or selected temperature profile by temperature controller/programmer 23 which is operatively coupled to photoreactor 17 via lines 24 and 25. A reactor 29 in which during a third selected period excess nitric oxide of the mixture reacts with substantially all ozone is operatively coupled to photoreactor 17.

Nitric oxide analyser 26 is operatively coupled to reactor 16 to determine a first nitric oxide concentration of the mixture after the first selected period at point CI and operatively coupled to reactor 29 to determine a second nitric oxide concentration of the mixture after the third selected period at point CII. The mixture is vented from the system via analyser 26 and vent 27. Computer 28 is operatively coupled to temperature sensor 22, photometer 21 and analyser 26 to calculate the rate coefficient from the first and second nitric oxide concentrations, the known temperature and illumination conditions and the duration of the second selected period.

Typically reactor 16 is of similar form and volume as the combination of the reaction vessels of photoreactor 17 and reactor 29 and the residence time for the mixture to pass from combiner 13 to CI is the same as the time required to pass from combiner 13 to CII. By this means the mixtures available at CI and CII have a common origin at combiner 13. Thus, when the composition of air entering filter 11 has components of rapidly varying concentration the mixtures at CI and CII have a common origin from air of identical compositions.

The rate coefficient of smog formation in air can be determined in The following manner. A metered amount of air is delivered to combiner 13, after passing through filter 11 and injector 12. Excess nitric oxide is added to the air in combiner 13, after passing through filter 14, and injector 15 to provide an excess nitric oxide/air mixture in combiner 13. The mixture is transferred to reactor 16 and photoreactor 17. The mixture is permitted to react in reactor 16 for a first selected period wherein excess nitric oxide in the mixture reacts with substantially all ozone the mixture. A first nitric oxide concentration of the mixture is then measured by analyser 26 at point CI.

The mixture is illuminated in photoreactor 17 for a second selected period under selected and known temperature and illumination conditions. After illumination the mixture is permitted to react for a third selected period in reactor 29. A second nitric oxide concentration of the mixture is measured after the third selected period at point CII by analyser 26. Preferably the duration of the first period is equal to the total duration of the second and third periods. The rate coefficient is then calculated by computer 28 from the first and second nitric oxide concentrations, $^I\chi_{NO}$ and $^{III}\chi_{NO}$ respectively, the known temperature (T) and illumination conditions (I) and the duration of the second selected period ($^{II}t$) and where the rate of smog formation is defined as the consumption of nitric oxide per unit time by reaction (2):

$$RO_2^* + NO \rightarrow NO_2 \qquad (2)$$

where $NO_2$ denotes predominantly nitrogen dioxide but also organic nitrates and other trace nitrogenous products.

Firstly the rate of smog formation ($^{T,I}Q_{smog}^t$) in photoreactor 17 is calculated according to equation (36)and corrected for dilution of $=[([I_x \text{air by mixing with added nitric oxide by the expression:}$ $$^{T,I}Q_{smog}{}^t = [(({}^I\chi_{NO} - {}^{III}\chi_{NO}]/{}^{II}t)(v_{12}+v_{15})/v_{12}]$$ (50)

where $v_{12}$ and $v_{15}$ are the volumes of gas injected during specified time by injectors 12 and 15 respectively and when $v_{12} \gg v_{15}$ the term $(v_{12}+v_{15})/v_{12}$ can be approximated by the value 1 and where for a continuously flowing system and continuously well mixed photoreactor 17, residence time in the photoreactor 17 ($^{II}t$) is given by $$^{II}t = v_{17}/f_{17}$$ (51)

where $v_{17}$ is the volume of photoreactor 17 and $f_{17}$ is the volumetric flowrate of mixture through photoreactor 17.

The rate coefficient $R_{smog}{}^t$ is then calculated from the known illumination and temperature conditions of photoreactor 17 and the value of $^{T,I}Q_{smog}{}^t$ by application off equation (38):

$$R_{smog}{}^t = {}^{T,I}Q_{smog}{}^t/I^t f(T^t)$$ (38)

and equation (39):

$$f(T^t) = e^{-1000\gamma(1/T^t - 1/316)}$$ (39)

where $\gamma$ has a value of 4.7 and $T_t$ the temperature of photoreactor 17, is in degrees Kelvin and $I^t$ is the illumination intensity within photoreactor 17.

Figure 2:
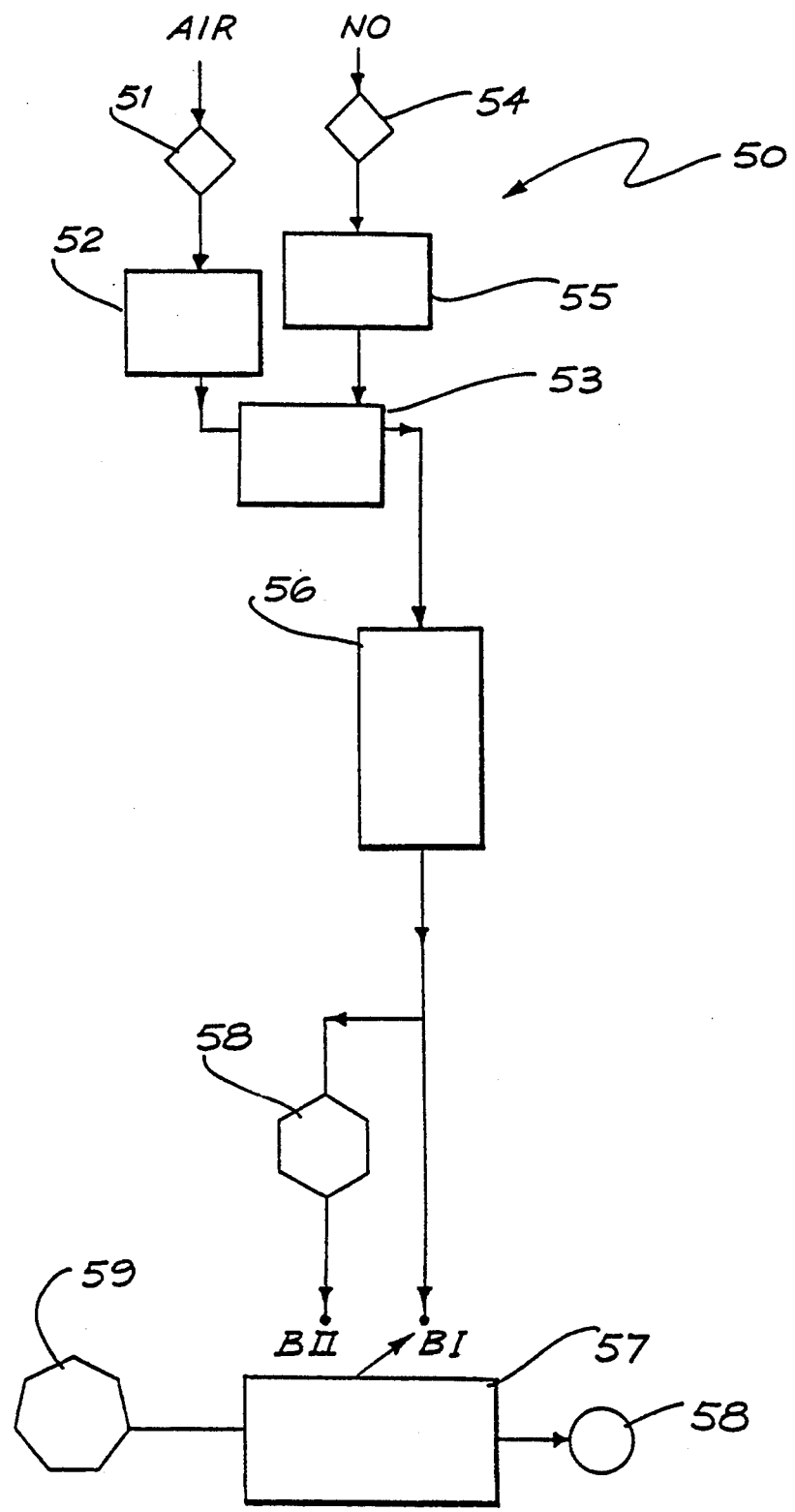

Referring to FIG. 2 a system 50 for determining concentration of smog in air includes an air filter 51 which filters incoming air and a metered delivery injector 52 which delivers a metered dose of the filtered air to combiner 53. A metered dosage of excess nitric oxide is combined with the filtered air in combiner 53 via nitric oxide filter 54 and metered delivery injector 55. As a result an excess nitric oxide/air mixture is formed in combiner 53.

The concentration of nitric oxide at injector 55 is typically high so that the volume of nitric oxide required to produce an excess nitric oxide/air mixture is small compared to the volume of the air with which it is combined, thus optionally enabling the volume of the nitric oxide added to be neglected for computational purposes.

Reactor 56 in which the mixture can react for a selected period wherein the excess nitric oxide reacts with substantially all ozone in the mixture is operatively coupled to combiner 53. Nitric oxide analyser 57 is operatively coupled to reactor 56 to determine the nitric oxide concentration of the mixture at point BI. Analyser 57 is also operatively coupled to reactor 56 via converter 58 which converts all the $NO_y$ in the mixture to nitric oxide so that the $NO_y$ concentration of the mixture can be determined as nitric oxide at point BII. The mixture is vented from the system via analyser 57 and vent 58. Computer 59 is operatively coupled to analyser 57 to calculate the smog concentration from the $NO_y$ and nitric oxide concentrations.

The concentration of smog in air can be determined in the following manner. A metered amount of air is delivered to combiner 53 after passing through filter 51 and injector 52. Excess nitric oxide is added to the air in combiner 53 after passing through filter 54, and injector 55 to provide an excess nitric oxide/air mixture in combiner 53.

The mixture is transferred to reactor 56 where it is permitted to react for a selected period wherein excess nitric oxide in the mixture reacts with substantially all ozone in the mixture. The nitric oxide concentration of the mixture is then measured by analyser 57 at point BI. The $NO_y$ concentration of the mixture is then measured as nitric oxide after passing through converter 58 at point BII. The concentration of smog is then calculated by computer 59 from the $NO_y$ and nitric oxide concentrations.

The concentration of smog is the gross concentration of nitric oxide consumed via reaction (2):

$$RO_2^* + NO \rightarrow NO_2$$ (2)

some nitric oxide thus consumed can be regenerated by reaction (3):

$$NO_2 + h\nu \xrightarrow{O_2} NO + O_3$$ (3)

however, addition of excess nitric oxide to air enables reactions to take place in reactor 56 such that nitric oxide previously regenerated by (3) is consumed by reaction (4):

$$NO + O_3 \rightarrow NO_2$$ (4)

The concentration of smog ($\chi_{smog}{}^t$) is calculated by equation (52) which is equation (16), corrected for dilution of air by mixing with added nitric oxide:

$$\chi_{smog}{}^t = [({}^I\chi_{NO_y} - {}^I\chi_{NO})(v_{52}+v_{55})/v_{52}]$$ (52)

where ${}^I\chi_{NO_y}$ is the concentration of nitric oxide at BII and $I\ {}^I\chi_{NO}$ is the concentration of nitric oxide at BI and $v_{52}$ and $v_{55}$ are the volumes of gas injected in specified time by injectors 52 and 55 respectively.

Figure 3:
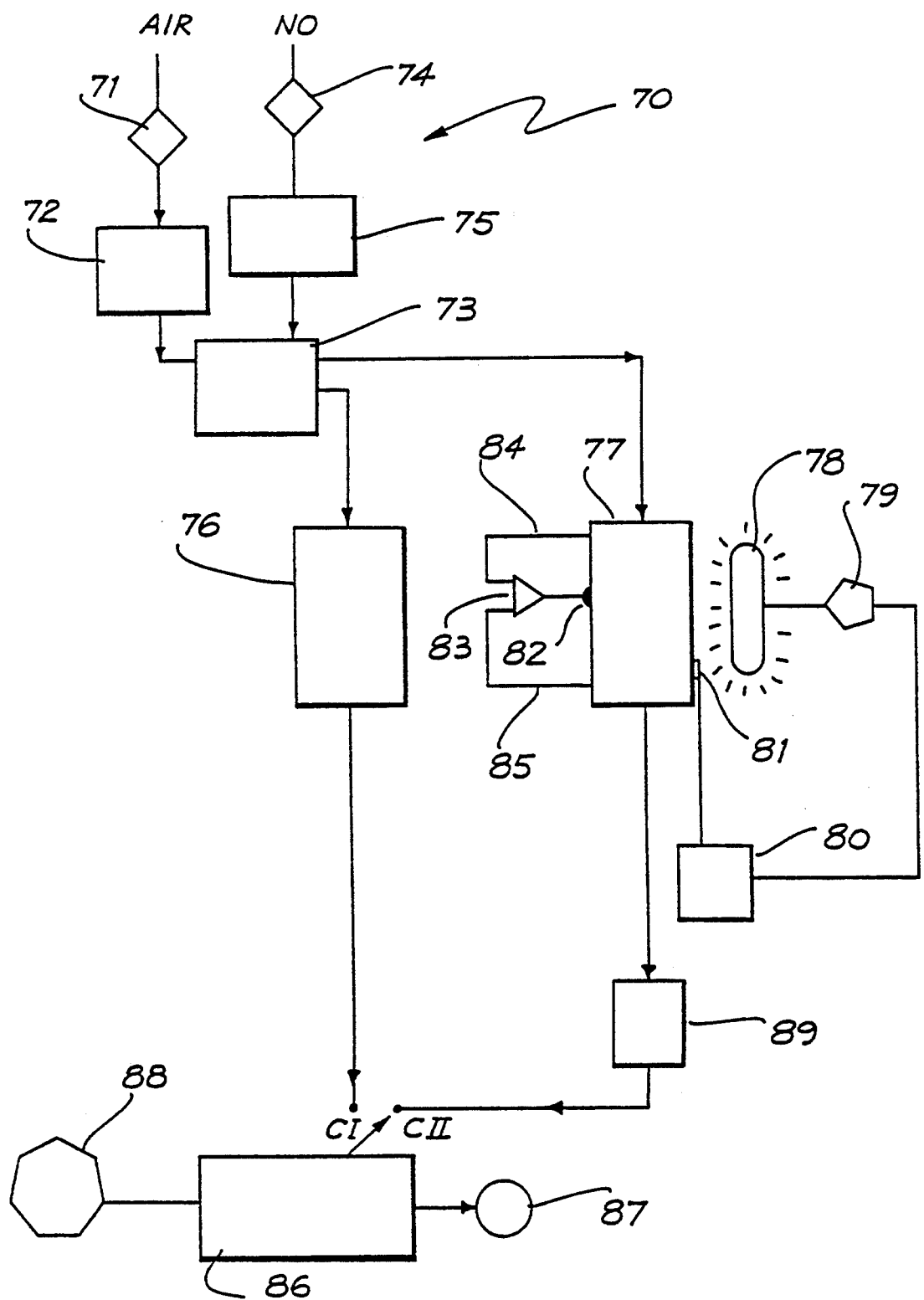
FIG. 3 is a block diagram of a system for determining rate of smog formation in air and also for determining ROC concentration of air and total concentration of prior ROC emissions into air.

Referring to FIG. 3 a system 70 for determining rate of smog formation in air under selected temperature and illumination conditions and ROC concentration of air and total concentration of prior ROC emissions into air includes an air filter 71 which filters incoming air and a metered delivery injector 72 which delivers a metered dose of the filtered air to combiner 73, A metered dosage of excess nitric oxide is combined with the filtered air in combiner 73 after passing through nitric oxide filter 74 and being injected into combiner 73 by metered delivery injector 75. The mixture is then dispensed via two separate streams.

The concentration of nitric oxide at injector 75 is typically high so that the volume of nitric oxide required to produce an excess nitric oxide/air mixture is small compared to the volume of the air with which it is combined, thus enabling the volume of the nitric oxide added to be neglected for computational purposes.

Reactor 75 in which the mixture can react for a first selected period wherein excess nitric oxide in the mixture reacts substantially all ozone in the mixture is operatively coupled to combiner 73.

Photoreactor 77 is also operatively coupled to combiner 73. Illumination source 78 is operatively disposed about photoreactor 77 to illuminate the mixture in photoreactor 77 for a second selected period under selected temperature and illumination conditions. Illumination from source 78 can be kept constant or can be varied according to a preselected or selected illumination profile. Illumination controller/programmer 79 is operatively coupled to source 78 and an illumination sensor consisting of photodiode 81 and photometer 80 for this latter purpose.

Temperature sensor 82 is operatively coupled to photoreactor 77 and temperature controller/programmer 83 to determine the temperature of the mixture in photoreactor 77. The temperature of the mixture in photoreactor 77 can be kept constant during illumination or can be allowed to vary and monitored or can be varied according to a preselected or selected temperature profile by temperature controller/programmer 83 which is operatively coupled to photoreactor 77 via lines 84 and 85. Reactor 89 in which during the third selected period excess nitric oxide of the mixture reacts with substantially all ozone is operatively coupled to photoreactor 77.

Nitric oxide analyser 86 is operatively coupled to reactor 76 to determine a first nitric oxide concentration of the mixture after the first selected period at point CI and operatively coupled to reactor 89 to determine a second nitric oxide concentration of the mixture after the third selected period at point CII. The mixture is vented from the system via analyser 86 and vent 87.

Preferably reactor 76 is of the same form and volume as the combination of the reaction vessels of photoreactor 77 and reactor 89 and the residence time for the mixture to pass from combiner 73 to CI is the same as that for the other part of the mixture to pass from combiner 73 to CII.

Computer 88 is operatively coupled to analyser 86 to calculate the rate from the first and second nitric oxide concentrations and the duration of the second selected period and the ROC concentration of air and total concentration of prior ROC emissions into air from the first and second nitric oxide concentration.

The rate of smog formation in air can be determined in the following manner. A metered amount of air is delivered to combiner 73 after passing through filter 71, and injector 72. Excess nitric oxide is added to the air in combiner 73 after passing through filter 74, and injector 75 to provide an excess nitric oxide/air mixture in combiner 73. The mixture is transferred to reactor 76 and photoreactor 77. The mixture is permitted to react in reactor 76 for a first selected period wherein excess nitric oxide in the mixture reacts with substantially all ozone in the mixture. A first nitric oxide concentration of the mixture is then measured by analyser 86 at point CI. The mixture is illuminated in photoreactor 77 for a second selected period under selected temperature and illumination conditions and further allowed to react for a third selected period in reactor 89. A second nitric oxide concentration of the mixture is measured after the third selected period at point CII by analyser 86. Preferably the duration of the first period is equal to the total duration of the second and third periods.

The rate $^{T,I}Q_{smog}{}^t$ under selected temperature and illumination conditions is then calculated by computer 88 from the first and second nitric oxide concentrations ($^I\chi_{NO}$ and $^{III}\chi_{NO}$ respectively) and the duration of the second selected period ($^{II}t$).

The rate of smog formation is measured as the rate of reaction (2):

$$RO_2^* + NO \rightarrow NO_2 \qquad (2)$$

where $NO_2$ denotes predominantly nitrogen dioxide but also organic nitrates and other trace nitrogenous products. The rate is calculated from the consumption of nitric oxide in photoreactor 77 when excess nitric oxide is present in air by utilizing equation (36) and explicitly by the expression:

$$^{T,I}Q_{smog}{}^t = [(\{^I\chi_{NO} - {}^{III}\chi_{NO}\}/{}^{II}t)\,(v_{72}+v_{75})/v_{72}] \qquad (53)$$

where for a continuously flowing system and continuously well mixed photoreactor 77 residence time in photoreactor 77 is given by:

$$^{II}t = v_{yy}/f_{77} \qquad (54)$$

where $v_{77}$ is the volume of the photoreactor 77 and $f_{77}$ is the flowrate of mixture through photoreactor 77 and $v_{72}$ and $v_{75}$ are the volumes of gas injected per specified time by injectors 72 and 75 respectively.

ROC concentration of air and total concentration of prior ROC emissions into air can be determined in the following manner. A metered amount of air is delivered to combiner 73 after passing through filter 71, and injector 72. Excess nitric oxide is added to the air in combiner 73 after passing through filter 74, and injector 75 to provide an excess nitric oxide/air mixture in combiner 73. The mixture is transferred to reactor 76 and photoreactor 77. The mixture is permitted to react in reactor 76 for a first selected period wherein excess nitric oxide in the mixture reacts with substantially all ozone in the mixture. A first nitric oxide concentration of the mixture is then measured by analyser 86 at point CI. The mixture is illuminated in photoreactor 77 for a second selected period under selected temperature and illumination conditions and further allowed to react for a third selected period in reactor 89. A second nitric oxide concentration of the mixture is measured after the third selected period at point CII by analyser 86. Preferably the duration of the first period is equal to the total duration of the second and third periods. A metered amount of reference air of known ROC concentration and ROC composition representative of that of the air for analysis is delivered to combiner 73 after passing through filter 71, and injector 72. Excess nitric oxide is added to the reference air in combiner 73 after passing through filter 74, and injector 75 to provide an excess nitric oxide reference air mixture in combiner 73. The reference mixture is transferred to reactor 76 and photoreactor 77. The reference mixture is permitted to react in reactor 76 for a first selected period wherein excess nitric oxide in the reference mixture reacts with substantially all ozone in the reference mixture. A first nitric oxide concentration of the reference mixture is then measured by analyser 86 at point CI. The reference mixture is illuminated in photoreactor 77 for a second selected period under selected temperature and illumination conditions and further allowed to react for a third selected period in reactor 89. A second nitric oxide concentration of the reference mixture is measured after the third selected period at point CII by analyser 86. The duration of the first, second and third periods and selected temperature and illumination conditions of photoreactor 77 are maintained the same during passage of both the air and the reference air through system 70.

The ROC concentration of the air ($\chi_{ROC}^t$) and the total concentration of prior ROC emissions ($^o\chi_{ROC}^t$) into the air is calculated by computer 88 from the first and second nitric oxide concentrations of the air mixture ($^I\chi_{NO}$ and $^{III}\chi_{NO}$ respectively) and the first and second nitric oxide concentrations of the reference air mixture ($^I\chi_{NO}^\Gamma$ and $^{III}\chi_{NO}^\Gamma$ respectively) and the ROC concentration of the reference air ($\chi_{ROC}^\Gamma$).

In the presence of excess nitric oxide, nitric oxide is consumed in photoreactor 77 in proportion to the ROC concentration of the air within the reactor. The ROC concentration of air is calculated from the nitric oxide consumed by the air compared to the nitric oxide consumed under the same conditions by reference air of known ROC concentration by equation (128).

$$\chi_{ROC}^t = \chi_{ROC}^\Gamma (^I\chi_{NO} - ^{III}\chi_{NO}) / (^I\chi_{NO}^\Gamma - ^{III}\chi_{NO}^\Gamma) \quad (128)$$

The products of reaction by ROC species are also ROC species and for ROC compositions representative of urban air product ROC have similar photochemical reactivity to the reactant ROC, at least to a good approximation for the extent of reaction as can occur in the atmosphere on a sunny day. As the reactivity of prior ROC emissions is conserved the total concentration of prior ROC emissions is given by $$^o\chi_{ROC}^t = \chi_{ROC}^t \quad (106)$$

Figure 4:
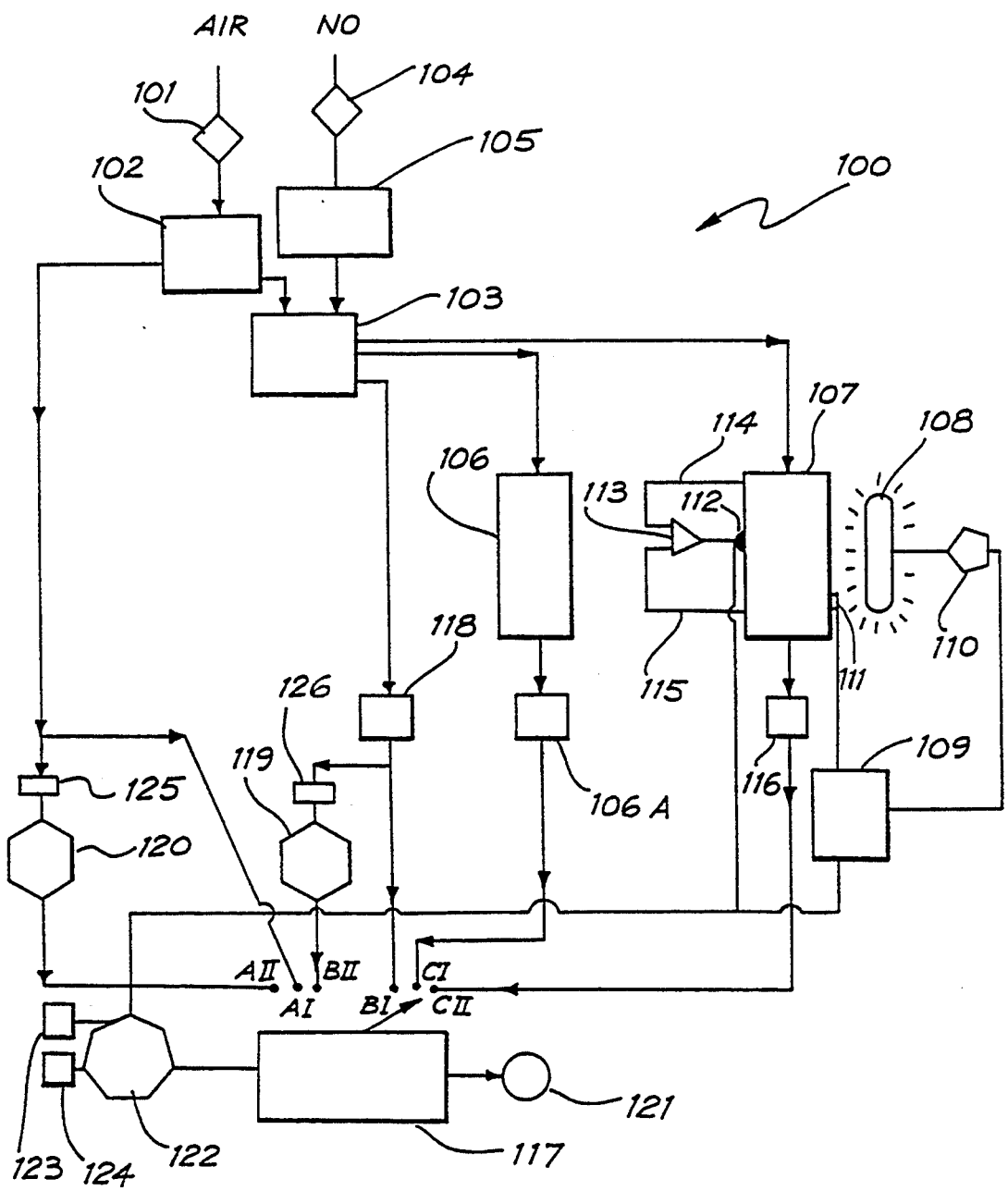
FIG. 4 is a block diagram of an alternative system for determining rate coefficient of smog formation in air; smog concentration, amount of prior smog formation, maximum potential smog concentration, extent of smog formation, rate of smog formation under selected temperature and illumination conditions, $NO_y$, $O_3$ and nitric oxide concentrations of $NO/NO_x$ concentration ratio of the $NO_x$ previously introduced into air, time period required for maximum smog formation, ROC content of ROC/$NO_x$ concentration ratio of total previous introductions into air, total concentrations of ROC, $NO_y$ and $NO_x$ previously introduced into air, time period during which smog formation has occurred, average time of previous introductions of ROC into air, and time period required for production of selected amount of smog in air.

Referring to FIG. 4 a system 100 for determining rate coefficient of smog formation, smog concentration, amount of prior smog formation, maximum potential smog concentration, extent of smog formation in air, rate of smog formation under selected temperature and illumination conditions, $NO_y$ ozone and nitric oxide concentrations of air, time period required for maximum smog formation in air under selected conditions of temperature and illumination, ROC content of air, total concentration of ROC previously introduced into air, total concentration of $NO_y$ previously introduced into air, total concentration of nitric oxide previously introduced into air, $NO/NO_x$ concentration ratio of the $NO_x$ previously introduced into air, $ROC/NO_x$ concentration ratio of total ROC and total $NO_x$ previously introduced into air, time period during which smog formation has occurred, average time of previous introductions of ROC into the air and time period required for production of selected amount of smog in air under selected conditions of temperature and illumination, includes an air filter 101 which filters incoming air and a metered delivery injector 102 which delivers a metered dose of the filtered air to combiner 103 and a second metered dose to AI and $NO_y$ converter 120. A metered dosage of excess nitric oxide is combined with the Filtered air in combiner 103 after passing through nitric oxide filter 104 and being injected therein by metered delivery injector 105. As a result an excess nitric oxide/air mixture is formed in combiner 103 and dispensed therefrom via three separate streams.

Reactor 106 in which the mixture can react for a First selected period wherein excess nitric oxide in the mixture reacts with substantially all ozone in the mixture, is operatively coupled to combiner 103 and reactor 106A. Photoreactor 107 is also operatively coupled to combiner 103. Illumination source 108 is operatively disposed about photoreactor 107 to illuminate the mixture in photoreactor 107 for a second selected period under known temperature and illumination conditions. Illumination from source 108 can be kept constant or can be varied according to a preselected or selected illumination profile. Illumination controller/programmer 110 is operatively coupled to source 108 and an illumination sensor consisting of photodiode 111 and photometer 109 for this latter purpose.

The illumination intensity can be determined via absolute measurement of the illumination intensity by sensor 111 and photometer 109 or alternatively by calibration. Calibration of the illumination intensity may be achieved by providing a supply of air of known rate coefficient of smog formation to filter 101, the residence time of the known air/nitric oxide mixture in photoreactor 107, the temperature of photoreactor and the nitric oxide concentrations at CI and CII.

Temperature sensor 112 is operatively coupled to photoreactor 107 and temperature controller/programmer 113 to determine the temperature of the mixture in photoreactor 107. The temperature of the mixture photoreactor 107 can be kept constant during illumination or can be allowed to vary and monitored or can be varied according to a preselected or selected temperature profile by temperature controller/programmer 113 which is operatively coupled to photoreactor 107 via lines 114 and 115.

Reactor 106 in which during a third selected period excess nitric oxide reacts with substantially all ozone in the mixture is operatively coupled to photoreactor 107.

Nitric oxide analyser 117 is operatively coupled to reactor 106A to determine a first nitric oxide concentration of the mixture after the first selected period at point CI and operatively coupled to reactor 116 to determine a second nitric oxide concentration of the mixture after the third selected period at point CII.

Reactors 106 and 106A have form and configuration similar to the combined assembly of photoreactor 107 and reactor 116, respectively, by which means the mixing processes and the residence time of that part of the mixture passing from combiner 103 to point CI is approximately the same as that part of the mixture passing from combiner 103 to point CII, thus ensuring that the mixture composition at any moment at CI and at CII pertain to air which initially formed part of a common mixture combiner 103. This feature is particularly useful when the composition of air passing through filter 101 is variable.

Reactor 118 in which mixture can react for a fourth selected period wherein excess nitric oxide of the mixture reacts with substantially all ozone in the mixture is operatively coupled to combiner 103. Analyser 117 is operatively coupled to reactor 118 to determine nitric oxide concentration of the mixture at point BI. Analyser 117 is also operatively coupled to reactor 118 via $NO_y$ converter 119 to determine a $NO_y$ concentration of the mixture at point BII. Analyser 117 is also operatively coupled to injector 102 to determine the nitric oxide concentration of the air at point AI. Analyser 117 is also operatively coupled to injector 102 via $NO_y$ converter 120 to determine the $NO_y$ concentration of the air at point AII. The mixture and air are vented from the system via analyser 117 and vent 121. Computer 122 is operatively coupled to temperature sensor 112, photometer 109, analyser 117. Computer 122 is also operatively coupled to temperature sensor 123 and illumination sensor 124. Temperature sensor 123 is disposed to determine the temperature of the ambient air prior to analysis by system 100 and illumination sensor 124 is disposed to determine the sunlight flux in the ambient air.

Optionally, a nitric acid scrubber 125 is coupled to the inlet at converter 120 and a nitric acid scrubber 126 is coupled to the inlet of converter 119 to remove nitric acid vapour from the air and mixture respectively prior to entering the converters 119 and 120.

Computer 122 processes signals from operatively coupled to sensors and analyser to calculate: the rate coefficient of smog formation in air from the nitric oxide concentrations at CI and CII, the known temperature and illumination conditions of photoreactor 107 and the duration of the second selected period; the concentration of smog in air from the nitric oxide concentrations at BI and BII; the amount of prior smog formation from concentrations of nitric oxide at AII, 8I and BII; the maximum potential smog concentration of air from the nitric oxide concentrations measured at AII, BI and BII; extent of smog formation in air from the concentrations of nitric oxide measured at AII, BI and BII; the rate of smog formation under the selected conditions of temperature and illumination from the nitric oxide concentrations measured at CI and CII and the duration of the second selected period; the $NO_y$ concentration of air from the nitric oxide concentration measured at AII; the ozone concentration of air from the nitric oxide concentrations measured at AI, BI and BII and the nitric oxide concentration of air from the nitric oxide concentration measured at AI and (or alternatively) the ozone and nitric oxide concentrations of air from the measured nitric oxide concentrations at AII, BI and BII and the temperature of air as measured at sensor 123 and illumination intensity of sunlight at sensor 124; the time period required for maximum smog formation in air under selected conditions of illumination and temperature from the measured nitric oxide concentrations at AII, BI, BII, CI and CII, and the duration of the second selected period; time period during which smog formation in air has occurred, the time period being substantially the same as or within a selected period for which the illumination and temperature conditions are known, wherein the end of the selected period coincides with the end of the time period from the measured nitric oxide concentrations at AII, BI, BII, CI, CII, the duration of the second selected period, the temperature measured at sensor 112 and illumination intensity measured at sensor 111 and the temperature and illumination of air monitored by sensors 123 and 124 respectively throughout the duration of the selected period during which smog formation in air has occurred; time period required for production of selected amount of smog in air under selected conditions of temperature and illumination from the nitric oxide concentrations measured at AII, BI, BII, CI and CII, the duration of the second selected period, the temperature measured at sensor 112 and the illumination intensity measured at sensor III and the selected conditions of temperature and illumination of the air and the selected amount of smog; the ROC content of air from the nitric oxide concentrations at CI and CII, the temperature measured at sensor 112 and illumination intensity measured at sensor 111 and the duration of the second selected period; the total concentration of ROC previously introduced into air from the ROC content of air determined as above; the $NO_y$ concentration of air from the nitric oxide concentration measured at AII; the total concentrations of $NO_x$ and $NO_y$ previously introduced into air from the nitric oxide concentrations measured at AI, AII, BI and BII or alternatively from the measured nitric oxide concentrations measured at AII, BI and BII, the temperature of the air measured at sensor 123 and illumination intensity of sunlight measured at sensor 124; the total concentration of nitric oxide previously introduced into air from the nitric oxide concentrations measured at AI, AII, BI and BII or alternatively from the nitric oxide concentrations measured at AII, BI and BII, the temperature of the air measured at sensor 123 and illumination intensity of sunlight measured at sensor 124; the $NO/NO_x$ concentration ratio of the $NO_x$ introduced into air ($^oF_{NO}$) from the NO concentrations measured at AI, AII, BI and BII, the temperature of the air measured at sensor 123 and the illumination intensity of sunlight measured at sensor 124; the $ROC/NO_x$ concentration ratio of the total ROC and total $NO_x$ previously introduced into air from the nitric oxide concentrations measured at AII, BI, BII, CI and CII, the temperature measured at sensor 112 and illumination intensity measured at sensor 111, the duration of the second selected period and also the NO concentration measured at AI or alternatively the temperature of the air measured at temperature sensor 123 and illumination intensity of sunlight measured at sensor 124; average time of prior introductions of ROC into air from the concentrations of nitric oxide at AII, BI, BII, CI and CII, the temperature-time profile of the air measured at temperature sensor 123, the illumination intensity-time profile of the air measured at sunlight illumination sensor 124 and also the NO concentration measured at AI or alternatively the air temperature measured at sensor 123 at the time of sampling the air and the illumination intensity measured at sensor 124 at the time of sampling the air.

The rate coefficient of smog formation in air can be determined the following manner:

A metered amount of air is delivered to combiner 103 after passing through filter 101 and injector 102. Excess nitric oxide is added to the air in combiner 103 after passing through filter 104 and injector 105 to provide an excess nitric oxide/air mixture in combiner 103. Metered amounts of the mixture are transferred to reactor 106 and 106A and photoreactor 107. The mixture is permitted to react in reactor 106 and 106A for a first selected period wherein excess nitric oxide in the mixture reacts with substantially all ozone in the mixture. A first nitric oxide concentration of the mixture is then measured by analyser 117 at point CI. The mixture is illuminated in photoreactor 107 for a second selected period under known temperature and illumination conditions and then transferred to reactor 116. The mixture is permitted to react in reactor 116 for a third selected period wherein excess nitric oxide in the mixture reacts with substantially all ozone.

A second nitric oxide concentration of the mixture is measured after the third selected period at point CII by analyser 117. The rate coefficient is then calculated by computer 122 from the first and second nitric oxide concentrations, the known temperature and illumination conditions of photoreactor 107 and the duration of the second selected period.

In system 100 optionally reactors 106 and 106A and reactor 118 are the same reactor and then points BI and CI become the same point, however there is an advantage in employing separate reactors of differing volumes as reactors 106 and 106A and reactor 118. This is because preferably the residence time of the mixture in reactors 106 and 106A is the same as the combined residence times of mixture in reactors 107 and 116, and the residence time in photoreactor 107 is preferred to be in the order of ten minutes, the longer the residence time in photoreactor 107 the greater being the sensitivity of system 100 for determining rate of smog formation and rate coefficient of smog formation. The residence time preferred for the mixture in reactor 118 is shorter than the preferred residence time in photoreactor 107 and is of the order of one minute and it is preferred that the residence time of the mixture in reactor 118 is as short as is consistent with the reaction of ozone with excess nitric oxide going substantially to completion in reactor 118. This is desirable especially when the composition of air at filter 101 is rapidly varying for then the air delivered from filter 101 to analyser 117 via points AI and AII will be close to having the same composition as air delivered from filter 101 to analyser 117 via points BI and BII. This in turn minimizes the possibility of transitory spurious values for ozone concentrations being determined by system 100 due to the mixture measured at points A and B having as origins air of different compositions The rate coefficient for smog formation in air is determined by measurement of nitric oxide consumed by reaction (2):

$$RO_2 + NO \rightarrow NO_2 \tag{2}$$

in photoreactor 107. Some nitrogen dioxide produced by reaction (2) undergoes further reaction in photoreactor 107, producing ozone and regenerating nitric oxide by reaction (3):

$$NO_2^* + h\nu \xrightarrow{O_2} NO + O_3 \tag{3}$$

Nitric oxide regenerated by reaction (3) further reacts with excess nitric oxide by reaction (4):

$$NO + O_3 \rightarrow NO_2 \tag{4}$$

either within photoreactor 107 or subsequently in reactor 116. The nitric oxide consumed by photoreaction of ROE species in photoreactor 107 is the difference in nitric oxide concentrations of the mixture at points CII and CI. The rate of smog formation ($^{T,I}Q_{smog}{}^t$) in photoreactor 107 is calculated by equation (36), corrected for dilution of air by mixing with added nitric oxide, by the expression:

$$^{T,I}Q_{smog}{}^t = \{[(^I\chi_{NO} - {}^{III}\chi_{NO}) / {}^{III}t][(v_{102} + v_{105})/v_{102}]\} \tag{55}$$

where $^{III}\chi_{NO}$ is the concentration of nitric oxide measured at CII and $^I\chi_{NO}$ is the nitric oxide concentration measured at CI by analyser 117 and where $v_{102}$ and $v_{105}$ are the volumes of gas injected during specified time into combiner 103, by injectors 102 and 105 respectively. Optionally where $V_{102} >> V_{105}$ the term $(v_{102} + v_{105})/v_{102}$ can be approximated by the value 1 and where for a continual flowthrough system 100 and continuously well mixed photoreactor 107, residence time in the photoreactor 107 ($^{II}t$) is given by:

$$^{II}t = v_{107}/f_{107} \tag{56}$$

where $v_{107}$ is the volume of photoreactor 107, and $f_{107}$ is the volumetric flowrate of mixture supplied by combiner 103 and passing through photoreactor 107.

The rate coefficient $R_{smog}{}^t$ is calculated from the known illumination and temperature conditions of photoreactor 107 and the value of 2 $Q_{smog}{}^t$ by application of equation (38):

$$R_{smog}{}^{T,I}Q_{smog}{}^t / I^t f(T^t) \tag{38}$$

and equation (39):

$$f(T^t) = e^{-1000\gamma(1/T^t - 1/316)} \tag{39}$$

where $\gamma$ has a value of 4.7 and the temperature of photoreactor 107 ($T^I$) is in degrees Kelvin and $I^I$ is the illumination intensity within photoreactor 107.

The concentration of smog in air can be determined in the following manner.

A metered volume of air is delivered to combiner 1033 after passing through filter 101 and injector 102. Metered volume of excess nitric oxide is added to the air in combiner 103 after passing through filter 104 and injector 105 to provide an excess nitric oxide/air mixture in combiner 103. The mixture is transferred to reactor 118. The mixture permitted to react in reactor 118 for a fourth selected period wherein excess nitric oxide in the mixture reacts with substantially all ozone in the mixture. A third nitric oxide concentration of the mixture is then measured by analyser 117 at point BI. Mixture from reactor 318 is delivered to nitric oxide converter 119 wherein the $NO_y$ in the mixture is converted to nitric oxide. The mixture is delivered from converter 119 to point BII and a fourth nitric oxide concentration measured by analyser 117. The concentration of smog in air is then calculated by computer 122 from the third and fourth nitric oxide concentrations.

As already indicated, smog concentration of air is the sum of the concentrations of ozone and $NO_y$ less the concentration of NO, and $\chi_{smog}{}^t$ is the concentration of smog in air at time t. It follows that $\chi_{smog}{}^t$ is equivalent to the concentration of nitrogen dioxide and other gas phase nitrogen containing species in air produced by reaction of nitrogen dioxide, that is, the nitrogenous products off reactions (3) and (6):

$$NO_2 + h\nu \xrightarrow{O_2} NO + O_3 \qquad (3)$$

$$NO_x + RO_2 \longrightarrow \text{Stable gas phase nitrogen containing products} \qquad (6)$$

When excess nitric oxide is added to air, nitrogen dioxide consumed by reaction (3) is regenerated from the ozone produced by reaction (3) by reaction (4):

$$NO + O_3 \rightarrow NO_2 \qquad (4)$$

enabling the smog concentration of air ($\chi_{smog}{}^t$) to be calculated from the difference in nitric oxide concentrations at points BII and BI, by equation (57):

$$\chi_{smog}{}^t = [(^{BII}\chi_{NO} - {}^{BI}\chi_{NO})(v_{102}+v_{105})/v_{102}] \qquad (57)$$

where ${}^{BII}\chi_{NO}$ and ${}^{BI}\chi_{NO}$ are the concentrations of nitric oxide at points BII and BI respectively and measured by analyser 117 and $v_{102}$ and $v_{105}$ are the volumes of gas injected during specified time into combiner 103 by injectors 102 and 105 respectively.

The rate of smog formation in air under selected temperature and illumination conditions can be determined in the following manner:

A metered amount of air is delivered to combiner 103 after passing through filter 101 and injector 102. Excess nitric oxide is added to the air in combiner 103 after passing through filter 104 and injector 105 to provide an excess nitric oxide/air mixture in combiner 103. Metered amounts of the mixture are transferred to reactors 106 and 106A and photoreactor 107. The mixture is permitted to react in reactors 106 and 106A for a first selected period wherein excess nitric oxide in the mixture reacts with substantially all ozone in the mixture. A first nitric oxide concentration of the mixture is then measured by analyser 117 at point CI. The mixture is illuminated in photoreactor 107 for a second selected period under the selected temperature and illumination conditions and then transferred to reactor 116. The mixture is permitted to react in reactor 116 for a third selected period wherein excess nitric oxide in the mixture reacts with substantially all ozone.

The rate of smog formation in air under the selected temperature and illumination conditions of photoreactor 107 is the rate of reaction (2):

$$RO_2^* + NO \rightarrow NO_2 \qquad (2)$$

Some nitrogen dioxide produced by reaction (2) undergoes further reaction in photoreactor 107, producing ozone and regenerating nitric oxide according to reaction (3):

$$NO_2 + h\nu \xrightarrow{O_2} NO + O_3 \qquad (3)$$

Nitric oxide regenerated by reaction (3) further reacts with excess nitric oxide according to reaction (4):

$$NO + O_3 \rightarrow NO_2 \qquad (4)$$

either within photoreactor 107 or subsequently in reactor 116. Thus, the amount of nitric oxide consumed by reaction (2) in photoreactor 107 is equal to The difference in nitric oxide concentrations of the mixture between points CII and CI. The rate of smog formation ($^{T,I}Q_{smog}{}^t$) under the selected conditions of illumination I and temperature T of photoreactor 107 is calculated according to equation (36) and corrected for dilution of air by mixing with added nitric oxide, according to the expression:

$$^{T,I}Q_{smog}{}^t = \{[(^{I}\chi_{NO} - {}^{III}\chi_{NO}) /{}^{II}t][(v_{102}+v_{105})/v_{102}]\} \qquad (55)$$

where $^{III}\chi_{NO}$ is the concentration of nitric oxide measured at CII and $^{I}\chi_{NO}$ is the nitric oxide concentration measured at CI by analyser 117 and where $v_{102}$ and $v_{105}$ are the volumes of gas injected during the specified time into combiner 103, by injectors 102 and 105 respectively. Optionally where $v_{102} \gg v_{105}$ the expression $(v_{102}+v_{105})/v_{102}$ can be approximated by the value 1. For a continually flowing system and continuously well mixed photoreactor 107, residence time in the photoreactor 107 ($^{II}t$) is given by:

$$^{II}t = v_{107}/f_{107} \qquad (56)$$

where $v_{107}$ is the volume of photoreactor 107, and $f_{107}$ is the volumetric flowrate of mixture supplied by combiner 103 and passing through photoreactor 107.

The $NO_y$, nitric oxide and ozone concentrations of air can be determined in the following manner. Air from injector 102 is delivered to nitric oxide converter 120 wherein all the $NO_y$ in the air is converted to NO. The mixture from converter 120 is delivered to point AII and the $NO_y$ concentration of the air is measured as a fifth nitric oxide concentration $^{AII}\chi_{NO}$ at point AII and the concentration of $NO_y$ calculated according to equation (89):

$$\chi_{NO_y}{}^t = {}^{AII}\chi_{NO}{}^t \tag{89}$$

Air from injector 102 is delivered to point AI and the nitric oxide concentration of air is measured as a sixth nitric oxide concentration ($^{AI}\chi_{NO}$) by analyser 117 at point AI and the concentration of nitric oxide in air calculated according to equation (63):

$$\chi_{NO}{}^t = {}^{AI}\chi_{NO}{}^t \tag{63}$$

The ozone concentration of air $\chi_{smog}{}^t$ is calculated by computer 122 from the fifth and sixth nitric oxide concentrations and the smog concentration of air $\chi_{smog}{}^t$ according to equation (44) by equation (62):

$$\chi_{O_3}{}^t \leq \chi_{smog}{}^t + {}^{AI}\chi_{NO}{}^t - {}^{AII}\chi_{NO}{}^t \tag{62}$$

The amount of prior smog formation in air ($^f\chi_{smog}{}^t$) can be determined in the following manner. The smog concentration of air ($\chi_{smog}{}^t$) is determined as described and calculated according to equation (57) and also air from injector 102 is delivered to converter 120 wherein all $NO_y$ of the air is converted to nitric oxide. The $NO_y$ concentration of the air ($\chi_{NO_y}{}^t$) is then measured as a fifth nitric oxide concentration by analyser 117 at point AII ($^{AII}\chi_{NO}{}^t$). The concentration at time t of $NO_y$ that would exist in the absence of $NO_y$ removal processes from air ($^o\chi_{NO_y}{}^t$), and which represents the cumulative emissions of $NO_y$ into air is calculated from the values determined for $\chi_{NO_y}{}^t$, $\chi_{NO}{}^t$ and $\chi_{O_3}{}^t$.

The procedure for determining $^o\chi_{NO_y}{}^t$ depends on the extent of smog formation $E_{smog}{}^t < 1$ then the $NO_y$ ($E_{smog}{}^t$ equation 34,when) lost from the air by the action of reaction (7) can be evaluated on the basis of the measured values of $\chi_{NO_y}{}^t$, $\chi_{NO}{}^t$ and $\chi_{O_3}{}^t$ and the values of $P_{7,2}$ and $^oF_{NO}$. When $E_{smog}{}^t = 1$ smog formation does not occur in the air (because of insufficient concentration of nitric oxide to enable reaction (2) to proceed at an appreciable rate) but $NO_y$ can continue to be removed from the air via reaction (7). In the case of $E_{smog}{}^t = 1$ another method is used to evaluate $^o\chi_{NO_y}{}^t$ which employs the value measured for $\chi_{O_3}{}^t$ and which is independent of $\chi_{NO_y}{}^t$.

To determine the domain of $E_{smog}{}^t$ the value of $G^t$ is determined according to equation (58).

$$G^t = \frac{\chi^t_{O_3}/(\beta - 2{}^oF_{NO})}{\chi^t_{NO_y} + P_{7,2}({}^oF_{NO}\chi^t_{NO_y} + \chi^t_{O_3} - \chi^t_{NO})/(1 - {}^oN_{NO}P_{7,2})} \tag{58}$$

The denominator of equation (58) is an expression for $^o\chi_{NO_y}{}^t$ according to equation (59) which is derived from equations (19, 21 and 27) and which is appropriate to the case of $E_{smog}{}^t < 1$ but which underestimates the value of $^o\chi_{NO_y}{}^t$ when $E_{smog}{}^t = 1$.

The numerator of equation (58) is an expression for $^o\chi_{NO_y}{}^t$ according to equation (60) which is appropriate to the case of $E_{smog}{}^t = 1$ but which underestimates the value of $^o\chi_{NO_y}{}^t$ when $E_{smog}{}^t < 2$.

When $$G^t = 1$$

then $$E_{smog}{}^t < 1$$

and when $$G^t < 1$$

then $$E_{smog}{}^t = 1 \tag{129}$$

and $$^o\chi_{NO_y}{}^t = \chi_{NO_y}{}^t + P_{7,2}({}^oF_{NO}\chi_{NO_y}{}^t + \chi_{O_3}{}^t - \chi_{NO}{}^t)/(1 - {}^oF_{NO}P_{7,2}) \quad (E_{smog}{}^t < 1) \tag{59}$$

otherwise $$^o\chi_{NO_y}{}^t = \chi_{O_3}{}^t/(\beta - {}^oF_{NO}) \quad (E_{smog}{}^t = 1) \tag{60}$$

Equation (60) arises from the following considerations:

When $E_{smog}{}^t$ then the value of $\chi_{NO}{}^t$ is small and approaching zero, thus for the purpose of these calculations nitric oxide concentration can be assigned the value $$\chi_{NO}{}^t = 0 \quad (E_{smog}{}^t = 1)$$

Also when $$E_{smog}{}^t = 1$$

then $^r\chi_{smog}{}^t = {}^{fmax}\chi_{smog}{}^t$ and by equation (31)

$$^f\chi_{smog}{}^t = \beta {}^o\chi_{NO_y}{}^t \quad (E_{smog}{}^t = 1) \tag{120}$$

Now for the case $E_{smog}{}^t = 1$ (and $\chi_{NO}{}^t = 0$) it follows from t equations (17), (18) and (27) that the ozone concentration of air is given by $$\chi_{O_3}{}^t = {}^{Tmax}\chi_{smog}{}^t - {}^oF_{NO}{}^o\chi_{NO_y}{}^t (E_{smog}{}^t = 1) \tag{122}$$

Substitution of (118) into (122) gives $^o\chi_{NO_y}{}^t$ in terms of $\chi_{O_3}{}^t$ $$\chi_{O_3}{}^t = {}^o\chi_{NO_y}{}^t(\beta - {}^oF_{NO}) \quad (E_{smog}{}^t = 1) \tag{123}$$

and (123) can be rearranged to make $^o\chi_{NO_y}{}^t$ the dependent variable, yielding equation (60).

The amount of prior smog formation in air is calculated according to equations (29), (31), (57), (58) and (62) by equation (61):

$$f_{\chi_{smog}}{}^t = \{[\chi_{smog}{}^t - (1 - {}^oF_{NO})^{AII}\chi_{NO}{}^t]/(1 - {}^oF_{NO}P_{7,2})\}G^t < 1$$

or $$f_{\chi_{smog}}{}^t = \beta\chi_{O_3}{}^t/(\beta - {}^oF_{NO}) \ T^t \ll 1 \tag{61}$$

where $\beta$, ${}^oF_{NO}$ and $P_{7,2}$ are independently determined coefficients which for most circumstances pertinent to air of composition as commonly found in urban regions can be assigned the values:

$$\beta = 4$$

$${}^oF_{NO} = 0.9$$

$$P_{7,2} = 0.125.$$

The value of $P_{7,2}$ is a function of the relative rates of reactions (7) and (2). However, the rate of reaction (7) can be variable as the product distribution of the reaction of $NO_2$ with $RO_2$ can vary. In some circumstances nitric acid, one of the reaction products, can remain in the gas phase or alternatively a variable proportion of the nitric acid formed can be incorporated, possibly by adsorption, into non-gaseous species. The effect of this variability of product distribution on the value of $P_{7,2}$ may optionally be minimized by incorporation of nitric acid scrubbers 125 and 126 into the system. When scrubbers 125 and 126 are included then nitric acid is excluded from the definition of $NO_y$. A suitable nitric acid scrubber is a porous nylon membrane or nylon tube through which the sample and mixture are passed. Nylon surfaces remove nitric acid from air. When nitric acid is thus removed prior to converters 120 and 121 then the relative rates of reactions (7) and (2) are made less variable but the rate of reaction (7) is increased. When nitric acid scrubbers are incorporated into system 100 a value of about $P_{7,2} = 0.25$ is suitable for most determinations of prior smog formation in air.

The maximum potential smog concentration in air ($^{fmax}\chi_{smog}{}^t$) can be calculated from the determined value of ${}^o\chi_{NO_y}{}^t$ in air.

The extent of smog formation in air at time t ($E_{smog}{}^t$), being the proportion of smog produced by time t compared to the maximum potential amount of smog formation can be determined from $^{fmax}\chi_{smog}{}^t$ and $^{max}\chi_{smog}{}^t$ according to equations (61) and (31) respectively according to equation (35):

$$E_{smog}{}^t = (^f\chi_{smog}{}^t/^{fmax}\chi_{smog}{}^t) \tag{35}$$

System 100 provides other methods for determination of the nitric oxide and ozone concentrations of air, which are as follows: The illumination intensity of air is measured by sensor 124 and the temperature of air is measured by sensor 123.

The nitric oxide and ozone concentrations are determined by first calculating the rate coefficient of reaction (3) $k_3{}^t$, from the known coefficients for $NO_2$ photolysis, the illumination intensity measured by sensor 124 and the temperature measured by sensor 123. If $k_3{}^t$ is zero then the nitric oxide and ozone concentrations are calculated by equations (68) and (69) respectively and the values of $\chi_{smog}{}^t$ and $\chi_{NO_y}{}^t$, obtained as described previously.

If $k_3{}^t$ is non zero then the values of ${}^o\chi_{NO}{}^t$, ${}^o\chi_{NO_y}{}^t$, $\chi_{smog}{}^t$ and $^f\chi_{smog}{}^t$ are obtained as described previously and the domain of $^f\chi_{smog}{}^t$ determined according to expression (70). If the value of $^f\chi_{smog}{}^t$ falls outside the range of expression (70) then the nitric oxide and ozone concentrations are calculated according to equations (68) and (69) respectively. When $^f\chi_{smog}{}^t$ falls within the range specified by expression (70) then the rate coefficient for reaction (4) is calculated from the known rate parameters and the temperature measured by sensor 123. The nitric oxide and ozone concentration of air are calculated from the values of $k_3{}^t$, $k_4{}^t$, $\chi_{smog}{}^t$ and $\chi_{NO_y}{}^t$ according to equations (125) and (126) respectively and equation (71) by equations (73) and (74) respectively.

$$\chi_{NO}{}^t \leq \{\chi_{NO_y}{}^t - \chi_{smog}{}^t k_e{}^t/k_4{}^t + [(\chi_{NO_y}{}^t - \chi_{smog}{}^t - k_e{}^t/k_4{}^t)^2 + 4k_3{}^t\chi_{NO_y}{}^t/k_4{}^t]^{\frac{1}{2}}\}/2 \tag{73}$$

$$\chi_{O_3}{}^t = \{\chi_{smog}{}^t - \chi_{NO_y}{}^t - k_3{}^t/k_4{}^t + [(k_e{}^t/k_r{}^t + \chi_{NO_y}{}^t - \chi_{smog}{}^t)^2 + 4k_3{}^t\chi_{smog}{}^t/k_4{}^t]^{\frac{1}{2}}\}/2 \tag{74}$$

(Valid domain for (73) and (74) is when $f_{\chi smog}{}^t$ is in the range $$({}^o\chi_{NO}{}^t - H^o\chi_{NO_y}{}^t) < {}^t\chi_{smog}{}^t < ({}^o\chi_{NO}{}^t + L^o\chi_{NO_y}{}^t) \tag{70}$$

and where expression (70) may be adequately approximated by $$\chi_{NO_y}{}^t({}^oF_{NO} - \tfrac{1}{2}) < '_{smog}{}^t < \chi_{NO_y}{}^t({}^oF_{NO} + \tfrac{1}{2}) \tag{127}$$

The time period required for maximum smog formation in air subsequent to the period of the actual smog formation under selected conditions of temperature and illumination can be determined in the following manner:

The values of ${}^o\chi_{NO_y}{}^t$ and $^f\chi_{smog}{}^t$ are determined as above described and the maximum potential smog concentration of air calculated according to equation (31):

$$^{fmax}\chi_{smog}{}^t = \beta^o\chi_{NO_y}{}^t \tag{31}$$

The amount of further smog formation required ($^{extra}\chi_{smog}{}^t$) to produce maximum smog concentration is calculated according to equation (79):

$$^{extra}\chi_{smog}{}^t = {}^{fmax}\chi_{smog}{}^t - ^f\chi_{smog}{}^t \tag{79}$$

The time period ($t_2 - t_1$) where $t_1$ is the commencement and $t_2$ is the completion time to form the amount of smog equivalent to $^{extra}\chi_{smog}{}^t$ is determined from the rate coefficient for smog formation determined as described above and is calculated for the selected temperature and illumination conditions according to equations (39), (42) and (43) by the solution of equation (80) for ($t_2 - t_1$):

$$^{extra}\chi_{smog}{}^t - \int_{t_1}^{t_2} R_{smog}{}^t I^t e^{-1000\gamma(1/T^t - 1/316)} \, dt = 0 \tag{80}$$

and where a suitable value for $\gamma$ is 4.7.

The time period during which smog formation in air has occurred ($t_t-t_o$), the time period being substantially the same as or within a selected period wherein the end of the selected period coincides with the end of the formation period, can be determined in the following manner. For the duration of selected period the illumination intensity of the air is measured by sensor 124 and the temperature of the air is measured by sensor 123. At the end of selected period ($t_t$) the rate coefficient for smog formation in air, $R_{smog}{}^t$, and the amount of smog formation in air, $^f\chi_{smog}{}^t$, and the amount of prior emissions of $NO_y$ into the air, $^o\chi_{NO_y}$, are determined as described above. The time period ($t_t-o$) is calculated from these values according to equations (27), (39), (42) and (43) by solution of equation (81) for ($t_t-t_o$):

$$^f\chi_{smog}{}^t - \int_{t=o}^{t=t} {}^{T,I}Q_{smog}^t \, dt = 0 \qquad (81)$$

where $$^{T,I}Q_{smog}{}^t = R_{smog}{}^t I^t f(T^t)$$

when $$^f\chi_{smog}{}^t < \beta^o\chi_{NO_y}{}^t$$

or $$^{T,I}Q_{smog}{}^t = 0 \; ^f\chi_{smog}{}^t \lessgtr \beta^o\chi_{NO_y}{}^t$$

and $$f(T^t) = e^{-1000\gamma(1/T^t - 1/316)} \qquad (39)$$

The time period determined by equation (81) is contingent on the premise that all the ROC of the air is present at the commencement of the time period. When this is not the case the determined commencement time $t_o$ is some average of the times during which ROC was introduced into the air. When condition $^f\chi_{smog}{}^t = \beta^o\chi_{NO_y}{}^t$ met during the time period then maximum potential smog formation is reached and the time period determined is a minimum period because the maximum extent of smog formation may have existed for an indeterminate time prior to the end of the selected period.

Optionally if the trajectory and speed of movement of the air during the selected period is known, then the time period during which smog formation has occurred can be used in conjunction with this further information to estimate the location of the source of the ROC emissions, which corresponds to the location of the air at time $t = t_o$.

The time period ($t_t$ to $t_m$) required for production of selected amount of smog in air ($^{select}\chi_{smog}$) under selected conditions of temperature and illumination can be determined in the following manner. The values of $^f\chi_{smog}{}^t$ $^{max}\chi_{smog}{}^t$ and $R_{smog}{}^t$ are determined as above described. The selected amount of smog is tested according to expression (82) to determine if the smog amount selected is within the range of possible smog amounts:

$$^{select}\chi_{smog} \leq (^{max}\chi_{smog}{}^t - {}^f\chi_{smog}{}^t) \qquad (82)$$

If expression (82) is false then the time required for production of selected amount of smog is indefinite because the selected amount is more than the amount that can be produced from the air.

When expression (82) is true then time period ($t_t$ to $t_m$) is calculated by solution of equation (83) for $t_m$:

$$^{select}\chi_{smog} - \int_{t_t}^{t_m} R_{smog}^t I^t e^{-1000\gamma(1/T^t - 1/316)} \, dt = 0 \qquad (83)$$

where $t_t$ is the time at commencement of smog formation and $t_m$ is the time when production of selected amount of smog in air is attained and a suitable value for the coefficient $\gamma$ is 4.7.

The ROC content of air ($\chi_{ROC}{}^t$) can be determined in the following manner. The rate coefficient for smog formation in air $R_{smog}{}^t$ is determined as described above and the value of $\chi_{ROC}{}^t$ calculated according to equation (105)

$$\chi_{ROC}{}^t = R_{smog}{}^t / a_{ROC}{}^t \qquad (105)$$

where for ROC emissions of compositions as commonly found in urban regions a suitable value for $a_{ROC}{}^t$ is $a_{RO}{}^t = 0.0067$ moles smog/mole ROC carbon/unit illumination intensity where illumination intensity has units of rate coefficient for $NO_2$ photolysis integrated with respect to time.

Alternatively the value of $a_{ROC}{}^t$ can be separately determined. The value of $\chi_{ROC}{}^t$ thus determined has units of concentration in air of carbon present as ROC.

The total concentration of ROC previously introduced into air ($^o\chi_{ROC}{}^t$) can be determined in the following manner. The ROC content of air is determined as described above. As to a good approximation the value of the smog forming reactivity of air ($R_{smog}{}^t$) is independent of the amount of illumination to which the ROC/air mixture has been exposed on the day of measurement. The value of $^o\chi_{ROC}{}^t$ can be calculated according to equation (106)

$$^o\chi_{ROC}{}^t = \chi_{ROC}{}^t \qquad (106)$$

The total concentration of $NO_y$ previously introduced into air ($^o\chi_{NO_y}{}^t$) can be determined in the following manner. The values of $\chi_{NO_y}{}^t$, $\chi_{NO}{}^t$ and $\chi_{O_3}{}^t$ are determined for the air as described above and the value of $G^t$ calculated according to equation (58), when $G^t$ has a value of $G^t < 1$ the value of $^o\chi_{NO_y}{}^t$ is calculated from the determined values of $\chi_{NO_y}{}^t$, $\chi_{NO}{}^t$ and $\chi_{O_3}{}^t$ according to equation (59) and where suitable values for the coefficients $P_{7,2}$ and $^oF_{NO}$ are 0.125 and 0.9 respectively or otherwise, when $G^t \lessgtr 1$, from the determined values of $\chi_{O_3}{}^t$ according to equation (60) and where a suitable value for the coefficient $\beta$ is 4.

The total concentration of nitric oxide previously introduced into air ($^o\chi_{NO}{}^t$) can be determined in the following manner. The value of $^o\chi_{NO_y}{}^t$ the air is determined as described above Following equation (11) expressed in terms of concentrations the value of $^o\chi_{NO}{}^t$ is calculated according to equation (109)

$$^o\chi_{NO}{}^t = {}^oF_{NO}{}^o\chi_{NO_y}{}^t \qquad (109)$$

where in most circumstances pertaining to urban air a suitable value for the coefficient $^oF_{NO}$ is 0.9 or alternatively the value of $^oF_{NO}$ can The $NO/NO_x$ concentration ratio of the $NO_x$ introduced into air be independently determined by measurement of the $NO_x$ emissions it their source.

$NO/NO_x$ concentration ratio of the $NO_x$ introduced into air ($^oF_{NO}$) can be determined in the following manner. The concentrations $\chi_{smog}{}^t$, $\chi_{O_3}{}^t$, $\chi_{NO}{}^t$ and $\chi_{NO_y}{}^t$ of the air are determined from the nitric oxide concentrations measured at AI, AII, BI and BII and calculated as described above according to equations (57), (62), (63) and (89) respectively. The temperature of the air at the time of sampling the air is determined by temperature sensor 123 and the sunlight illumination intensity at the time of sampling the air is determined by sensor 124. The value of $^oF_{NO}$ is determined from these values by solution for $^oF_{NO}$ of the set of equations (29) (58) (59) (60), (109) and (68) or (69) or (73) or (74) and where suitable values for the coefficients of these equations are $$P_{7,2}=0.125, \beta=4 \text{ and } H=L=\tfrac{1}{2}$$

The $ROC/NO_x$ concentration ratio Of the total ROC and total $NO_x$ previously introduced into air ($^o\chi_{ROC}{}^t/^o\chi_{NO}{}^t$) can be determined in the following manner. The values of $^o\chi_{ROC}{}^t$ and $^o\chi_{NO}{}^t$ are determined for the air as described above and following equations (10) and (106) the $ROC/NO_x$ concentration ratio can be calculated from the determined concentrations according to equation (108)

$$^o\chi_{ROC}{}^t/^o\chi_{NO_x}{}^t = \chi_{ROC}{}^t/^o\chi_{NO_y}{}^t \qquad (108)$$

The average time of prior introductions of ROC into air ($t_o$) can be determined in the following manner. The time period during which smog formation has occurred ($t_t-t_o$) is determined as described above and the average time of emission of ROC into the air calculated from the time of air sampling ($t_t$) and the duration of the time period during which smog formation has occurred according to equation (113)

$$t_o = t_t - (t_t - t_o) \qquad (113)$$

Figure 5:
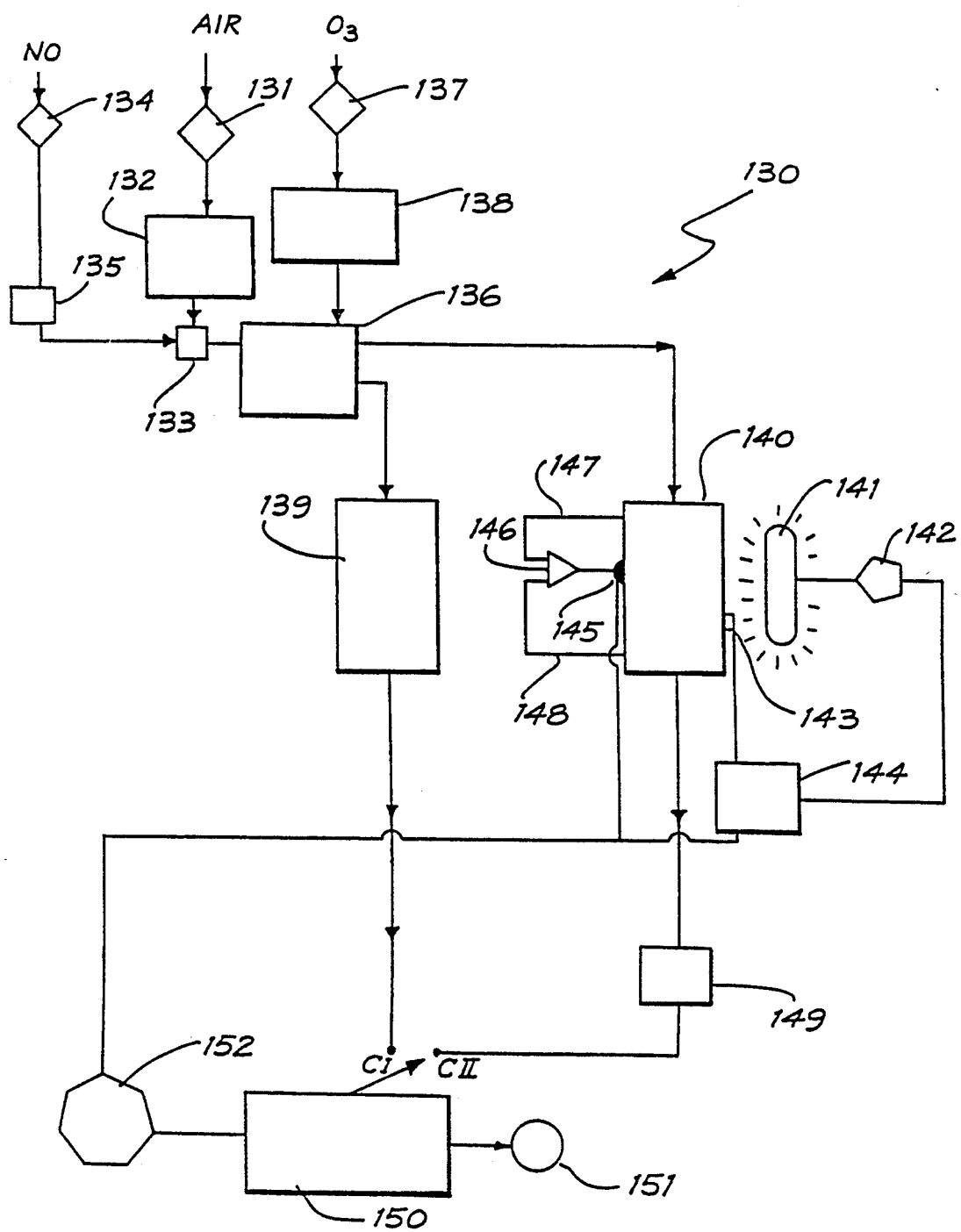
FIG. 5 is a block diagram of a further alternative system for determining rate coefficient of smog formation in air.

Referring to FIG. 5 a system 130 for determining rate coefficient of smog formation in air includes an air filter 131 which filters incoming air and a metered delivery injector 132 which delivers a metered dose of the filtered air to a first combiner 133. A metered dosage of nitric oxide is combined with the filtered air in combiner 133 after passing through nitric oxide filter 134 and being injected therein by metered delivery injector 135.

The nitric oxide/air mixture thus formed is delivered to second combiner 136. A metered dosage of excess ozone is combined with the mixture in combiner 136 after passing through ozone filter 137 and being injected therein by metered delivery injector 138.

As a result an excess ozone/air mixture is formed in combiner 136.

Reactor 139 in which the mixture can react for a first selected period wherein excess ozone in the mixture reacts with substantially all nitric oxide in the mixture is operatively coupled to combiner 136.

Photoreactor 140 is also operatively coupled to combiner 136. Illumination source 141 is operatively disposed about photoreactor 140 to illuminate the mixture in photoreactor 140 for a second selected period under known temperature and illumination conditions. Illumination from source 141 can be kept constant or can be varied according to a preselected or selected illumination profile. Illumination controller/programmer 142 is operatively coupled to source 141 and an illumination sensor consisting of photodiode 143 and photometer 144 for this latter purpose.

Temperature sensor 145 is operatively coupled to photoreactor 140 and temperature controller/programmer 146 to determine the temperature of the mixture in photoreactor 140. The temperature of the mixture in photoreactor 140 can be kept constant during illumination or can be allowed to vary and monitored or can be varied according to a preselected or selected temperature profile by temperature controller/programmer 146 which is operatively coupled to photoreactor 140 via lines 147 and 148.

Reactor 149, in which during a third selected period, excess ozone in the mixture reacts with substantially all nitric oxide is operatively coupled to photoreactor 140.

Ozone analyser 150 is operatively coupled to reactor 139 to determine a first ozone concentration of the mixture after the first selected period at point CI and operatively coupled to reactor 149 to determine a second ozone concentration of the mixture after the third selected period at point CII. The mixture is vented from the system via analyser 150 and vent 151. Computer 152 is operatively coupled to temperature sensor 145, photometer 144 and analyser 150 to calculate the rate coefficient from the first and second ozone concentrations, the known temperature and illumination conditions and the duration of the second selected period.

The rate coefficient of smog formation in air can be determined in the following manner. A metered amount of air is delivered to combiner 33 after passing through filter 131 by injector 132.

Optionally a metered amount of nitric oxide is added to the air in combiner 133 after passing through filter 134 by injector 135 to provide a nitric oxide/air mixture in combiner 133. The nitric oxide/air mixture is delivered to combiner 136. Excess ozone is added to the mixture in combiner 136, after passing through filter 137 by injector 138 to provide a nitric oxide/excess ozone/air mixture in combiner 136. The mixture is split into two streams, one stream being transferred to reactor 139 and the other to photoreactor 140. The mixture is permitted to react in reactor 139 for a first selected period wherein excess ozone in the mixture reacts with substantially all nitric oxide in the mixture. A first ozone concentration of the mixture is then measured by analyser 150 at point CI. The mixture is illuminated in photoreactor 140 for a second selected period under selected and known temperature and illumination conditions. After illumination the mixture is permitted to react for a third selected period in reactor 149. A second ozone concentration of the mixture is measured after the third selected period at point CII by analyser 150. Preferably the duration of the first period is equal to the total duration of the second and third period. The rate coefficient is then calculated by computer 152 from the first and second ozone concentrations, the known temperature and illumination conditions and the duration of the second selected period.

Addition of nitric oxide to air combiner 133 ensures that there is sufficient but small concentration of nitric oxide available in photoreactor 140 to enable reaction (2) not to be limited by insufficient nitric oxide. Smog production is thus to a good approximation equivalent to nitric oxide consumed by reaction (2):

$$RO_2^\cdot + NO \rightarrow NO_2 \quad (2)ps$$

The nitrogen dioxide produced quantitatively by reaction (2) subsequently reacts to produce approximately equivalent ozone by reaction (3)

$$NO_2 + h\nu \xrightarrow{O_2} NO + O_3 \quad (3)$$

Thus smog formation in photoreactor 140 can be measured according to the increase in ozone concentration produced by reaction in the photoreactor. On this basis the rate coefficient is calculated by equations (38) and (84).

$$R_{smog}{}^t = {}^{T,I}Q_{smog}{}^t / I^t f(T^t) \quad (38)$$

where $$f(T^t) = e^{-1000\gamma(1/T^t - 1/316)} \quad (39)$$

and $$\gamma = 4.7$$

and

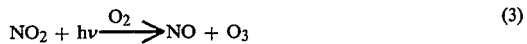
$${}^{T,I}Q_{smog}{}^t = \{[({}^{CI}\chi_{O_3} - {}^{CII}\chi_{O_3}/{}^{II}t](v_{132} + v_{135} + v_{138})/v_{132}\} \quad (84)$$

where $^{CI}\chi_{O_3}$ and $^{CII}\chi_{O_3}$ are the ozone concentrations at points CI and CII respectively, $^{II}t$ is the duration of the second selected period and $v_{132}$, $v_{135}$ and $v_{138}$ are the volumes injected in a specified time by injectors 132, 135 and 138 respectively and I is the illumination intensity and T is the temperature in degrees Kelvin of photoreactor 140.

Figure 6:
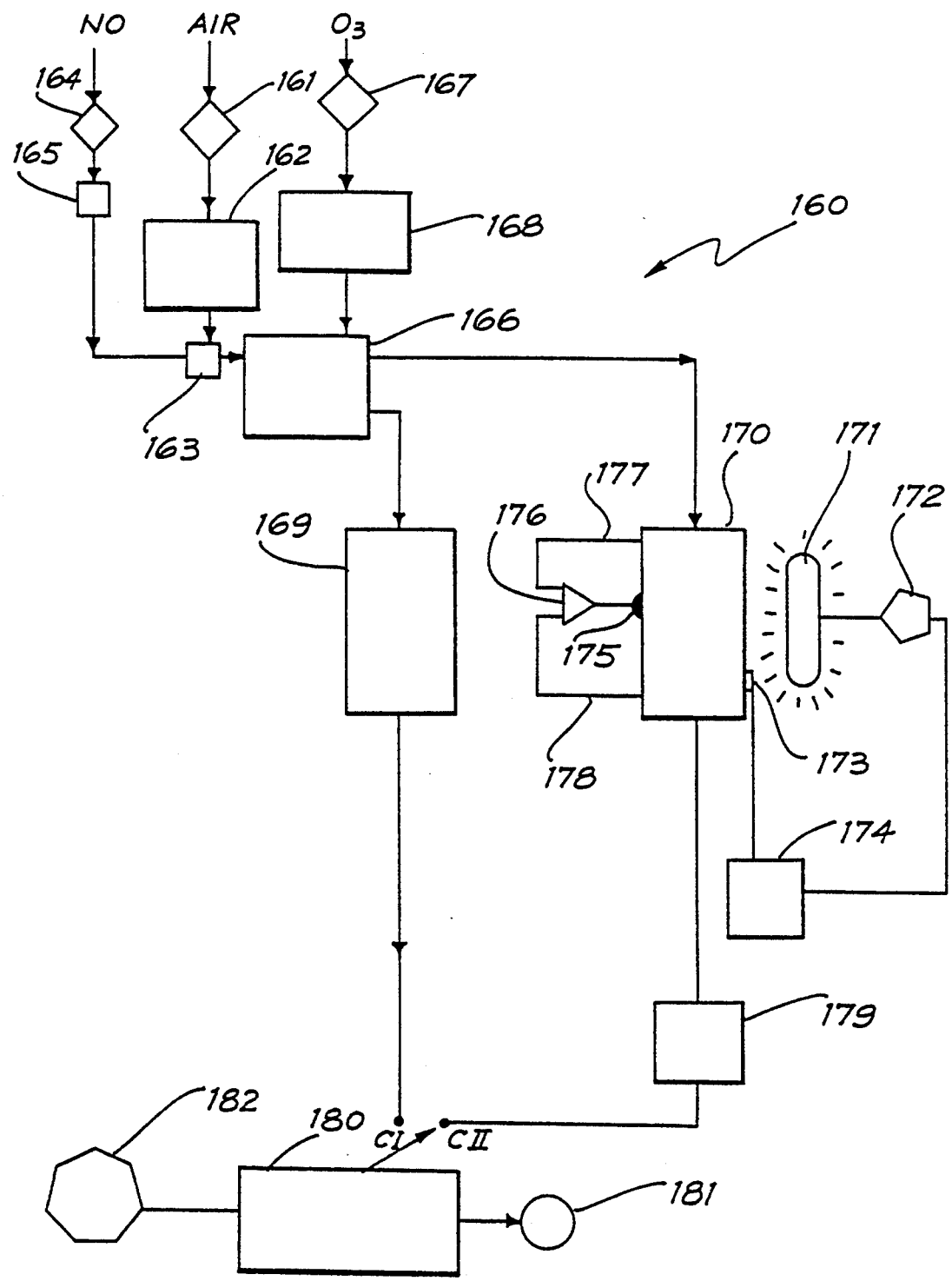
FIG. 6 is a block diagram of an alternative system for determining rate of smog formation in air.

Referring to FIG. 6 a system 160 for determining rate of smog Formation in air under selected temperature and illumination conditions includes an air filter 151 which filters incoming air and a metered delivery injector 162 which delivers a metered dose of the filtered air to a first combiner 163. A metered dosage of nitric oxide is combined with the filtered air in combiner 163 after passing through nitric oxide filter 164 and being injected into combiner 163 by metered delivery injector 165.

First combiner 163 delivers the mixture to second combiner 166. A metered dosage of excess ozone is combined with the mixture in second combiner 166 after passing through ozone filter 167 and being injected into combiner 166 by metered injector 168. A reactor 169 in which the mixture can react for a first selected period wherein excess ozone in the mixture reacts substantially all nitric oxide in the mixture is operatively coupled to combiner 165.

Photoreactor 170 is also operatively coupled to combiner 166. Illumination source 171 is operatively disposed about photoreactor 170 to illuminate the mixture in photoreactor 170 for a second selected period under selected temperature and illumination conditions. Illumination from source 171 can be kept constant or can be varied according to a preselected or selected illumination profile. Illumination controller/programmer 172 is operatively coupled to source 171 and an illumination sensor consisting of photodiode 173 and photometer 174 for this latter purpose.

A temperature sensor 175 is operatively coupled to photoreactor 170 and temperature controller/programmer 176 to determine the temperature of the mixture in photoreactor 170. The temperature of the mixture in photoreactor 170 can be kept constant during illumination or can be allowed to vary and monitored or can be varied according to a preselected or selected temperature profile by temperature controller/programmer 176 which is operatively coupled to photoreactor 170 via lines 177 and 178.

Reactor 179 in which during a third selected period excess ozone of the mixture reacts with substantially all nitric oxide is operatively coupled to photoreactor 170.

Ozone analyser 180 is operatively coupled to reactor 169 to determine a first ozone concentration of the mixture after the first selected period at point CI and operatively coupled to reactor 179 to determine a second ozone concentration of the mixture after the third selected period at point CII. The mixture is vented from the system via analyser 180 and vent 181.

Computer 182 is operatively coupled to analyser 180 to calculate the rate from the first and second ozone concentrations and the duration of the second selected period.

The rate of smog formation in air can be determined in the following manner. A metered amount of air is delivered to combiner 163 after passing through filter 161, and injector 162. Optionally nitric oxide is added to the air in combiner 163 after passing through filter 164, by injector 165 to provide a nitric oxide/air mixture in combiner 163.

The mixture is transferred to a second combiner, combiner 166. Excess ozone is added to the mixture in combiner 166 after passing through filter 167, by injector 168 to provide a nitric oxide/excess ozone/air mixture in combiner 166. The mixture is split into two streams one stream being transferred to reactor 169 and the other to photoreactor 170. The mixture is permitted to react in reactor 169 for a first selected period wherein excess ozone in the mixture reacts with substantially all nitric oxide in the mixture. A first ozone concentration of the mixture is then measured by analyser 180 at point CI. The mixture is illuminated in photoreactor 170 for a second selected period under selected temperature and illumination conditions and further allowed to react for a third selected period in reactor 179 where excess ozone reacts with nitric oxide.

A second ozone concentration of the mixture is measured after the third selected period at point CII by analyser 180. Preferably the duration of the first period is equal to the total duration of the second and third periods. The rate under selected temperature and illumination conditions is then calculated by computer 182 from the first and second ozone concentrations and the duration of the second selected period.

Addition of nitric oxide to air at combiner 163 ensures that there is sufficient but small concentration of nitric oxide available in photoreactor 170 to enable the rate of reaction (2) not to be limited by insufficient nitric oxide. Smog production as measured by ozone formation in photoreactor 170 is thus to a good approximation equivalent to nitric oxide consumed by reaction (2):

$$RO_2^* + NO \rightarrow NO_2 \qquad (2)$$

The nitrogen dioxide produced quantitatively by reaction (2) subsequently reacts to produce approximately equivalent ozone by reaction (3):

$$NO_2 + h\nu \xrightarrow{O_2} NO + O_3 \qquad (3)$$

Thus smog formation in photoreactor 170 can be measured according to the increase in ozone concentration produced by reaction in photoreactor 170. On this basis the rate of smog formation ($^{T,I}Q_{smog}{}^t$) in air under the selected temperature and illumination conditions of photoreactor 170 is calculated according to equation (85):

$$^{T,I}Q_{smog}{}^t = \{[(^{CI}\chi_{O3} - {}^{CII}\chi_{O3})/{}^{II}t][(v_{162} + v_{165} + v_{168})/v_{162}]\} \qquad (85)$$

where $^{CI}\chi_{O3}$ and $^{CII}\chi_{O3}$ are the ozone concentrations at points CI and CII respectively, $^{II}t$ is the duration of the second period and $v_{162}$, $v_{165}$ and $v_{168}$ are the volumes injected in specified time by injectors 162, 165 and 168 respectively.

Figure 7:
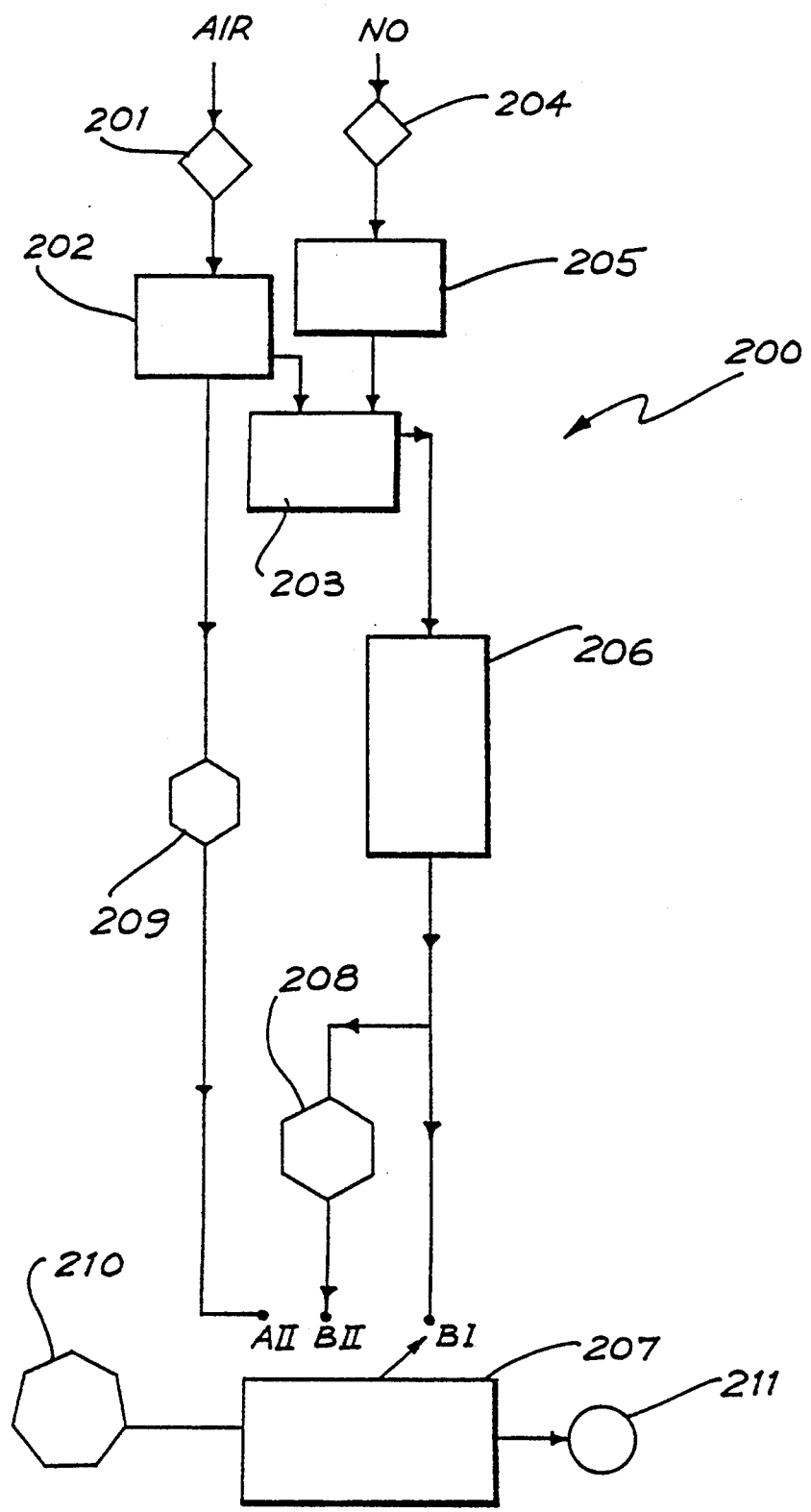
FIG. 7 is a block diagram of a system for determining maximum potential extent of smog formation in air and determining current extent of smog formation in air.

Referring to FIG. 7 a system 200 for determining extent and maximum potential smog formation in air includes an air filter 201 which filters incoming air and a metered delivery injector 202 which delivers a metered dose of the filtered air to combiner 203 and a separate dose of the filtered air to $NO_y$ converter 209. A metered dosage of excess nitric oxide is combined with the filtered air in combiner 203 via nitric oxide filter 204 and metered delivery injector 205. As a result an excess nitric oxide/air mixture is formed in combiner 203.

Reactor 206 in which the mixture can react for a selected period wherein the excess nitric oxide reacts with substantially all ozone the mixture is operatively coupled to combiner 203. Nitric oxide analyser 207 is operatively coupled to reactor 206 to determine the nitric oxide concentration of the mixture at point BI. Analyser 207 is operatively coupled to reactor 206 via converter 208 which converts all the $NO_y$ in the mixture to nitric oxide so that the $NO_y$ concentration of the mixture can be determined as nitric oxide at point BII by analyser 207. The mixture is vented from the system via analyser 207 and vent 211.

Converter 209 is operatively coupled to analyser 207 via point so that the total $NO_y$ concentration of the air can be determined as nitric oxide at point AII. The air is vented from the system via analyser 207 and vent 211.

Computer 210 is operatively coupled to analyser 207 to calculate the maximum potential and extent of smog formation from the determined $NO_y$ and nitric oxide concentrations of the mixture and the $NO_y$ concentration of the air.

The extent and maximum potential smog formation in air can be determined in the following manner. A metered amount of air is delivered to combiner 203 after passing through filter 201 by injector 202. Excess nitric oxide is added to the air in combiner 203 after passing through filter 204, by injector 205 to provide an excess nitric oxide/air mixture in combiner 203.

The mixture is transferred to reactor 206 where it is permitted to react for a selected period wherein excess nitric oxide in the mixture reacts with substantially all ozone in the mixture. The nitric oxide concentration of the mixture is then measured by analyser 207 at point BI. The $NO_y$ concentration of the mixture is measured as nitric oxide after passing through converter 208 at point BII.

A metered amount of air is also delivered to nitric oxide analyser 207 via converter 209. The $NO_y$ concentration of the air is determined at point AII as nitric oxide after passing through converter 209.

The extent ($E_{smog}{}^t$) and maximum potential smog formation ($^{fmax}\chi_{smog}{}^t$) is then calculated by computer 210 from the $NO_y$ concentration of air and the mixture and the nitric oxide concentration of the mixture according to equation (33) and equations (86), (87) and (88):

$$^{fmax}\chi_{smog}{}^t = \beta(^{AII}\chi_{NO}{}^t + P_{7,2}{}^f\chi_{smog}{}^t) \qquad (86)$$

and $$^f\chi_{smog}{}^t = \{[\chi_{smog}{}^t - (1 - {}^oF_{NO})^{AII}\chi_{NO}{}^t]/(1 - {}^oF_{NO}P_{7,2})\} \qquad (87)$$

and $$\chi_{smog}{}^t = [(^{BII}\chi_O - {}^{BI}\chi_{NO})(v_{202} + v_{205})/v_{202}] \qquad (88)$$

where $^{AII}\chi_{NO}$, $^{BI}\chi_{NO}$, $^{BII}\chi_{NO}$ are the nitric oxide concentrations measured at AII, BI and BII respectively and $v_{202}$ is the volume of air injected by injector 202 into combiner 203 and $v_{205}$ is the volume of gas injected by combiner 205 in a specified time and where the values of $\beta$, $P_{7,2}$ and $^oF_{NO}$ are approximated by $\beta = 4$, $P_{7,2} = 0.125$ and $^oF_{NO} = 0.9$ and the extent of smog formation in air ($E_{smog}{}^t$) that is the proportion of smog produced to the maximum potential amount of smog produced is calculated from equation (35):

$$E_{smog}^t = f\chi_{smog}^t / f^{max}\chi_{smog}^t \quad (35)$$

Figure 8:
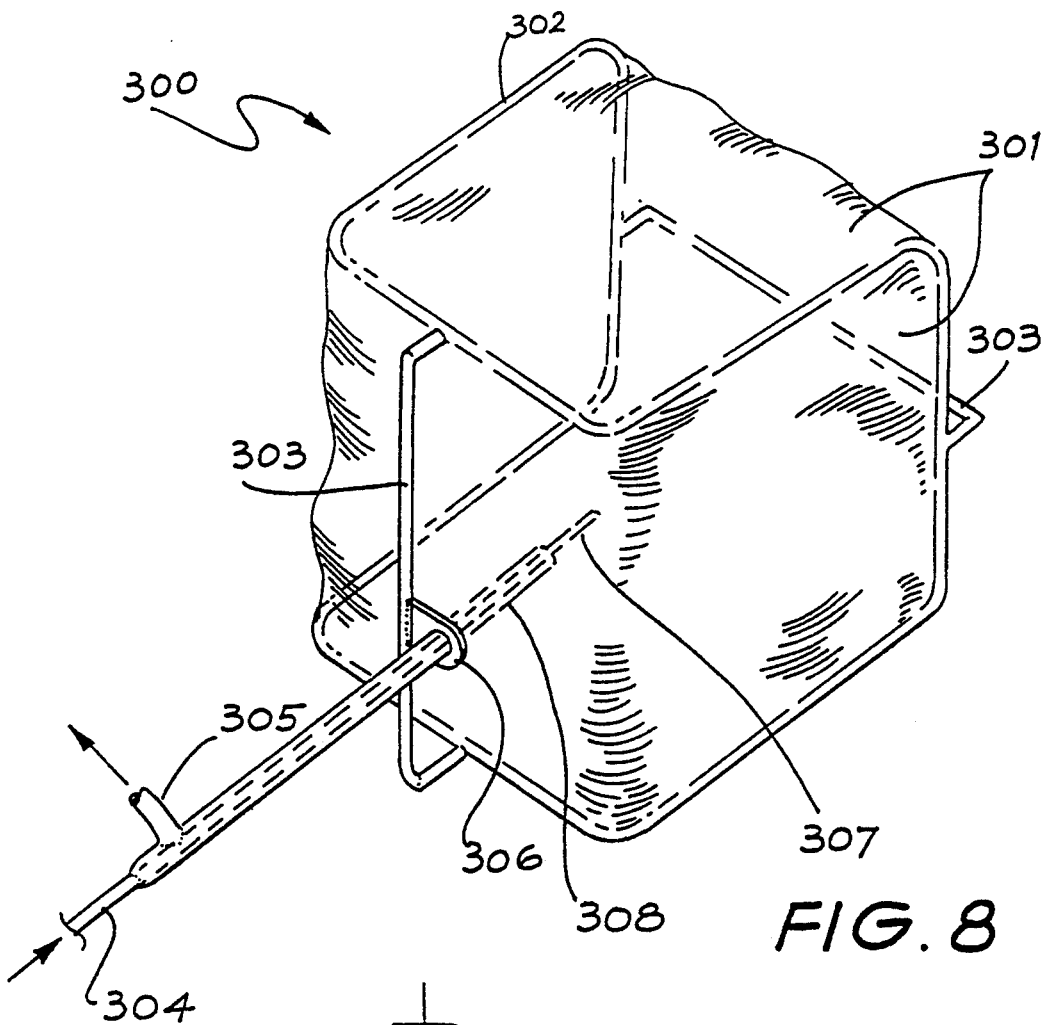
FIG. 8 is a schematic diagram of a preferred photoreactor for use in a system of the invention.
Figure 9:
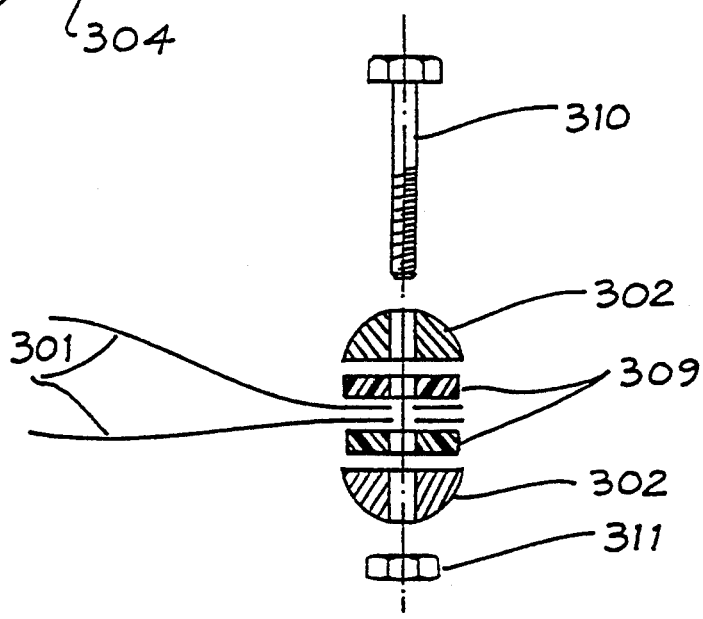
FIG. 9 is a schematic cross-section of the edge of the photoreactor of FIG. 8.

FIGS. 8 and 9 depict a preferred photoreactor for use in a system of the invention and a schematic cross-section of the edge of this photoreactor respectively.

When designing a photoreactor for use in a system of the invention it is desirable to:
 (a) minimise the extent to which chemical reactions occur on the surface of the photoreactor;
 (b) provide for the transmission of both UV and visible light through the walls of the photoreactor;
 (c) ensure that the sample within the photoreactor is well mixed; and
 (d) purge the housing containing the photoreactor with purified air so as to minimize the possibility of contamination of the photoreactor by the ambient or room air and the possible diffusion through the walls and into the photoreactor of reactive species which may be present in the air surrounding the reactor.

Referring to FIG. 8 reactor 300 has walls 301 consisting of two sheets of thin FEP teflon film, supported by and sealed at frame 302. Frame 302 is held by bracing pieces 303. An excess nitric oxide or ozone/air mixture is directed into photoreactor 300 via inlet tube 304 and leaves photoreactor 300 via teflon feed-through tube 305 which penetrates walls 301 at point 306. The excess nitric oxide or ozone/air mixture passes as a jet stream into photoreactor 300 from inlet end 307 and thus stirs the mixture in photoreactor 300. The excess nitric oxide or ozone/air mixture leaves photoreactor 300 via exit end 308. At least a portion of inlet tube 304 fits inside outlet tube 305. This arrangement is particularly satisfactory since only one feed-through port is required in walls 301. Frame 302 retains two gaskets forming a seal and is described in detail below with reference to FIG. 9.

FIG. 9 shows a sectional view of frame 302 which includes two pieces of shaped aluminium D-section rod. Two sheets of FEP teflon film which form reactor walls 301 are held with the inside faces of frame 302 by two gaskets 309 to provide a gas tight seal between reactor film walls 301. The gaskets 309 are formed from sheet elastomeric material, Viton (trade mark) rubber being suitable. The assembly of frame 302, gaskets 309 and reactor walls 301 are secured together by screw fasteners 310 and 311.

The advantage of using FEP teflon film for walls 301 is that it is unreactive. Contact between FEP teflon Film walls 301 and other materials, e.g. metal of frame 302 is minimized in photoreactor 300 thus reducing the extent to which active species can diffuse through walls 301 and contact frame 302 or gaskets 309, undergo reactions and rediffuse back into reactor 300. Further, in photoreactor 300, frame 302 and bracing pieces 303, are minimized in area so as to minimize absorption of radiant energy by frame 302 and pieces 303 thus minimizing heat transferred to the mixture in photoreactor 300. The mixture within reactor 300 is kept well stirred by the jet-like action of the incoming mixture from inlet end 307. The use of only two sheets of FEP teflon film for walls 301 (thickness approximately 0.025 mm) and a single continuous joint minimizes sealing problems that can occur at corner joints. The configuration of photoreactor 300 enables all the mixture in the photoreactor to be simultaneously illuminated thus avoiding dark reactions which could occur if there were shadows cast by frame 302 on the mixture in photoreactor 300. The configuration of photoreactor 300 enables the volume of the photoreactor to be varied after assembly, by adjustment of the length of bracing pieces 303.

Figure 10:
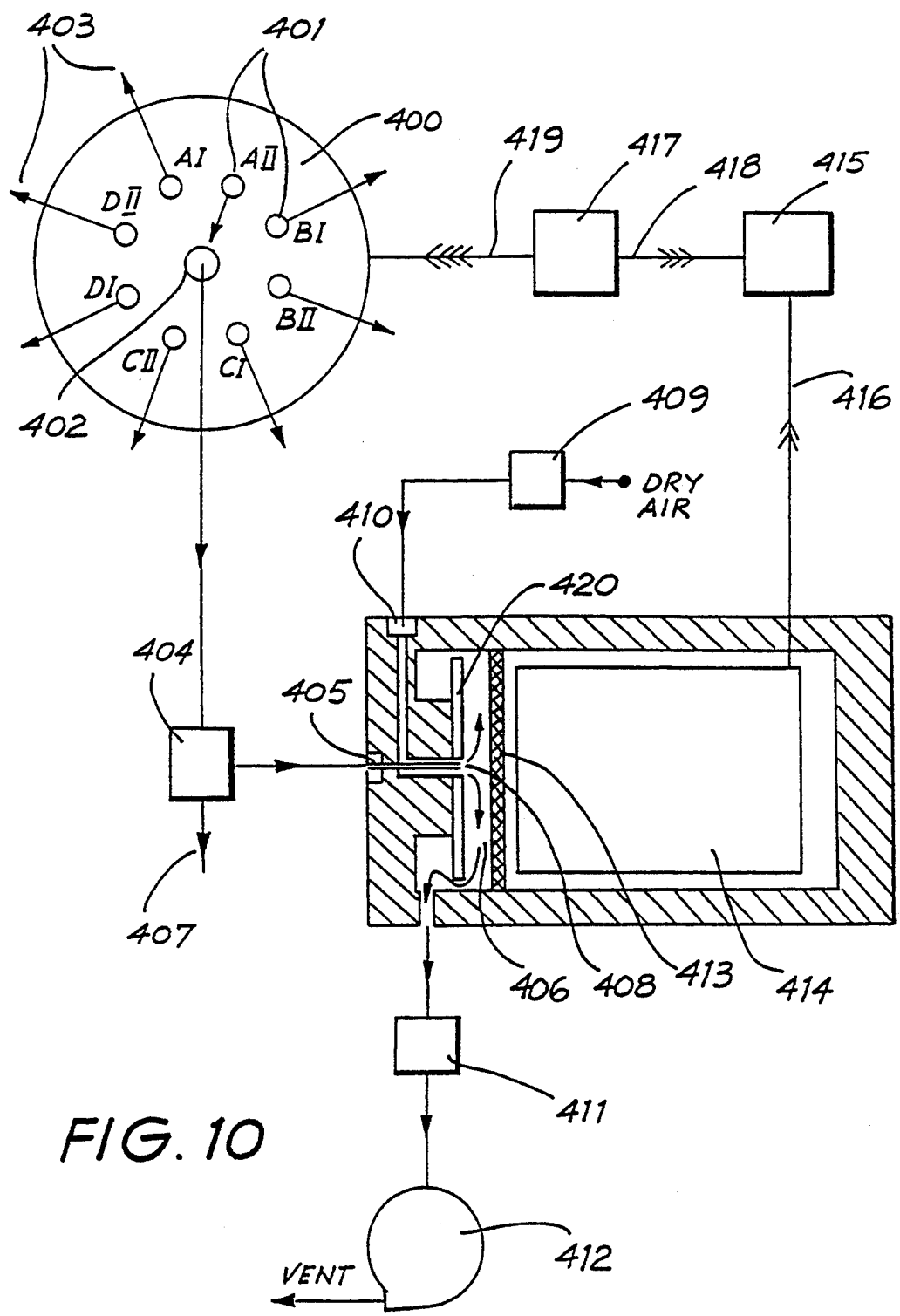
FIG. 10 is a block diagram of a prefer-red nitric oxide analyser.
Figure 11:
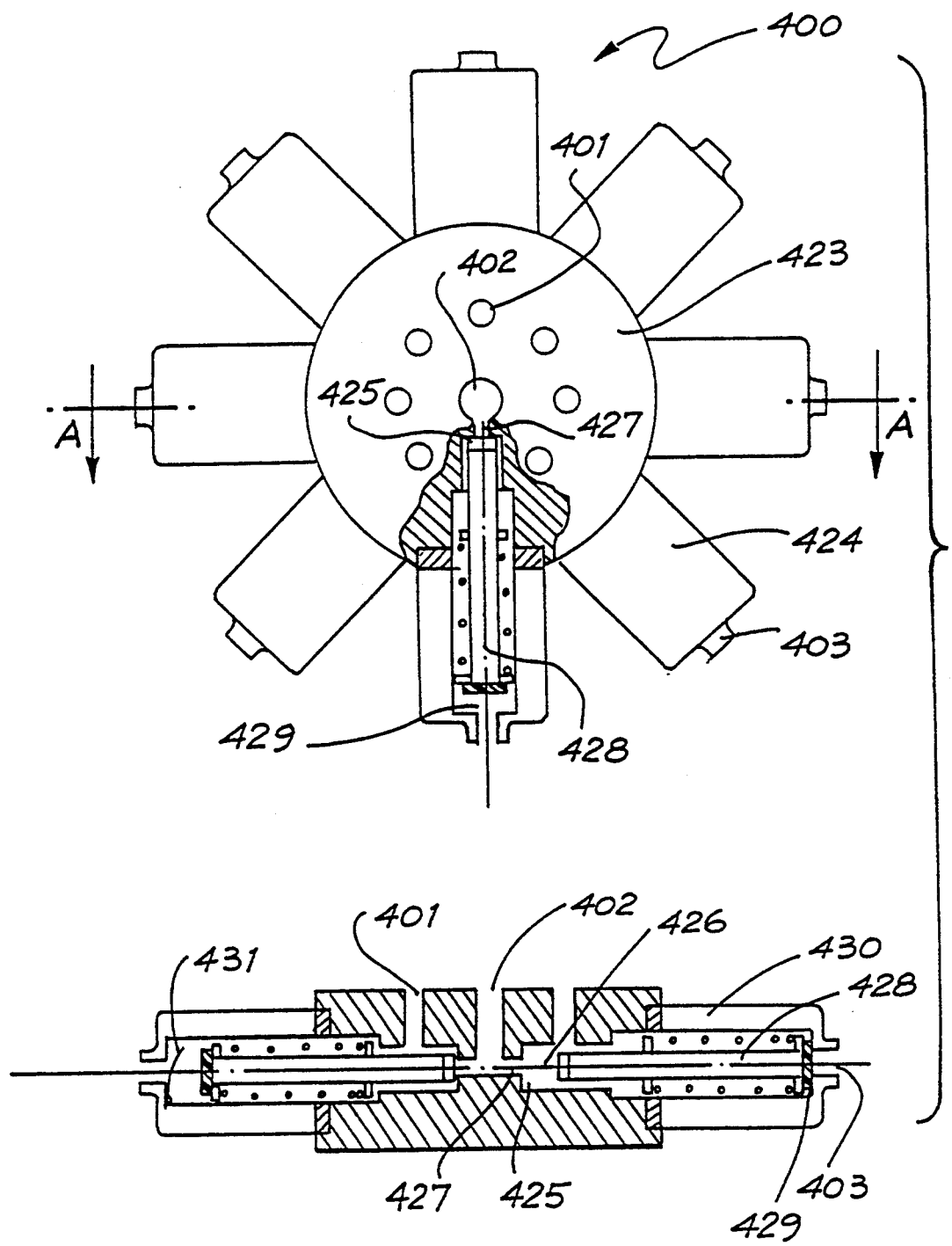
FIG. 11 is partially sectional plan view of the sample selection valve which together with the radial flow chemiluminescent reactor are two components preferably used in the nitric oxide analyser of FIG. 10 as well as a section view along A-A of the plan view.

FIG. 10 depicts a preferred nitric oxide analyser for use in a system of the invention. FIG. 11 depicts a sample selection valve which together with the radial flow chemiluminescent reactor are two preferred components of the nitric oxide analyser of FIG. 10.

When designing a nitric oxide analyser for use in the system of the invention it is desirable to achieve an analyser that is highly sensitive to nitric oxide and to:
 (a) Provide for the rapid switching between samples.
 (b) Minimise the time required to purge the analyser between samples.
 (c) Provide the ability to measure small differences in the nitric oxide concentrations of two sample streams.
 (d) Provide the ability to complete rapidly the analysis of six separate streams (i.e. Streams AI, AII, BI, BII CI, CII).
 (e) Provide means to rapidly zero and calibrate the response of the analyser.

Referring to FIG. 10 the nitric oxide analyser sample stream selection valve 400 has eight inlet ports. The sample and mixture streams of the smog monitor at AI, AII, BI, BII, CI and CII are fed to the corresponding labelled inlet ports 401 of valve 400 as shown in FIG. 10. Nitric oxide-free air is supplied to inlet port DI and a mixture of known nitric oxide concentration is supplied to port DII. Valve 400 has a common outlet port 402 and eight vent ports 403 which are individually connected to their corresponding inlet ports 401. Gas flow from each inlet port is switched to either the outlet port 402 or the corresponding vent ports 403 by means of eight gas switching solenoid valves. The unselected streams freely vent to waste at vents 403 and a single selected steam is delivered from outlet 402 to flow divider 404. Flow metering orifice 405 is connected to flow divider 404 and dispenses a metered flow rate of the selected stream into chemiluminescent reactor inlet 408. Flow in excess of that required by metering orifice 405 supplied to divider 404 and the excess is freely vented to atmosphere at vent 407. A suitable flow at orifice 405 is 750 scc/min. At the inlet 408 to radial-flow chemiluminescent reactor cell 406 the selected and metered stream is mixed with a metered supply of ozonised air which is provided by ozoniser 409 and delivered at a constant flow rate by metering orifice 410 to the reactor inlet 408. The mixture from inlet 408 flows with radial flow pattern through the disc shaped chemiluminescent reaction cell 406, passing between mirrored back plate 420 and optical filter 413. The mixture passes around the edge of the circular mirror plate 420 and is exhausted via activated carbon ozone scrubber 411 by vacuum pump 412 and vented to waste. Light produced in the radial flow chemiluminescent reaction cell 406 by reaction of ozone with nitric oxide passes through optical filter element 413 and is detected by photomultiplier 414. Signal output from photomultiplier 414 is fed to signal processor 415 via line 416. Controller 417 switches stream selection valve 400 via line 419 and the selection is communicated to signal processor 415 via line 418.

An advantage of the disc shaped radial flow chemiluminescent reaction cell is that for a given cell volume the system has the minimum gas mixture residence time and provides rapid purge out of the cell when a new sample stream is selected at valve 400. This arrangement also provides good optical coupling with the photocathode of the photomultiplier. Utilization of mirror backed glass disc back plate 420 in the reaction cell 406 further enhances the intensity of light collected at the photocathode of photomultiplier 414. A suitable dimension for the reaction cell 406 is 6 mm by 55 mm diameter and typically the cell is operated at a pressure of 1/10 atmosphere or less and which is maintained by vacuum pump 412.

FIG. 11 shows a schematic representation of a preferred sample stream selection valve 400, a component part of the nitric oxide analyser. Valve 400 has a stainless steel body 423 and eight inlet ports 401 disposed symmetrically about a centrally located common outlet port 402. Each inlet port 401 is connected with an associated vent port 403 and also to the outlet port 402 via outlet manifold 426. Flow from inlet ports 401 is directed either to manifold 426 via valve seats 425 when 425 is open or to vent ports 403 when valve seat 425 is closed. The valve plunger 428 is activated by solenoid 430 and can take up two positions:

(1) normally closed;
valve seat 425 is closed and valve seat 429 is open to allow flow from inlet port 401 to vent freely to atmosphere via the corresponding vent 403; and
(2) open;
solenoid 430 is energised, plunger 428 is withdrawn against return spring 431 to close valve seat 429 to open seat 425, directing flow from inlet 401 via drilling 427 to manifold 426 and out of the valve body 423 via common outlet port 402.

The volume of manifold 426 is small as also is the volume of the valve seat to manifold drillings 427. The drillings 427 are short to minimize dead volume and to ensure rapid purging of the manifold assembly when flow streams are switched by the action of the solenoids 430.

In operation each stream flows through its respective inlet port 401 into valve body 423. Only one solenoid 430 is energised at any time. The stream with the energised solenoid passes out of the valve via valve seat 425, drilling 427 manifold 426 and outlet port 402. The stream of the unenergised solenoids flow freely through their respective solenoid valves passing plungers 428 and valve seat 429 to vent at vent 403. Inlet ports 401 are disposed close to their corresponding valve seats 425 thus ensuring that when unenergised each solenoid valve is continuously well purged with the gas stream.

An advantage of this design of valve 400 is that it enables several streams to be independently and rapidly switched into a common manifold. Because the volume of manifold 426 is small and drillings 427 are short the dead volume of the system between valve seats 425 and outlet port 402 is small. Thus the gas of any selected stream is rapidly displaced from manifold 426 by the next selected stream when the solenoid selection is changed. Bleed of the previous sample from drillings 427 into the newly selected stream is minimised by making drillings 427 short. Thus stream selection valve 400 requires only a very short time period to completely purge out with each newly selected stream.

The outlet port 402 is connected to chemiluminescent reaction cell 406 via stream divider 404 by short lengths of tubing of small volume.

The advantage of using a radial flow chemiluminescent reaction cell coupled with small dead volume stream selection valve 400 is that it enables the nitric oxide analyser of FIG. 10 to be rapidly switched from sample stream to stream with minimum time required between measurements for purge out of the previous sample stream from the analyser before commencment of measurement of the newly selected stream.

The advantage of rapidly switching between streams is that when the nitric oxide concentration difference between streams is to be determined and the composition of the air sampled by the smog monitor is variable the error in the concentration difference measurement is minimised when the time difference between the measurement of each stream is minimised.

The nitric oxide analyser is operated in the following manner. Stream selection is controlled by controller 417 which selects streams according to the following routine, activating the selected solenoids of valve 400 via communication line 419. Controller 417 operates two kinds of cycles, X and Y. Cycle X provides analysis of streams AI through to CII. The time taken for analysis of each stream is composed of the time required to purge the previous stream from the analysis system (time period m) and a second period when the uncontaminated stream is analysed for a time period equal to an integral multiple of time period n. Cycle X has the sequence:

AI(m,n), AII(m,n), BI(m,n), BII(m,n), CI(m,n), CII(m,2n), CI(m,n)

where AI(m,n) denotes stream AI selected and for period m+n.

During time period m the nitric oxide analyser is purged by the newly selected AI stream without data processor 415 recording the output from the photomultiplier 414.

Following completion of period M controller 417 activates data acquisition by data processor 415 of output signal from photomultiplier 414 for a period n. On completion of the n time period controller 417 stops acquisition of data by 415 and immediately deselects port AI and selects port AII valve 400 and similarly through the rest of the cycle, except that for CII measurement data is acquired for a period of duration 2n.

Cycle Y contains the same sequence as cycle X but in addition includes selection of either port DI or DII.

Cycle Y has the sequence:

AI(m,n), AII(m,n), BI(m,n), BII(m,n), CI(m,n),
CII(m,2n), CI(m,n), D[I or II](m,n)

A suitable time for completion of either cycle X or Y is 45 seconds and a suitable value for m is 0.714 seconds.

The duration of period n is different from cycles X and Y.

For cycle X, m=5.0 seconds and for cycle Y, m=4.36 seconds.

Typically the smog monitor operates with controller 417 directing completion of three X cycles followed by a Y cycle every fourth cycle, with stream DI being activated during the Y cycle, thus providing a zero NO concentration reference point for the nitric oxide analyser.

From time to time the nitric oxide analyser is calibrated, typically once per day, by substitution of one of the X cycles every fourth cycle by a Y cycle wherein stream DII is selected. Port DII of valve 400 is provided with a calibration gas mixture of known nitric oxide concentration during the period of the calibration which is typically 15 minutes.

The advantages of this arrangement are:

The nitric oxide analyser can be zeroed and calibrated without interruption to the analysis of streams AI to CII.

Analysis of all the required streams is rapidly completed in the space of 45 seconds. Rapid completion of the measurement cycle minimises the likelihood that the composition of the air being sampled and analysed will vary significantly during the course of a single cycle, thus minimising the error in the values determined for the nitric oxide concentration difference between streams.

It is desirable to determine the nitric oxide concentration difference between streams CI and CII to higher accuracy than is required for the AI, AII and BI, BII concentration differences. The analyser provides very accurate measurement of small nitric oxide concentration differences between stream CI and CII by devoting proportionally greater time to measurement of these streams and by measuring the CI stream both immediately before and immediately following the CII measurement.

AN EXAMPLE OF THE INVENTION AND APPLICATION TO PHOTOCHEMICAL SMOG MONITORING

Figure 12:
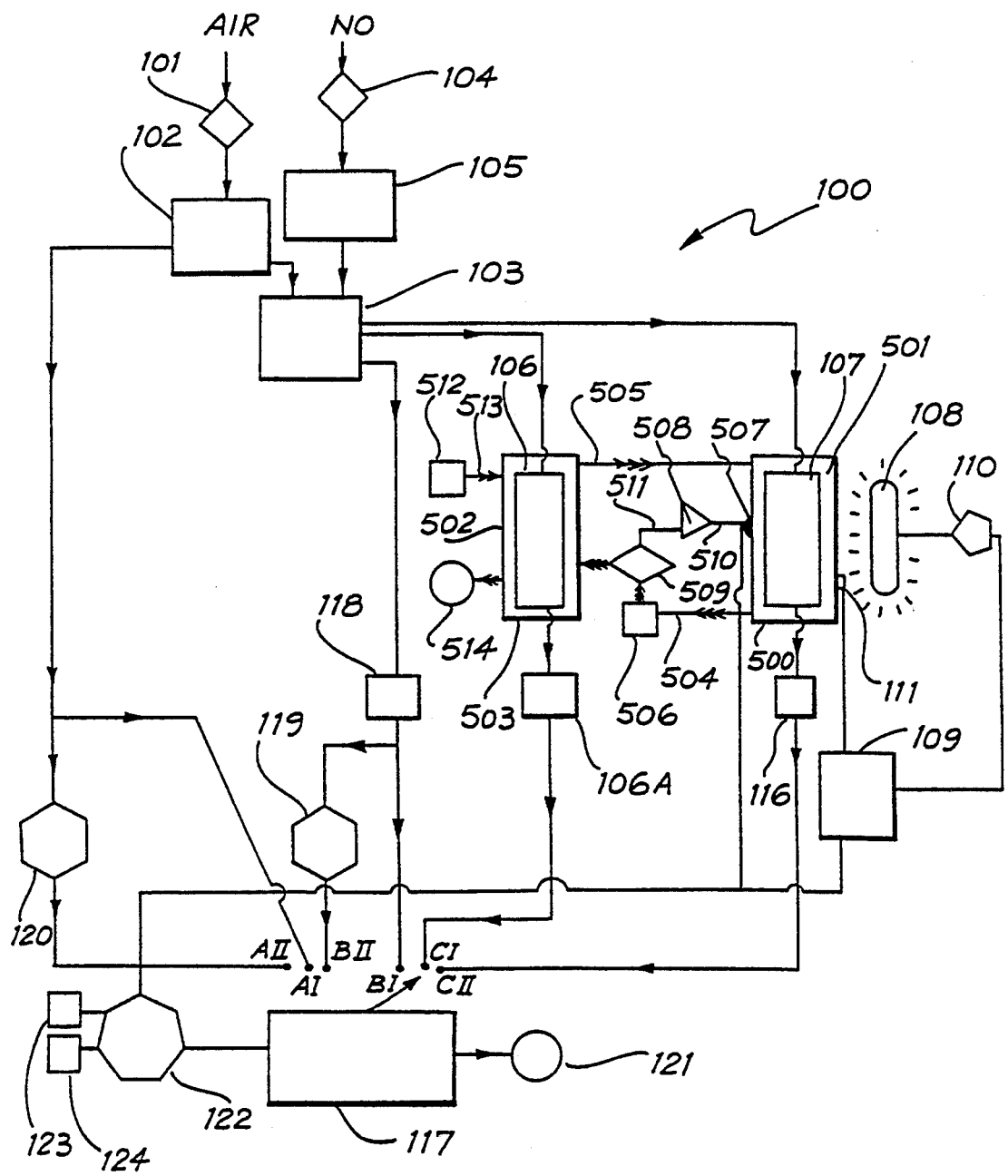
FIG. 12 is a block diagram of a system similar to the system depicted in FIG. 4 and which was used in an Example run.

An example of system 100 was fabricated substantially in accordance with that described with reference to FIG. 4 and as shown in FIG. 12.

Reactor 107 was fabricated from FEP (Trade Mark) Teflon film (registered Trade Mark) with an internal volume of 17 liters.

Reactors 116 and 118 were of identical construction, which consisted of a PTFE Teflon pipe or internal diameter 40 mm and length 1000 mm (Volume 1.26 liters), with end closures of PTFE teflon and with mixture inlet and outlet at opposing ends, Reactors 106 and 106A were a combination of reactors identical with the configuration of reactors 107 and 116 respectively.

Illumination source 108 was a combination of several fluorescent UV lights with light output rich in the UVA region of the spectrum together with white light fluorescent lamps. Illumination intensity was kept constant when the system was in operation. Source 108 had a total power consumption of 440 watts.

Twenty two fluorescent lamps 108 were disposed about photoreactor 107.

The lamps are separated from photoreactor 107 by an airtight FEP Teflon film window 500. Photoreactor 107 is located centrally within airtight chamber 501 formed by window 500. Reactor 106 is surrounded by an opaque airtight housing 502 forming chamber 503 about reactor 106 and housing 502 is connected to chamber 501 by two ventilation lines 504 and 505. Line 504 included blower 506 to circulate purified air between chambers 501 and 503.

Heat exchanger 509 is mounted in the circulating purified air flow. The temperature within chambers 500 and 502 is sensed by temperature sensor 507 and the temperature of the purified air controlled to a selected temperature by controller 508 and heat exchanger 509. Temperature sensor 507 is linked to controller 508 by line 510 and temperature controller 508 to heat exchanger 506 by line 511.

The temperature was selected on the basis of being as warm as was compatible with smog formation under the ambient conditions to be measured, so as to cause the rate of reactions in photoreactor 107 to be sufficiently fast, the sensitivity of measurement of rate of smog formation being greater the higher the temperature (and light intensity) of photoreactor 107. The maximum temperature desirable is limited by the onset of reactions which do not take place in the atmosphere.

On these grounds the selected temperature was 40° C.

Maintaining the temperature of reactors 106 and 107 warmer than that of the air to be measured minimizes the likelyhood of condensation of water or reaction products onto the walls of reactors 106 or 107.

A supply of purified air was provided by air purifier 512 (AADCO 737 series, AADCO, Inc., 2257 Lewis Avenue, Rockville, Md. 20851, U.S.A.) and supplied to housing 503 via line 510 and excess air freely exhausted from chamber 503 and vent 514. By purging chambers 503 and 501 with purified air, photoreactor 107 is maintained in an environment with minimal ROC and $NO_y$ concentrations, thus reducing the likelihood of contamination of reactor 106 and photoreactor 107 by air of the room within which system 100 was located, including diffusion of reactive contaminants through the FEP Teflon film walls.

The materials of fabrication of all components were chosen on the basis that there would be minimum outgassing therefrom. For example, materials with plasticizers were not employed.

Teflon insulated wires were used to link the sensors in system 100 and Teflon tubes were used to link the components with the reactors of system 100.

Reactors 106 and 107 were maintained at a common constant temperature of 40° C. by temperature controller 508.

Nitric oxide gas was supplied to filter 104 as a mixture of about 800 ppm nitric oxide in nitrogen and was injected by metered delivery injector 105 at a constant rate of 1.8 ml per minute.

The flowrate of mixture through reactor 118 was maintained at 0.38 liters/min and through reactors 106 and 106A, and photoreactor 107 and reactor 116 at 1.47 liters/min.

Analyser 117 was capable of determining nitric oxide concentration of two gas streams simultaneously and computer 122 calculated the concentration and concentration difference of each pair of streams AI and AII, BI and BII or CI and CII. Analyser 117 was configured to determine nitric oxide concentration at points AI and AII for approximately 5 minutes, then at BI and BII for five minutes and then at CI and CII for a further five minutes and then continue by repeating the cycle indefinitely.

The residence time of mixture flowing in plug flow through reactor 118 was approximately 3.3 minutes and the residence time of mixture in well stirred photoreactor 107 was 11.6 minutes and residence time reactor 116 under conditions of plug flow, 0.86 minutes. The residence time of mixture in reactors 106 and 106A was equal to the sum of the residence times of reactors 107 and 116, namely 12.6 minutes. Thus because of the differing residence time for streams emerging at AI, AII, BI, BII, CI and CII to pass through system 100 via the various flow paths from filter 101 to analyser 117 and the sequential analysis of air and mixture passing points AI, AII, BI, BII, CI and CII, the air and mixture measured at points AI, AII, BI, BII, CI and CII within any one analyser cycle represented separate sub samples of air which passed as a single sample through filter 101.

Thus to a fair approximation, analyses made at points AI, AII, BI, BII, CI and CII within the one nitric oxide analyser measurement cycle represent separate analyses of the same air. This is advantageous when the composition of air entering filter 101 is variable, as is frequently the case when ambient air is monitored.

In this example of the operation of system 100 it was located in the rural outskirts of a major city, approximately 16 km from the central business district and some kilometers from any known strong source of ROC or nitrogen oxides emissions. The topography of the region was generally flat, with no significant mountains or hills. The locality is known to be subject periodically to episodes of photochemical smog. The atmosphere at the location was sampled directly into filter 101.

The illumination intensity in photoreactor 107 provided by source 108 was determined by calibration of the system in the following manner.

Pure air, free of ROC and nitrogen oxides, was supplied throughout the calibration procedure to filter 101. The system was operated as described for smog monitoring until steady and equal nitric oxide concentrations were measured by analyser 117 at points CI and CII. Cycling of analyser 117 was then reprogrammed so that points CI and CII were measured frequently for the remaining duration of the calibration procedure. A known small amount of ROC ($^o n_{ROC(std)}$) of known smog forming activity ($a_{ROC(std)}$) was then rapidly introduced into the purified air entering filter 101. The nitric oxide concentration at CI and CII was analysed by analyser 117 for a period of an hour after introduction of the ROC mixture.

The ROC mixture employed as the calibration standard and introduced at filter 101 consisted of a mixture of gaseous alkane, alkene and alkyne hydrocarbons and had an activity coefficient for smog formation value of $$a_{ROC(std)} = 0.016 \text{ moles smog/mole ROC/unit illumination/unit } f(T)$$

where illumination is expressed in units of $\int k_3 \cdot dt$, $k_3$ being the rate coefficient for $NO_2$ photolysis. The mean molecular weight of the ROC(std) mixture was:

$$\overline{MW}_{ROC(std)} = 31.8 \text{ g}$$

An amount of $1.53 \times 10^{-4}$ g of the ROC calibration standard was introduced into system 100 at filter 101 giving an initial amount of ROC in photoreactor 107 of $7.00 \times 10^{-5}$ g ($2.20 \times 10^{-6}$ moles) which was then subject to continuous dilution by the flow of ROC-free mixture through photoreactor 107 and to photoreaction by illumination provided by source 108. These processes can be described by the mechanism:

$$ROC \xrightarrow{\text{dilution}} \text{lost } ROC \tag{90}$$

$$ROC \xrightarrow{h\nu, NO} ROC + \text{Smog} \tag{91}$$

$$SMOG \xrightarrow{\text{dilution}} \text{lost Smog} \tag{92}$$

where the rate coefficients for dilution of ROC ($k_{90}$) and dilution of smog ($k_{92}$) are equal, i.e.:

$$k_{90} = k_{92} \tag{93}$$

thus the smog concentration in photoreactor 107 after introduction of the calibration standard at time t=O, is described by $$\frac{d\chi^t_{smog}}{dt} = k_{91} \chi^t_{ROC} - k_{92} \chi^t_{smog} \tag{94}$$

and $$-\frac{d\chi^t_{ROC}}{dt} = k_{90} \chi^t_{ROC} \tag{95}$$

Integration of (95) equation yields $$\chi_{ROC}{}^t = \chi_{ROC}{}^{t=o} e^{-k_{90} t} \tag{96}$$

Substitution of expression (96) for $\chi_{ROC}{}^t$ in equation (94) and $k_{90}$ for $k_{92}$ and integrating gives:

$$\chi_{smog}{}^t = k_{91} \chi_{ROC} t e^{-k_{90} t} \tag{97}$$

Now the rate coefficient for exponential dilution, ($k_{dil}$) is given by:

$$k_{dil} = f/V \quad (98)$$

where f is the flowrate and V the volume of the vessel. Therefore for photoreactor 107 under the conditions of the calibration:

$$k_{90}k_{92} = 1.47/17 = 8.52 \times 10^{-2} \, \text{min}^{-1}$$

Now by design and under the specified operating conditions of system 100 the smog concentration produced by photoreaction in photoreactor 107 is equivalent to the difference in nitric oxide concentrations between the corresponding mixture from reactor 106A when measured at CI and the mixture From reactor 116 measured at point CII:

$$\chi_{smog}^t = {}^{CI}\chi_{NO}^t - {}^{CII}\chi_{NO}^t \quad (99)$$

Substitution of the expression (99) into equation (97) yields, for the calibration:

$$^{CI}\chi_{NO}^t - {}^{CII}\chi_{NO}^t k_{91}\chi_{ROC}^{t=0} t e^{-k_{90}t} \quad (100)$$

Thus for calibration the value of $^{CI}\chi_{NO}^t - {}^{CII}\chi_{NO}^t$ indicated by computer 122 is proportional to the value of $te^{-k_{90}t}$ and the plot of $(^{CI}\chi_{NOt=o}^t - {}^{CII}\chi_{NO}^t)$ versus $te^{-k_{90}t}$ has the gradient of $k_{91}\chi_{ROC}^{t=o}$, where in the present case $k_{90}$ has the value $8.52 \times 10^{-2} \, \text{min}^{-1}$ and t is the time duration after introduction of the ROC calibration mixture into photoreactor 107. For the case of this example the values obtained for these quantities at various elapsed times are listed in Table 1 and are plotted in FIG. 13, which also shows the line of best fit, which has a gradient of 0.0139 and intercept of 0.0029.

To a fair approximation and to the precision of analyser 117 the data of Table 1 fall on a straight line. This indicates that:

(1) Rate of smog formation is independent of the duration of the reactions involving ROC.
(2) Rate of smog formation is proportional to the amount of ROC present in air.
(3) Processes occurring at the walls of the reactors 106, 106A and 116 and photoreactor 107 do not contribute significantly to the chemical dynamics of the system.

The line of best fit passes close to but not through the origin, this intercept is attributable to small errors in the estimation of the initial time and the initial inhomogeneity of ROC distribution in photoreactor 107 immediately on introduction of the ROC calibration mixture.

Figure 13:
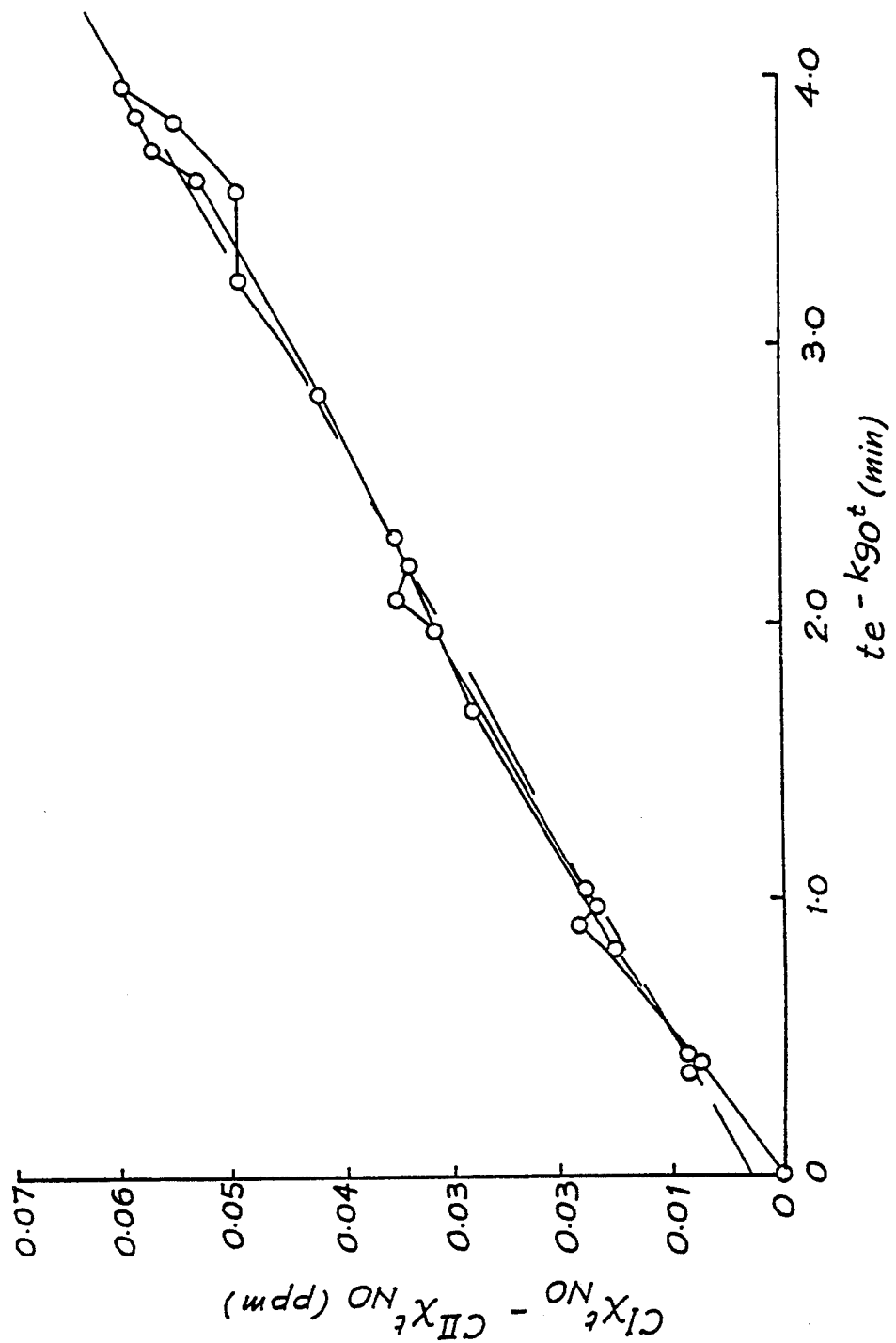
FIG. 13 is a plot of $^{CI}\chi_{NO^t} - ^{CII}\chi_{NO^t}$ vs $te^{-k90^t}$ which was used to calibrate the illumination source of the system depicted in FIG. 12.

Thus by equation (100) and the gradient of the graph of FIG. 13

$$k_{91}\chi_{ROC}^{t=o} = 0.0139 \times 10^{-6} \, \text{mole fraction min}^{-1} \quad (101)$$

An alternative to determination of $k_{90}$ by measurement of photoreactor 107 volume and flowrates is available by application of data from Table 1.
When $$\chi_{smog}^{t(1)} = \chi_{smog}^{t(2)}$$

then $$k_{90} = (\ln t(2) - \ln t(1))/(t(2) - t(1)) \quad (102)$$

where t(1) and t(2) are any two times (t(2)>t(1)) when the respective smog concentrations of photoreactor 107 are equal.

An advantage of calibration by introduction of ROC into system 100 as described is that the system performance over a wide range of ROC concentrations can be evaluated. In the case of this example the quantity of ROC initially present in photoreactor 107 was, in terms of concentration, 7.70 ppmC (where ppmC denotes mole carbon X $10^6$/mole mixture). After 59 minutes, dilution reduces this concentration in photoreactor 107 to 0.050 ppmC.

Now by definition the rate of smog formation in photoreactor 107 ($^{T,I}Q_{smog}^t$) is given by:

$$^{T,I}Q_{smog}^t = k_{91}\chi_{ROC}^t \quad (103)$$

where T and I are the temperature and illumination intensity respectively of photoreactor 107. From (101) and (103) therefore, $^{T,I}Q_{smog}^{t=0} = 0.0139 \, \text{ppm.min}^{-1}$ for the conditions of the calibration.

Now also for the conditions of photoreactor 107 and by equations (38) (39) and (41) $^{T,I}Q_{smog}^t$ is also given by:

$$^{T,I}Q_{smog}^t = \frac{RT^t}{p^t V^t} I^t e^{-1000\gamma(1/T - 1/316)} \sum_{i=1}^{n} (a_{ROC(i)}{}^o n^t_{ROC(i)}) \quad (104)$$

Substitution of the calibration value for $^{T,I}Q_{smog}^{t=0}$ into equation (104) and from the known values of the other terms and where i = ROC calibration mixture the illumination intensity $I^t$ is determined.

$$I^t = \frac{0.0139 \times 10^{-6} \times 1 \times 17 \times e^{-4700(1/313 - 1/316)}}{0.08206 \times 313 \times 0.016 \times 2.20 \times 10^{-6}}$$

$$= 0.227 \, \text{min}^{-1}$$

That is the value of $k_3$ for photoreactor 107 and illumination source 108 assembly is determined to be 0.227 $\text{min}^{-1}$.

The calibration procedure as described is also suitable for determining the value of the activity coefficient for smog formation ($a_{ROC}$) of particular ROC or ROC mixtures. This is accomplished by first determining the value of $I^t$ for the photoreactor 107 then introducing a known quantity of the ROC/ROC mixture to be evaluated as for the ROC calibration mixture during calibration. The value of $a_{ROC}$ is then determined from the measurements by evaluation of equation (104) using the known value of $I^t$.

System 100 was installed at the described location and operated to monitor throughout a day smog in the atmosphere, analysing air continuously sampled over the period 0958 to 1654 hours. The temperature of the atmosphere and the sunlight intensity was measured by sensors 123 and 124 respectively for the same day for the selected period of 0622 to 1826 hr, these times corresponding approximately with dawn and dusk. The values for the temperature and sunlight intensities at selected times throughout the day are given in Table 2. The nitric oxide concentrations measured by analyser 117 at points AI, AII, BI, BII, CI and CII and the corresponding time of sampling the air (t) are listed in Table 3. The rate of smog formation ($^{T,I}Q_{smog}{}^t$) for air within photoreactor 107 was calculated according to equations (55) and (56) and where $^I\chi_{NO}$ and $^{III}\chi_{NO}$ of equation (55) correspond to $^{CI}\chi_{NO}{}^t$ and $^{CII}\chi_{NO}{}^t$ of Table 3 and T and I are the temperature and illumination conditions within photoreactor 107 Values of $^{T,I}Q_{smog}{}^t$ determined for each measurement time are listed in row 8 of Table 3. Instrument transients can give rise to spurious values for $^{T,I}Q_{smog}{}^t$ as is illustrated by the negative value obtained in Table 3 for time 1044.

The rate coefficient for smog formation $R_{smog}{}^t$ is calculated from the known temperature and illumination conditions of photoreactor 107 and the value of $^{T,I}Q_{smog}{}^t$ by equations (38) and (39). The results are expressed as $R_{smog}{}^t \times 10^4$ and for each example measurement are listed in row 9 of Table 3 where the units of $R_{smog}{}^t$ are ppm smog/unit of incident light/unit f(T) where the incident light intensity is expressed as the rate coefficient for NO2 photolysis ($k_3$).

The concentration of smog in air $\chi_{smog}{}^t$ is calculated by equation (57). Values of $^{BI}\chi_{NO}$ and $^{BI}\chi_{NO}$ are listed in Table 3, rows 4 and 5, and, for system 100 as employed, $v_{102} = 1.47 + 1.47 + 0.38 = 3.38$ liter min$^{-1}$ and $v_{105} = 1.8 \times 10^{-3}$ liter min$^{-1}$. The values of $\chi_{smog}{}^t$ determined for each measurement time are listed in row 10 of Table 3.

The NO$_y$ concentration of air is measured as nitric oxide at point AII. For this example the values obtained ($^{AII}\chi_{NO}{}^t$) are listed in Table 3, row 3, and are also listed as the NO$_y$ concentrations at the time of air sampling ($\chi_{NO}{}^t$) in row 11 of Table 3.

The nitric oxide concentration of air is measured at Point AI and the values obtained ($^{AI}\chi_{NO}{}^t$) are listed In Table 3 row 2, and are also listed in row 12, Table 3, as the nitric oxide concentrations at the time of air sampling ($\chi_{NO}{}^t$).

The ozone concentration of air is calculated from the values of $\chi_{smog}{}^t$, $\chi_{NOy}{}^t$ and $\chi_{NO}{}^t$ according to equation (44). The values thus determined ($\chi_{O3}{}^t$) are listed in row 13, Table 3 for each sampling time.

The concentration at time t of NO$_y$ that would exist in the absence of NO$_y$ removal processes from air ($^o\chi_{NOy}{}^t$), and which represents the cumulative emissions of NO$_y$ into air is calculated from the values determined for $\chi_{NOy}{}^t$, $\chi_{NO}{}^t$ and $\chi_{O3}{}^t$ as follows.

The value of G is determined by equation (58) and the value of $^o\chi_{NOy}{}^t$ determined by equation (59) when $G^t < 1$ other wise by equation (60).

The value of $G^t$ and corresponding value of $^o\chi_{NOy}{}^t$ for air at each time of sampling are listed in Table 3, rows 14 and 15 respectively.

The maximum potential amount of smog formation in air ($^{max}\chi_{smog}{}^t$) is determined by application of equation (31).

The value thus determined for air at each time of sampling is given in Table 3, row 16.

The extent of prior smog formation in air ($^f\chi_{smog}{}^t$) is calculated from the measurements according to equation (61) and according to the value of $G^t$ and where $P_{7,2} = 0.125$ and $^oF_{NO} = 0.9$. The values thus determined for $^f\chi_{smog}{}^t$ are given in Table 3, row 17.

The extent of smog formation in air at time t ($E_{smog}{}^t$) is calculated from $^f\chi_{smog}{}^t$ and $^{max}\chi_{smog}{}^t$ according to equation (35).

The values of $E_{smog}{}^t$ determined for air at each time of sampling are given in Table 3, row 18.

The concentration of reactive organic compounds $\chi_{ROC}{}^t$ in air s determined from the measured reactivity coefficient for smog formation in air ($R_{smog}{}^t$) and a known value for the activity coefficient for smog formation of the ROC mixture as previously emitted into the air and sampled at time t ($a_{ROC}{}^t$). Now the value of $a_{ROC}{}^t$ can be separately determined by introducing a known amount of the ROC mixture into the system as described for calibration or, alternatively, a value can be assumed.

For the range of compositions of ROC mixtures commonly emitted into urban air the value of $a_{ROC}{}^t$ is approximately constant over the range of ROC compositions, Hence it is satisfactory to use a general value of $a_{ROC}{}^t$. The general value is not determined for the particular ROC mixture present in air at the time of sampling.

For the air being monitored in the present application a value of $a_{ROC}{}^t$ of 0.0067 moles smog/moles of ROC carbon/unit illumination/unit f(T) was chosen as applicable.

The concentration of reactive organic compounds in air at time t ($\chi_{ROC}{}^t$) is given by equation (105)

$$\chi_{ROC}{}^t = R_{smog}{}^t / a_{ROC}{}^t \qquad (105)$$

The concentration of ROC in air thus determined for each time of air sampling according to equation (105) are given in row 19 of Table 3 in units of carbon atoms of ROC/million molecules of air, (ppmC).

To a good approximation the activity coefficient for smog formation in air ($a_{ROC}{}^t$) is independent of the amount of illumination to which the ROC/air mixture has been exposed. Thus to a good approximation the concentration of ROC carbon measured by the system according to equation (105) is equivalent to the total amount of ROC carbon previously introduced into the air thus, $$^o\chi_{ROC}{}^t = \chi_{ROC}{}^t \qquad (106)$$

where $^o\chi_{ROC}{}^t$ denotes the total concentration of ROC carbon previously introduced into the air.

Table 3 lists in row 20 the value of $^o\chi_{ROC}{}^t$ thus determined by equation (106) for each time of air sampling.

The reactive organic compounds to nitrogen oxides emission ratio ($^o\chi_{ROC}{}^t / ^o\chi_{NOx}{}^t$) of smog precursor emissions is a characteristic of air commonly used in air quality evaluations and in the assessment of the smog forming characteristics of air. The value of $^o\chi_{ROC}{}^t / ^o\chi_{NOx}{}^t$ is determined by operation of system 100. For fresh emissions and as indicated by equation (10)

$$\chi_{NO_x}{}^t = \chi_{NO_y}{}^t \qquad (107)$$

and also given relation (106) then:

$$^o\chi_{ROC}{}^t/^o\chi_{NO_x}{}^t \leq \chi_{ROC}{}^t/^o\chi_{NO_y}{}^t \qquad (108)$$

The values of $^o\chi_{ROC}{}^t/^o\chi_{NO_x}{}^t$ determined according to equation (108) for each time of air sampling of the example are given in Table 3, row 21.

System 100 can be used to determine the nitric oxide and ozone concentrations in air by an alternative procedure to that yielding the results of Table 3, rows 12 and 13. The temperature and illumination intensity of air is measured by sensors 123 and 124 respectively and the value of $k_3{}^t$, the rate coefficient for $NO_2$ photolysis in the air determined from the readings. The values of $k_3{}^t$ determined for this example are listed in Table 2. The nitric oxide and ozone concentrations ($\chi_{NO}{}^t$, $\chi_{O_3}{}^t$) of air determined according to equations (68), (69) or (73) and (74) depending on the domain of $f_{\chi_{smog}}{}^t$ as given f t by expression (70). Now (70) can be evaluated because, following equation (11):

$$^o\chi_{NO}{}^t = {}^oF_{NO}{}^o\chi_{NO_y}{}^t \qquad (109)$$

and substituting equation (109) into (78) the specified domain of $f_{\chi_{smog}}{}^t$ is:

$$(^oF_{NO}-H)^o\chi_{NO_y}{}^t < f_{\chi_{smog}}{}^t < (^oF_{NO}+L)^o\chi_{NO_y}{}^t \qquad (110)$$

The values defining the range of $\chi_{smog}{}^t$ and the applicability of equations (68) and (69) are calculated on the basis of the determined values of $\chi_{NO_y}{}^t$ and expression (127) and are listed in Table 3, rows 22 and 23 wherein H and L have been assigned the value $\frac{1}{2}$. The truth or falsity of expression (110) is determined by inspection from the data of Table 3, rows 22 and 23 and the results are tabulated in Table 3, row 24 When test (110) has value false $\chi_{NO}{}^t$ and $\chi_{O_3}{}^t$ are calculated according to equations (68) and (69) otherwise equations (73) and (74) are employed. The concentrations so determined for each time of sampling air are given in Table 3, rows 25 and 26.

The value of $k_4$ employed in this calculation was taken from the literature, $k_4=2.66 \times 10^{33} e^{-1370/T^t}$ ppm$^{-1}$ min$^{-1}$.

The time period required for production of selected amount of smog ($^{select}\chi_{smog}{}^t$) in air of composition as determined at time t can be determined by application of system 100 and calculation of time period according to equations (82) and (83). Two applications of this method are of special interest, namely determination of the time period of prior smog formation in air and time period required for smog formation in air to reach maximum extent under selected conditions of temperature and illumination.

The time period required for maximum smog formation for air of composition as determined for each time of sampling and for temperature and illumination conditions for the day as measured and tabulated in Table 2 is determined as follows. The amount of extra smog required to be produced to reach $(^{fmax}\chi_{smog}{}^t)$ is determined from the measurements according to equation (79).

The time period ($t_2-t_1$) where $t_1$ is the time of sampling and $t_2$ is the time of onset $(^{fmax}\chi_{smog}{}^t)$ is determined for the conditions according to equation (80).

The integral can be evaluated for the data according to the trapezoidal rule and where $R^t$ is the value of $R_{smog}{}^t$ determined for air at time of sampling, $t_1$.

The value of the integral $$\int_{t=\text{dawn}}^{t=t} I'f(T^t) \cdot dt$$

where $f(T^t) = e^{-4700(1/T^t - 1/316)}$ and where $t_{dawn}=0622$ hr was evaluated for each time of air sampling and the values obtained are tabulated in Table 2.

Now from equations (79) and (80) $(^{fmax}\chi_{smog}{}^t)$ is attained at time $t_{max}$ for air sampled at time t when $$\int_{t=\text{dawn}}^{t=t} I'f(T^t) \cdot dt + ((^{pmax}\chi_{smog}{}^t) - f_{\chi_{smog}}{}^t)/R_{smog}{}^t = \qquad (112)$$

$$\int_{t=\text{dawn}}^{t=t_{max}} I'f(T^t) \cdot dt$$

Thus the time at which the maximum smog formation would be reached under the selected conditions of temperature and sunlight intensity observed during the day at the sampling site and in the absence of further $NO_y$ emissions into the air after the time of air sampling is determined for each sampling time by evaluation of the left hand side of equation (112) and by determining the time corresponding to this value by interpolation of the values of $$\int_{t=0622}^{t=t} I'f(T^t) \cdot dt \text{ listed in Table 2}$$

The values obtained for the left hand side of expression (112) are given in Table 3, row 27 and the corresponding time of day when maximum smog formation was attained determined by interpolation of data listed in Table 2 for each time of sampling are given in Table 3, row 28 and where the value $>18$ indicates that the potential maximum formation of smog is not reached before sunset (i.e. $t=18$) on that day.

The time period ($t_t-t_o$) during which smog formation in air has occurred may be determined according to equation (81), given that when the conditions $f_{\chi_{smog}}{}^t = \beta^o\chi_{NO_x}{}^t$ is true the period determined is a minimum period. Knowledge of the time period and the time of measurement ($t_t$) enables the apparent time of emission of ROC (i.e. an average time of the ROC emissions weighted with respect to the ROC emission strengths and sunlight intensities) into the air ($t_o$) to be determined by equation (113), the time corresponding to the beginning of the smog forming period.

$$t_o = t_t - (t_t-t_o) \qquad (113)$$

It is convenient to calculate the value of $$\int_{t=\text{dawn}}^{t=t} I'f(T) \cdot dt$$

throughout the day, as given in Table 2. From equations (81) and (113) equation (114) is obtained.

$$\int_{t=\text{dawn}}^{t=t_o} I'f(T)dt = \quad (114)$$

$$\left(\int_{t=\text{dawn}}^{t=t} I'f(T) \cdot dt\right) - f\chi_{smog}^t/R_{smog}^t$$

The times ($t_o$) corresponding to the values determined by equation (114) for $$\int_{t=\text{dawn}}^{t=t_o} I'f(T) \cdot dt$$

may be obtained by interpolation from Table 2. The values thus determined by application of equation (114) for $$\int_{t=\text{dawn}}^{t=t_o} I'f(T) \cdot dt$$

and the corresponding values for $t_O$, the apparent time of ROC emissions, for air at each time of sampling are given in Table 3 rows 29 and 30 and where the value $t_o$ of <06 indicates that the ROC entered the air previous to the day of measurement. For air that was sampled during the period 11.29 to 12.30 hrs and at 14.04 hrs the data is consistent with significant quantities of ROC having been emitted into the air at about dawn otherwise the results indicate that the smog forming activity of the air sampled during the day is attributable to ROC emitted to the air on days previous to the day of measurement.

The general case for determination of time period for production of selected amount of smog in air is here illustrated by way of example for one air analysis. For air of the same characteristics as the sample the smog, ozone and nitric oxide concentrations to be expected throughout the selected time period, namely from dawn to dusk on the day of sampling are determined. The air sample for this example is arbitrarily chosen as sampled at 1145 hrs. The procedure described is applicable to sampled at other times. Smog concentrations to be expected at selected times are determined from the data obtained by operation of system 100 using equation (81).

For this example the nitrogen oxides determined as present in the air at time of sampling are assumed to have been present throughout the previous daylight hours. The ROC is taken to be emitted into the air at a single time corresponding to the determined mean time of ROC emission ($t_o$), i.e. 08.30 hr on the day of sampling.

The value of $$\int_{t=o}^{t=t} I'f(T) \cdot dt,$$

where $t=O$ is the time of ROC emission as previously determined for the 1145 sample (i.e. $t=0$ corresponding to 0830 hrs), is calculated from the data listed in Table 2 for selected times. The values obtained are given in Table 4. The value of $^o\chi_{NOy}^t$ for all values of t is as determined for the sample air at 1145, i.e. $^o\chi_{NOy}^t=0.17$ ppm, see Table 3. The value for $R_{smog}^t$ smog prior to the determined time of ROC emission is: $R_{smog}^t$ ($t<([t=o])=0.0$ while for all times $t\geq[t=o]$, $R_{smog}^t=8.5\times10^{-3}$ as determined for the 1145 sample and as listed in Table 3. The air temperature at selected times is given in Table 2. The predicted concentrations of smog formed ($f\chi_{smog}^t$) calculated using the sunlight data of Table 4 by equation (81) for each selected time and the results are listed in Table 4. The initial value for the nitric oxide concentration is determined from the value for $^o\chi_{NOy}^t$ by application of equation (109) and hence ($^oF_{NO}$ having the value 0.9) $^o\chi_{NO}^{t=o}$ has the value of 0.13 ppm.

The domain of $f\chi_{smog}^t$ is tested by inequality (110) ($0.044<f\chi_{smog}^t<0.218$).

The value, true (T) or false (F), thus determined for each time are given in Table 4.

When condition (110) has value false the nitric oxide concentrations to be expected at those selected times ($\chi_{NO}^t$) are calculated according to equation (68) when the value is true $\chi_{NO}^t$ is obtained by application of equation (73). Similarly ozone concentrations are determined by equation (69) when the value is false and by (74) when the value is true.

The predicted concentrations of nitric oxide and ozone thus determined for selected times and for conditions of no dispersion or dilution of the air are given in Table 4. The values for light intensity and air temperature used are given in Table 2.

INDUSTRIAL APPLICABILITY

The methods and systems of the invention have the following industrial applicabilities:

(a) Total smog concentration of air can be determined by measurement of a single species, NO, instead of needing to determine $NO_x$, NO, $O_3$, ROC's etc.

(b) Smog forming activity of the air can be directly measured instead of having to estimate it by determination of ROC's, their composition and concentrations and as well separately modelling the detailed chemistry of the smog-forming process which requires carrying out of complex and approximate chemical kinetic calculations.

(c) Prospects for smog formation can be assessed in real time.

(d) Ozone and nitrogen oxides concentrations can be determined via the one detector (an NO detector).

(e) The duration of prior smog formation can be determined in a straightforward manner. Prior art gives no satisfactory means of determining duration of prior smog formation.

(f) Prospective course of smog formation can be quantitatively predicted from measurement of a single air sample. Prior art offers no alternative means for making such predictions from a single instrumental analysis.

(g) A sensitive means for determining the amount of prior ROC and nitrogen oxides emissions into the air, independently of the reaction or length of the period of residence in the air is made available. Determination of ROC by alternative means gives results which are biased low due to transformation by reaction of the ROC emissions into chemical forms which are not easily detected by existing ROC analysis methods.

(h) A measure of smog formation is made available which varies proportion to the total amount of smog formation (unlike prior types of measurements which determine the concentration of a single species, e.g. NO or $O_3$, the concentrations of which vary nonlinearly with total smog formation).

(i) Smog formation can be characterised by only three measured parameters, namely $NO_y$ concentration, smog concentration and rate coefficient for smog formation, instead of having to specify the behaviour of numerous chemical species.

(j) The location of the sources of ROC emissions can be estimated from the duration of smog formation in air and knowledge of the trajectory and speed of the air during smog formation.

(k) The most effective option for controlling formation of excessive ozone concentrations in air can be determined from the value of extent of smog formation in air. When the extent approaches the value 1 then minimization of nitrogen oxides is the indicated strategy. When extent is less than 1 then control of ROC emissions is the indicated strategy.

(l) The concentrations of nitrogen oxides converted to nitric acid or lost from the gas phase can be determined. This is of particular practical importance as it is a measure of the quantity of nitrogen available for acidic or nitrate deposition from the air.

TABLE 1

Data measured for calibration of Reactor 107

| (min) | $^{CI}x_{NO}{}^t - {}^{CII}x_{NO}{}^t$ (ppm) | $te^{-k_{90}t}$ ($k_{90} = 8.52 \times 10^{-2}$) |
|---|---|---|
| 0 | 0.0000 | 0.00 |
| 1 | 0.0154 | 0.92 |
| 2 | 0.0280 | 1.69 |
| 3 | 0.0350 | 2.32 |
| 4 | 0.0420 | 2.84 |
| 5 | 0.0490 | 3.27 |
| 6 | 0.0490 | 3.60 |
| 7 | 0.0546 | 3.86 |
| 17 | 0.0595 | 3.99 |
| 18 | 0.0581 | 3.88 |
| 19 | 0.0567 | 3.76 |
| 20 | 0.0525 | 3.64 |
| 31 | 0.0336 | 2.21 |
| 32 | 0.0350 | 2.09 |
| 33 | 0.0315 | 1.98 |
| 44 | 0.0175 | 1.04 |
| 45 | 0.0168 | 0.97 |
| 46 | 0.0182 | 0.91 |
| 57 | 0.0084 | 0.44 |
| 58 | 0.0077 | 0.41 |
| 59 | 0.0084 | 0.39 |

Line of best fit: $({}^{CI}x_{NO}{}^t - {}^{CII}x_{NO}{}^t) = 0.0139\, te^{-0.0852t} + 0.0029$

TABLE 2

Measured temperature and sunlight intensities of the atmosphere for selected period including the period of operation of System 100 in FIG. 12

| Time of Day (t) (hr, min) | Temperature ($T^t$, °K.) | Sunlight Intensity ($k_3{}^t$, min$^{-1}$) | $\int_{t=0622}^{t=t} I\, f(T^t) \cdot dt$ |
|---|---|---|---|
| 06.22 | 285 | 0.000 | 0.0 |
| 06.37 | 284 | 0.009 | 0.0 |
| 06.52 | 283 | 0.008 | 0.0 |
| 07.07 | 283 | 0.062 | 0.1 |
| 07.22 | 284 | 0.071 | 0.3 |
| 07.37 | 286 | 0.093 | 0.6 |
| 07.52 | 287 | 0.123 | 0.9 |
| 08.07 | 288 | 0.137 | 1.4 |
| 08.22 | 290 | 0.166 | 1.9 |
| 08.30 | — | — | 2.3 |
| 08.37 | 292 | 0.198 | 2.7 |
| 09.52 | 293 | 0.182 | 3.6 |
| 09.07 | 293 | 0.218 | 4.5 |
| 09.22 | 295 | 0.234 | 5.6 |
| 09.37 | 297 | 0.260 | 7.0 |
| 09.42 | 296 | 0.304 | 7.5 |
| 09.58 | 298 | 0.305 | 9.4 |
| 10.13 | 295 | 0.352 | 11.2 |
| 10.29 | 296 | 0.364 | 13.3 |
| 10.44 | 297 | 0.379 | 15.3 |
| 10.59 | 297 | 0.272 | 17.2 |
| 11.13 | 298 | 0.397 | 19.0 |
| 11.29 | 297 | 0.402 | 21.6 |
| 11.45 | 297 | 0.406 | 24.1 |
| 12.00 | 298 | 0.415 | 26.5 |
| 12.31 | 298 | 0.431 | 31.8 |
| 13.02 | 298 | 0.392 | 37.0 |
| 13.33 | 299 | 0.426 | 42.3 |
| 14.04 | 299 | 0.349 | 47.4 |
| 14.51 | 299 | 0.338 | 54.5 |
| 15.22 | 301 | 0.359 | 59.5 |
| 15.53 | 301 | 0.325 | 64.6 |
| 16.24 | 299 | 0.292 | 69.0 |
| 16.54 | 298 | 0.280 | 72.7 |
| 17.25 | 298 | 0.225 | 75.8 |
| 17.55 | 297 | 0.151 | 78.1 |
| 18.26 | 296 | 0.000 | 79.0 |

TABLE 3

Example of Smog Monitoring Data obtained by operation of System 100 depicted in FIG. 12

| Row | t | | 0958 | 1013 | 1029 | 1044 | 1059 | 1113 | 1129 | 1145 | 1200 | 1231 | 1302 | 1333 | 1404 | 1451 | 1522 | 1553 | 1624 | 1654 |
|---|---|---|---|---|---|---|---|---|---|---|---|---|---|---|---|---|---|---|---|---|
| 1 | | Time of air Sampling (hr, min) | | | | | | | | | | | | | | | | | | |
| 2 | | $A^t{}_{XNO}{}^t$ (ppm) | 0.001 | 0.006 | 0.005 | 0.004 | 0.004 | 0.011 | 0.021 | 0.025 | 0.023 | 0.015 | 0.005 | 0.000 | −0.001 | −0.001 | −0.003 | −0.003 | −0.002 | −0.002 |
| 3 | | $A^t{}_{f}X_{NO}{}^t$ (ppm) | 09.016 | 0.028 | 0.027 | 0.031 | 0.038 | 0.086 | 0.126 | 0.151 | 0.156 | 0.127 | 0.085 | 0.044 | 0.024 | 0.017 | 0.006 | 0.007 | 0.005 | 0.006 |
| 4 | | $B^t{}_{XNO}{}^t$ (ppm) | 0.260 | 0.291 | 0.284 | 0.266 | 0.249 | 0.241 | 0.258 | 0.262 | 0.254 | 0.226 | 0.187 | 0.136 | 0.173 | 0.190 | 0.185 | 0.191 | 0.208 | 0.206 |
| 5 | | $B^t{}_{f}X_{NO}{}^t$ (ppm) | 0.331 | 0.343 | 0.342 | 0.346 | 0.353 | 0.401 | 0.441 | 0.466 | 0.471 | 0.442 | 0.400 | 0.359 | 0.339 | 0.332 | 0.308 | 0.315 | 0.317 | 0.316 |
| 6 | | $C^t{}_{XNO}{}^t$ (ppm) | 0.293 | 0.292 | 0.285 | 0.269 | 0.254 | 0.243 | 0.250 | 0.259 | 0.245 | 0.220 | 0.180 | 0.132 | 0.169 | 0.191 | 0.203 | 0.190 | 0.205 | 0.206 |
| 7 | | $C^t{}_{f}X_{NO}{}^t$ (ppm) | 0.292 | 0.290 | 0.285 | 0.272 | 0.251 | 0.241 | 0.237 | 0.241 | 0.234 | 0.210 | 0.175 | 0.128 | 0.161 | 0.186 | 0.202 | 0.188 | 0.202 | 0.205 |
| 8 | | $T_{t}{}_{1}Q_{smog}{}^t \times 10^4$ | 0.9 | 1.7 | 0.0 | (−2.6) | 2.6 | 1.7 | 11.2 | 15.6 | 9.5 | 8.7 | 4.3 | 3.5 | 6.9 | 4.3 | 0.9 | 1.7 | 2.6 | 0.9 |
| 9 | | $R_{smog}{}^t \times 10^4$ (ppm/min) | 4.4 | 8.8 | 0.0 | (−13) | 13 | 8.8 | 57 | 79 | 48 | 44 | 22 | 18 | 35 | 22 | 4.4 | 8.8 | 13 | 4.4 |
| 10 | | $X_{smog}{}^t$ (ppm) | 0.07 | 0.05 | 0.06 | 0.08 | 0.10 | 0.16 | 0.18 | 0.20 | 0.22 | 0.22 | 0.21 | 0.22 | 0.18 | 0.14 | 0.14 | 0.12 | 0.11 | 0.12 |
| 11 | | $X_{NOy}{}^t$ (ppm) | 0.02 | 0.03 | 0.03 | 0.03 | 0.04 | 0.09 | 0.13 | 0.15 | 0.16 | 0.13 | 0.08 | 0.04 | 0.02 | 0.02 | 0.01 | 0.01 | 0.00 | 0.01 |
| 12 | | $X_{NO}{}^t$ (ppm) | 0.00 | 0.01 | 0.00 | 0.00 | 0.00 | 0.01 | 0.02 | 0.02 | 0.02 | 0.02 | 0.00 | 0.04 | 0.00 | 0.00 | 0.00 | 0.00 | 0.00 | 0.00 |
| 13 | | $X_{O_3}{}^t$ (ppm) | 0.06 | 0.03 | 0.04 | 0.05 | 0.07 | 0.08 | 0.08 | 0.14 | 0.08 | 0.10 | 0.13 | 0.18 | 0.15 | 0.12 | 0.14 | 0.12 | 0.10 | 0.11 |
| 14 | | $G^t$ | 0.62 | 0.26 | 0.33 | 0.40 | 0.41 | 0.23 | 0.15 | 0.18 | 0.18 | 0.20 | 0.39 | 0.82 | 1.11 | 0.98 | 1.46 | 1.37 | 2.29 | 1.32 |
| 15 | | $^1X_{NOy}{}^t$ (ppm) | 0.03 | 0.03 | 0.03 | 0.04 | 0.05 | 0.11 | 0.15 | 0.18 | 0.18 | 0.16 | 0.11 | 0.07 | 0.05 | 0.04 | 0.04 | 0.04 | 0.03 | 0.04 |
| 16 | | $f_{max}X_{smog}{}^t$ | 0.10 | 0.14 | 0.14 | 0.17 | 0.21 | 0.43 | 0.60 | 0.71 | 0.74 | 0.62 | 0.46 | 0.30 | 0.19 | 0.16 | 0.17 | 0.15 | 0.13 | 0.14 |
| 17 | | $^1f_{XNOy}{}^t$ (ppm) | 0.08 | 0.06 | 0.06 | 0.09 | 0.11 | 0.17 | 0.19 | 0.21 | 0.23 | 0.23 | 0.23 | 0.25 | 0.19 | 0.16 | 0.18 | 0.16 | 0.13 | 0.14 |
| 18 | | $E_{smog}{}^t$ | 0.75 | 0.40 | 0.44 | 0.52 | 0.54 | 0.44 | 0.32 | 0.30 | 0.31 | 0.37 | 0.51 | 0.82 | 1.00 | 1.00 | 1.00 | 1.00 | 1.00 | 1.00 |
| 19 | | $X_{ROC}{}^t$ (ppmC) | 0.07 | 0.13 | 0.00 | −0.20 | 0.20 | 0.13 | 0.85 | 1.18 | 0.72 | 0.66 | 0.33 | 0.26 | 0.52 | 0.33 | 0.07 | 0.13 | 0.20 | 0.07 |
| 20 | | $^oX_{ROC}{}^t$ (ppmC) | 0.07 | 0.13 | 0.00 | −0.20 | 0.20 | 0.13 | 0.85 | 1.18 | 0.72 | 0.65 | 0.33 | 0.26 | 0.52 | 0.33 | 0.07 | 0.13 | 0.20 | 0.07 |
| 21 | | $^oX_{ROC}{}^t/^oX_{NOx}{}^t$ (ppmC/ppm) | 2.5 | 3.7 | 0.0 | — | 3.8 | 1.2 | 5.6 | 6.6 | 3.9 | 4.2 | 2.9 | 3.5 | 10.9 | 8.4 | 1.5 | 3.5 | 6.0 | 1.8 |
| 22 | | $(^oX_{NOy}{}^t - ^o_1{}^1X_{NOy}{}^t)$ | 0.010 | 0.014 | 0.014 | 0.017 | 0.005 | 0.010 | 0.060 | 0.071 | 0.074 | 0.062 | 0.046 | 0.030 | 0.019 | 0.016 | 0.017 | 0.148 | 0.013 | 0.014 |
| 23 | | $(^oX_{NO}{}^t + ^o_1{}^1X_{NOy}{}^t)$ | 0.036 | 0.049 | 0.049 | 0.059 | 0.073 | 0.149 | 0.211 | 0.249 | 0.259 | 0.218 | 0.159 | 0.105 | 0.067 | 0.055 | 0.060 | 0.052 | 0.046 | 0.050 |
| 24 | | Test (110) (T/F) | F | F | F | F | F | F | T | T | T | F | F | F | F | F | F | F | F | F |
| 25 | | $X_{NO}{}^t$ via(68)(73) ppm | 0.00 | 0.00 | 0.00 | 0.00 | 0.00 | 0.00 | 0.02 | 0.02 | 0.02 | 0.00 | 0.00 | 0.00 | 0.00 | 0.00 | 0.00 | 0.00 | 0.00 | 0.00 |
| 26 | | $X_{O_3}{}^t$ via(69)(74) (ppm) | 0.05 | 0.02 | 0.03 | 0.05 | 0.07 | 0.07 | 0.08 | 0.08 | 0.08 | 0.09 | 0.13 | 0.18 | 0.15 | 0.12 | 0.14 | 0.12 | 0.10 | 0.11 |
| 27 | | $\int_{t=dawn}^{t=tmax} I^t(T^t)\cdot dt$ | 69 | 107 | — | — | 89 | 311 | 94 | 87 | 133 | 122 | 139 | 73 | 46 | 44 | 44 | 57 | 66 | 59 |
| 28 | | $max_{tsmog}{}^t$ (hr) | 16 | >18 | — | — | >18 | >18 | >18 | >18 | >18 | >18 | >18 | 17 | 14 | 14 | 14 | 15 | 16 | 15 |
| 29 | | $\int_{t=to}^{t=tmax} I^t(T^t)\cdot dt$ | −168 | −52 | — | — | −69 | −176 | −12 | 3 | −20 | −20 | −68 | −98 | −8 | ≦−26 | ≦−347 | ≦−112 | ≦−36 | ≦−268 |
| 30 | | $t_o$ (hr) | <06 | <06 | <06 | <06 | <06 | <06 | <06 | 09 | <06 | <06 | <06 | <06 | 08 | <06 | <06 | <06 | <06 | <06 |

TABLE 4

Concentration-Time Profiles predicted for air with characteristics as air sampled at 11.45 hrs and conditions of temperature and illumination as determined at the sampling site on that day.

| Time of Day (hr, min) | $\int_{t=0}^{t=t} I^t f(T^t) \cdot dt$ $f_{\chi_{smog}{}^t}$ (ppm) | Test(110) T/F | Predicted $\chi_{NO}{}^t$ (ppm) | Predicted $\chi_{O_3}{}^t$ (ppm) |
|---|---|---|---|---|
| 0622 (dawn) | 0.0 | 0.0 | F | 0.17 | 0.00 |
| 0637 | 0.0 | 0.0 | F | 0.17 | 0.00 |
| 0652 | 0.0 | 0.0 | F | 0.17 | 0.00 |
| 0707 | 0.0 | 0.0 | F | 0.17 | 0.00 |
| 0722 | 0.0 | 0.0 | F | 0.17 | 0.00 |
| 0737 | 0.0 | 0.0 | F | 0.17 | 0.00 |
| 0752 | 0.0 | 0.0 | F | 0.17 | 0.00 |
| 0807 | 0.0 | 0.0 | F | 0.17 | 0.00 |
| 0822 | 0.0 | 0.0 | F | 0.17 | 0.00 |
| ROC determined as being introduced into air at 0830 | | | | | |
| 0830 | 0.0 | 0.0 | F | 0.17 | 0.00 |
| 0837 | 0.38 | 0.00 | F | 0.17 | 0.00 |
| 0852 | 1.24 | 0.01 | F | 0.16 | 0.00 |
| 0907 | 2.17 | 0.02 | F | 0.16 | 0.00 |
| 0922 | 3.29 | 0.03 | F | 0.15 | 0.00 |
| 0937 | 4.65 | 0.04 | F | 0.14 | 0.00 |
| 0942 | 5.17 | 0.04 | F | 0.14 | 0.00 |
| 0958 | 7.03 | 0.06 | F | 0.12 | 0.00 |
| 1013 | 8.87 | 0.07 | F | 0.11 | 0.00 |
| 1029 | 10.93 | 0.09 | T | 0.10 | 0.00 |
| 1044 | 13.00 | 0.10 | T | 0.09 | 0.01 |
| 1059 | 14.84 | 0.12 | T | 0.08 | 0.01 |
| 1113 | 16.68 | 0.13 | T | 0.07 | 0.02 |
| 1129 | 19.23 | 0.15 | T | 0.06 | 0.03 |
| 1145 | 21.76 | 0.17 | T | 0.05 | 0.04 |
| 1200 | 24.19 | 0.19 | T | 0.04 | 0.05 |
| 1231 | 29.49 | 0.23 | T | 0.03 | 0.08 |
| 1302 | 34.71 | 0.28 | F | 0.00 | 0.10 |
| 1333 | 39.95 | 0.32 | F | 0.00 | 0.14 |
| 1404 | 45.09 | 0.36 | F | 0.00 | 0.18 |
| 1451 | 52.14 | 0.41 | F | 0.00 | 0.23 |
| 1522 | 57.14 | 0.45 | F | 0.00 | 0.27 |
| 1553 | 62.31 | 0.49 | F | 0.00 | 0.32 |
| 1624 | 66.72 | 0.53 | F | 0.00 | 0.35 |
| 1654 | 70.33 | 0.56 | F | 0.00 | 0.38 |
| 1725 | 73.51 | 0.58 | F | 0.00 | 0.40 |
| 1755 | 75.74 | 0.60 | F | 0.00 | 0.42 |
| 1826 (dusk) | 76.65 | 0.61 | F | 0.00 | 0.43 |

I claim:

1. A method for determining rate coefficient of smog formation in air, the method comprising:
   (a) adding excess nitric oxide to an air sample to provide an excess nitric oxide/air mixture;
   (b) permitting the mixture to react for a first selected reaction period wherein excess nitric oxide in the mixture reacts with substantially all ozone in the mixture;
   (c) determining a first nitric oxide concentration of the mixture after the first selected reaction period;
   (d) illuminating the mixture of (a) or the mixture after the first selected reaction period for a second selected reaction period under reference temperature and illumination conditions;
   (e) permitting the mixture, after illumination, to react for a third selected reaction period wherein excess nitric oxide in the mixture reacts with any ozone present in the mixture;
   (f) determining a second nitric oxide concentration of the mixture after the third selected reaction period; and
   (g) determining the rate coefficient of smog formation from the first and second nitric oxide concentrations, the reference temperature and illumination conditions and the duration of the second selected reaction period.

2. A method for determining rate of smog formation in air under selected temperature and illumination conditions, which method comprises:
   (a) adding excess nitric oxide to an air sample to provide an excess nitric oxide/air mixture;
   (b) permitting the mixture to react for a first selected reaction period wherein excess nitric oxide in the mixture reacts with substantially all ozone in the mixture;
   (c) determining a first nitric oxide concentration of the mixture after the first selected reaction period;
   (d) illuminating the mixture of (a) or the mixture after the first selected reaction period for a second selected reaction period under selected temperature and illumination conditions;
   (e) permitting the mixture, after illumination, to react for a third selected reaction period wherein excess nitric oxide in the mixture reacts with any ozone present in the mixture;
   (f) determining a second nitric oxide concentration of the mixture after the third selected reaction period; and
   (g) determining the rate of smog formation from the first and second nitric oxide concentrations and the duration of the second selected reaction period.

* * * * *